United States Patent
Hull et al.

(10) Patent No.: US 10,820,639 B2
(45) Date of Patent: *Nov. 3, 2020

(54) GLOVE WITH CONTRASTING CUFF AND TEAR INDICATOR

(71) Applicant: Summit Glove Inc., Minerva, OH (US)

(72) Inventors: James L. Hull, Malvern, OH (US); Christopher J. Pearen, Brampton (CA); Ronald J. Thatcher, Bond Head (CA)

(73) Assignee: Summit Glove Inc., Minerva, OH (US)

( * ) Notice: Subject to any disclaimer, the term of this patent is extended or adjusted under 35 U.S.C. 154(b) by 140 days.

This patent is subject to a terminal disclaimer.

(21) Appl. No.: 16/209,169

(22) Filed: Dec. 4, 2018

(65) Prior Publication Data
US 2019/0125013 A1  May 2, 2019

Related U.S. Application Data

(63) Continuation-in-part of application No. 15/136,191, filed on Apr. 22, 2016, now Pat. No. 10,390,575.
(Continued)

(51) Int. Cl.
*A61B 42/30* (2016.01)
*A41D 19/00* (2006.01)
(Continued)

(52) U.S. Cl.
CPC ..... *A41D 19/0082* (2013.01); *A41D 19/0003* (2013.01); *A41D 19/0006* (2013.01);
(Continued)

(58) Field of Classification Search
CPC ......... A61B 42/30; A61B 42/10; A61B 42/20; A41D 19/0055; A41D 19/0082
See application file for complete search history.

(56) References Cited

U.S. PATENT DOCUMENTS 1,559,114 A   10/1925   Maranville
2,058,221 A   10/1936   Ferguson
(Continued)

FOREIGN PATENT DOCUMENTS

CA   3005865 A1 *   5/2017   ............ B29C 41/22

OTHER PUBLICATIONS

Nick Gardner, Accelerator Free Fact or Fiction, Shield Scientific B.V., Health & Safety International, pp. 77-82, Oct. 2008.
(Continued)

*Primary Examiner* — Tajash D Patel
(74) *Attorney, Agent, or Firm* — Sand, Sebolt & Wernow Co., LPA

(57) ABSTRACT

An ambidextrous or hand-specific glove including a wrist region, a palm region, and a digit region. The glove may be fabricated of nitrile rubber that is free of or essentially free of zinc, sulfur and accelerators to reduce allergic reactions in populations required to frequently wear protective gloves. A band region that partially or fully encircles a user's finger knuckles may be provided for easier finger bending. Texturing may be provided on glove surfaces that are used to grip articles. The fingertip regions on the front surface of the index and middle finger regions may be un-textured or smooth to enable a user to take a patient's pulse. These fingertip regions may be of reduced or smaller diameter and circumference so as to pull the glove material tightly around the tips of the user's finger and thereby applying pressure thereto so that even a faint pulse in a patient may be detected.

21 Claims, 41 Drawing Sheets

Related U.S. Application Data

(60) Provisional application No. 62/152,302, filed on Apr. 24, 2015.

(51) Int. Cl.
*A41D 19/015* (2006.01)
*A61B 42/10* (2016.01)

(52) U.S. Cl.
CPC ... *A41D 19/0044* (2013.01); *A41D 19/01547* (2013.01); *A41D 19/01558* (2013.01); *A61B 42/10* (2016.02); *A61B 42/30* (2016.02); *A41D 19/0058* (2013.01); *A41D 2400/80* (2013.01); *A41D 2500/50* (2013.01)

(56) References Cited

U.S. PATENT DOCUMENTS

| | | | |
|---|---|---|---|
| 2,075,550 A | 3/1937 | Smith | |
| 2,266,716 A | 12/1941 | Robertson | |
| 2,335,871 A | 12/1943 | Milligan | |
| 2,348,773 A | 5/1944 | Wyman | |
| 3,283,338 A | 11/1966 | Landau | |
| 4,149,601 A | 4/1979 | Taylor | |
| 4,507,807 A | 4/1985 | Karkanen | |
| 4,742,578 A * | 5/1988 | Seid | A61B 42/10 2/2.5 |
| 4,843,014 A * | 6/1989 | Cukier | A41D 19/0058 128/846 |
| 5,323,490 A | 6/1994 | Yarbrough | |
| 5,442,816 A | 8/1995 | Seketa | |
| 5,687,424 A | 11/1997 | Masley | |
| 5,924,137 A | 7/1999 | Gold | |
| 6,031,042 A | 2/2000 | Lipinski | |
| 6,032,290 A | 3/2000 | Lucas et al. | |
| 6,092,238 A | 7/2000 | Fierabend, Jr. | |
| 6,451,893 B1 | 9/2002 | Tao | |
| D513,827 S | 1/2006 | Ward | |
| 9,179,718 B2 | 11/2015 | Anstey | |
| 9,302,171 B1 | 4/2016 | Iacono | |
| 10,238,159 B2 | 3/2019 | Hull | |
| 10,390,575 B2 * | 8/2019 | Hull | A41D 19/0058 |
| 10,602,787 B2 | 3/2020 | Hull et al. | |
| 10,602,788 B2 * | 3/2020 | Hull | A41D 19/0082 |
| 2009/0139007 A1 | 6/2009 | Bevier | |
| 2012/0036612 A1 | 2/2012 | Hull | |
| 2013/0239291 A1 | 9/2013 | Harris | |
| 2013/0291282 A1 | 11/2013 | Anstey | |
| 2015/0164160 A1 | 6/2015 | Furlong | |
| 2017/0142931 A1 | 5/2017 | Michaelson et al. | |
| 2017/0231705 A1 | 8/2017 | Madison | |
| 2017/0295868 A1 | 10/2017 | Yahnite | |
| 2017/0318879 A1 | 11/2017 | Gleser | |
| 2017/0348065 A1 | 12/2017 | Bluecher et al. | |
| 2018/0263315 A1 | 9/2018 | Visokey | |
| 2019/0104783 A1 | 4/2019 | Hull et al. | |

OTHER PUBLICATIONS

SemperSure™ Nitrile, www.sempermedusa.com/products/sempersure, Sempermed USA, Inc., 2 pages, document is undated but was publically available as of Aug. 18, 2014.

Nitrile Accelerator-Free Micro-Touch®, www.ansell.be/medical/pdf/gloves/EN/Micro-Touch%20Nitrile%20Accelerator-Free.pdf, Ansell, 2 pages, document is undated but was publically available as of Aug. 18, 2014.

Accelerator-Free Nitrile Exam Gloves—A Better Alternative, http://hourglass-intl.com/2011/04/18/accelerator-free-nitrile-exam-gloves-a-better-alternative/, Hourglass International, 4 pages, Apr. 18, 2011.

New Glove Materials Make Nitrile Gloves Better, http://hourglass-intl.com/2011/01/24/new-glove-materials-make-nitrile-gloves-better/, Hourglass International, 2 pages, Jan. 24, 2011.

* cited by examiner

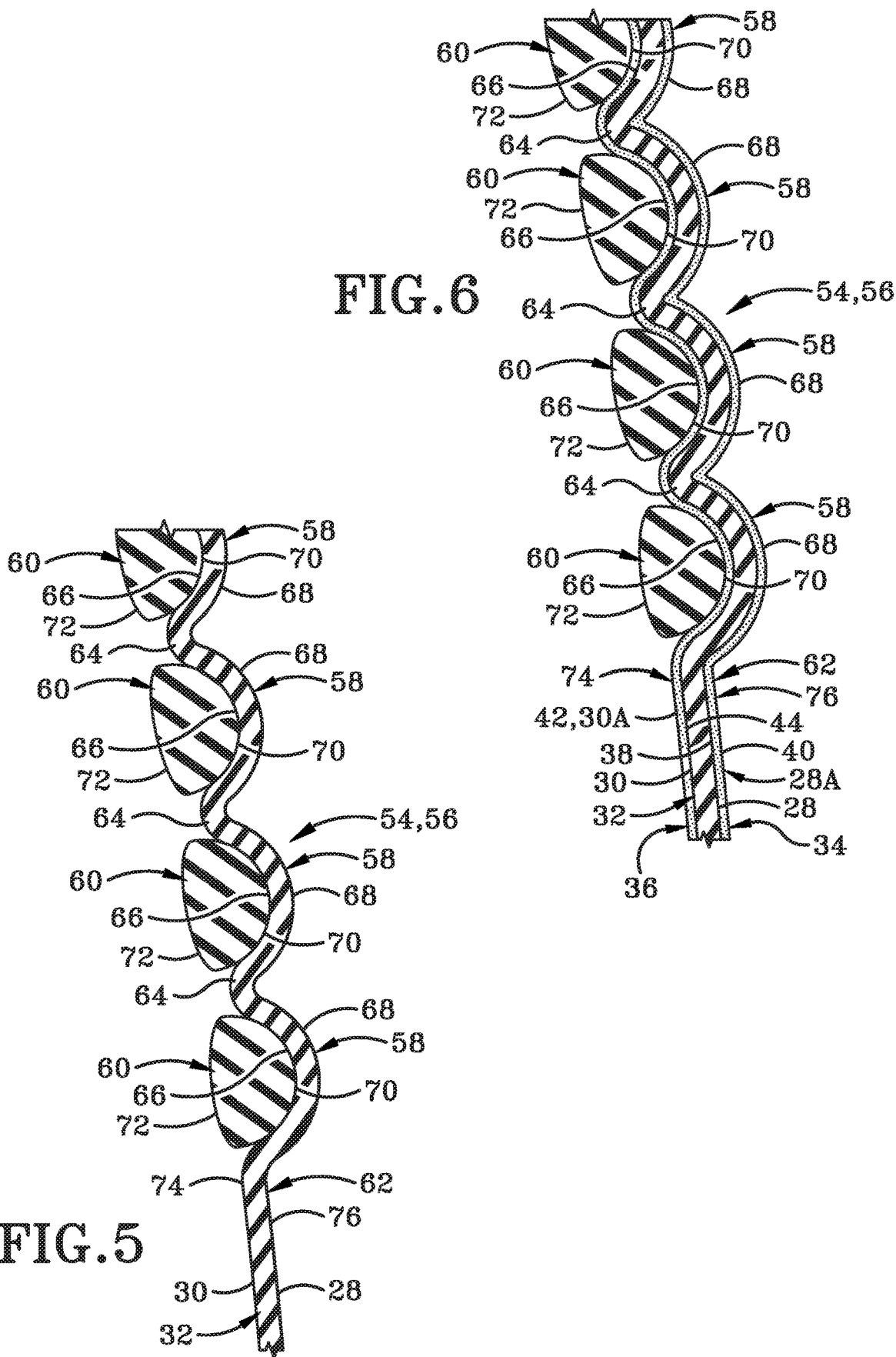

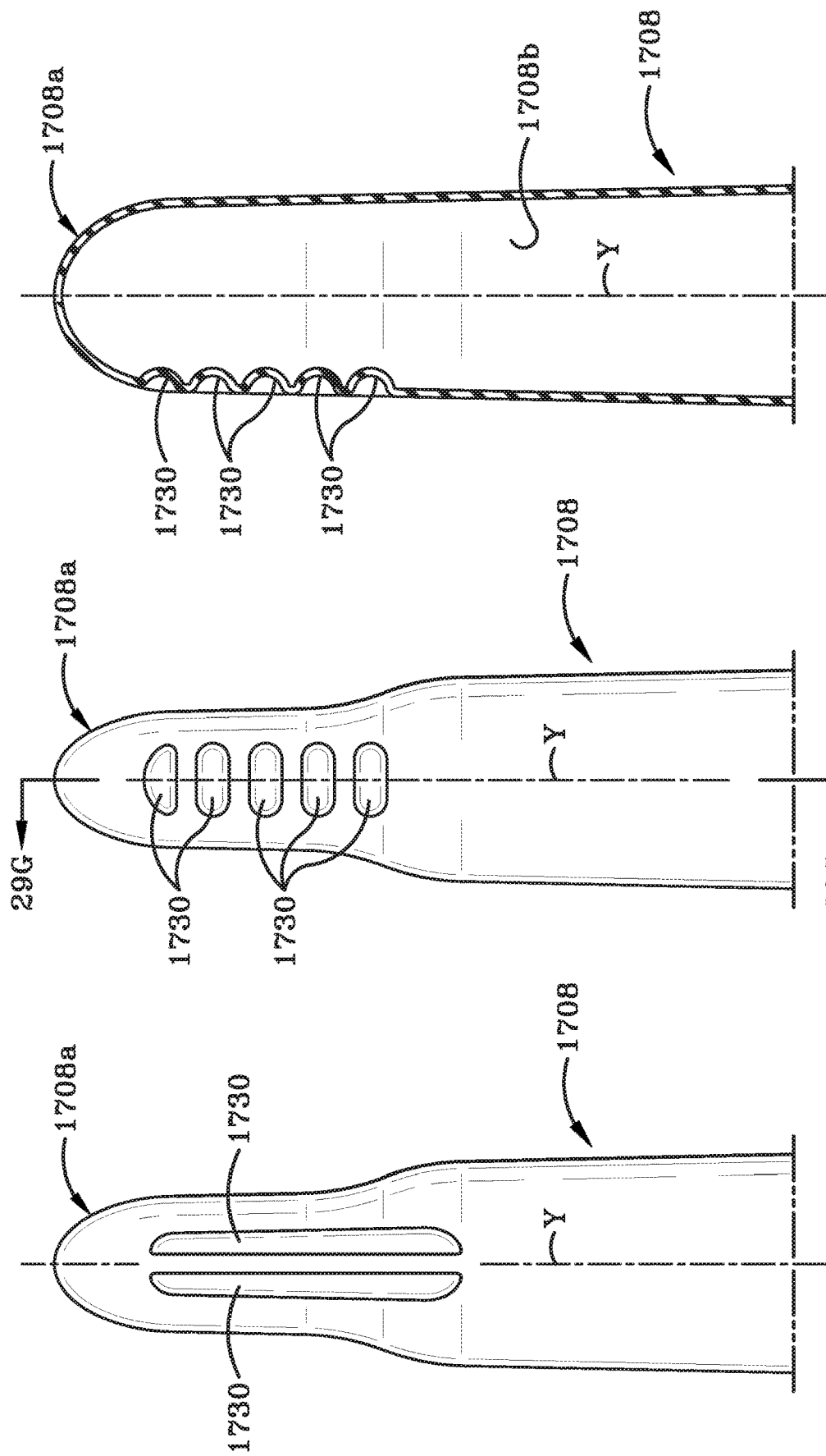

GLOVE WITH CONTRASTING CUFF AND TEAR INDICATOR

CROSS-REFERENCE TO RELATED APPLICATIONS

This application is a Continuation-in-Part of U.S. application Ser. No. 15/136,191 filed Apr. 22, 2016, which application claims the benefit of U.S. Provisional Application Ser. No. 62/152,302 filed Apr. 24, 2015, the entire disclosures of which are incorporated herein by reference in their entirety.

BACKGROUND

Technical Field

The present invention relates generally to gloves and more particularly to gloves, such as those that may be used by medical professionals. Specifically, the present invention relates to a glove fabricated from a material that is free of or essentially free of components that may cause hypersensitivity or allergic reaction in people who wear the glove. The glove material may be free of or essentially free of zinc and/or sulfur and/or accelerators. Furthermore, an index finger region and/or a middle finger region and/or a thumb region on the glove may be left un-textured (i.e., unpatterned or smooth) to enable the user to perform a medical procedure while wearing the glove; or the index or middle finger regions or the thumb region may be differently textured/patterned from the rest of the glove; and/or a fingertip region of the index or middle finger regions and/or the thumb region may be of a reduced or smaller circumference relative to a remaining portion of the associated finger or thumb region such that the material in the fingertip region may tend to be pulled taut over a tip of the user's finger or thumb.

Background Information

Nitrile or nitrile rubber gloves are well known in the art, such as for use in the medical field. One of the problems with such gloves is that some individuals have a hypersensitivity to various compounds that may be included in the gloves, such as zinc and/or sulfur and/or a variety of accelerators. Those accelerators may include but are not limited to components such as carbonates or thiurams. In addition, surgical or other gloves may have a tendency to stretch when worn for long periods of time, whereby the gloves may lose the ability to cling to the user's hand. This tendency for gloves to stretch may be a particular problem for surgeons.

SUMMARY

There is thus a need in the art for an improved glove for use by people such as medical professionals that will have less of a tendency to affect or cause allergic reactions in people with hypersensitivity to various components or compounds used in the production of the gloves. Further, there is a need for gloves that are designed to allow medical professionals to perform a variety of medical procedures, such as taking a patient's pulse, while wearing the glove. The glove disclosed herein will be discussed as being useful for taking a patient's pulse but it should be understood that the glove may be used for any of a number of different tasks or procedures that may require the user's tactile sensitivity and/or dexterity.

An ambidextrous glove and a hand-specific glove are disclosed herein. Each of the ambidextrous glove and the hand-specific gloves include a wrist region; a palm region; and a digit region. The wrist region, palm region and digit region define a hand-receiving cavity and the wrist region defines an opening to that hand-receiving cavity. The disclosed glove addresses some of the issues found with prior art gloves. The glove disclosed herein may be comprised of any suitable material such as any suitable rubber, e.g., nitrile rubber. If the glove is made from nitrile rubber it may include nitrile rubber that is free of or essentially free of zinc and/or sulfur and/or accelerators/accelarants. Some accelerators/accelarants that the glove's nitrile rubber may be free of or essentially free of may include carbonates or thiurams. The nitrile rubber that is free of zinc, sulfur, and accelerators (accelarants) may be the portion of the glove that contacts the user's skin.

The composition of the disclosed glove may tend to reduce hypersensitivity or allergic reactions in populations that may be required to frequently wear protective gloves. The glove may include a band region in the digit region that will partially encircle or fully encircle one or more of the user's knuckles of one or more of the user's fingers or thumb. These band regions tend to make it easier for the user to bend their fingers and/or thumb while wearing the glove. This improved bendability provided by the glove may help improve the user's dexterity while wearing the glove. The presence of the band regions may also reduce the tendency of the glove material to become stretched when the glove is worn for a long period of time.

The disclosed glove may additionally be provided with texturing on surfaces that may be used to grip articles such as the inside or front surfaces of the digit regions and the palm region. In such textured gloves the upper regions of the front surface on the index finger region and/or middle finger region may be left un-textured (i.e., texture-free) or smooth. The texturing on any glove surfaces may be provided by forming a pattern in or on an exterior surface of the glove. The pattern may be of any desired configuration such as a diamond pattern, a herringbone pattern, a fan pattern, a fish scale pattern, a sand pattern or texture, a wave pattern etc. The "smooth" regions of the glove will be free of any such texturing or pattern. The un-textured or smooth front surfaces on the index and/or middle finger regions and/or thumb region may enable the user to more easily take a patient's pulse than if these front surfaces were textured. The lack of texture may help ensure that the naturally-existing tactile sensitivity in the uppermost pads of the user's index finger and/or middle finger and/or thumb is as close as possible to how sensitive these regions of the user's fingers and thumb would be if no gloves are being worn. If a patient has an extremely weak pulse or is unconscious, it is extremely common that the vast majority of EMT's (Emergency Medical Technicians) will immediately tear the index and middle finger regions off previously known gloves in order to expose their bare skin so that they may try and locate the patient's pulse. This tends to occur no matter what size glove the EMT is using. When it comes to taking a pulse, if there is any overlapping material on the middle or index finger regions of a glove, then that extra material tends to interfere with taking a pulse, particularly if the patient's pulse if faint. Of course, tearing the index and middle finger regions off a glove will leave the EMT at risk of contamination or harm because they now have exposed skin handling an injured or unconscious patient. The glove disclosed herein addresses this issue in that the smooth fingertip regions on the index finger region and middle finger regions (and thumb region) may ensure that there is close proximity between the user's fingertips and the patient's skin. In some embodiments, the fingertip regions of the index finger region and/or the middle finger region and/or the thumb region of the glove of the present invention are of reduced or smaller circumference and diameter, thus ensuring the glove material is pulled tightly over the fingertips and ensuring that there is very little if any excess glove material that can interfere with the user finding a faint pulse on a patient or performing other tasks. Some or all of the fingertip regions of the fingers regions (index, middle, ring, and little) and thumb region may be smooth (un-textured or unpatterned) or differently patterned or of a reduced or smaller circumference/diameter in the manner described herein.

In one aspect, the disclosure may provide a glove comprising a wrist region; a palm region extending outwardly from the wrist region; a digit region extending outwardly from the palm region; a hand-receiving cavity defined by the wrist region, palm region and digit region, and an opening to said cavity being defined by the wrist region, said cavity being adapted to receive a hand of a user inserted through the opening; and wherein the wrist region, palm region and digit region may be comprised of nitrile rubber that is free of or essentially free of zinc and/or sulfur and/or accelerators.

In another aspect, the disclosure may provide a glove comprising a wrist region; a palm region extending outwardly from the wrist region; a digit region extending outwardly from the palm region, said digit region including an index finger region and middle finger region; a hand-receiving cavity defined by the wrist region, palm region and digit region, and an opening to said cavity being defined by the wrist region, said cavity being adapted to receive a hand of a user inserted through the opening; and wherein the wrist region, palm region and digit region may be comprised of nitrile rubber that is free of or essentially free of one or more of zinc and/or sulfur and/or accelerators, and wherein the digit region and palm region may be textured except for a section of a front surface of one or both of the index finger region and the middle finger region and the section is located adjacent a tip of the associated index finger region and the middle finger region and extends for a distance downwardly therefrom and towards the palm region. The term "front section" should be understood to be that part of the index finger region or middle finger region that is adjacent the uppermost pad on the user's index or middle finger; where that uppermost pad is used to touch objects and is highly sensitive to the touch.

In another aspect, the disclosure may provide a glove comprising a wrist region; a palm region extending outwardly from the wrist region; a digit region extending outwardly from the palm region and comprising an index finger region, a middle finger region, a ring finger region, and little finger region and a thumb region; a hand-receiving cavity defined by the wrist region, palm region and digit region, and an opening to said cavity being defined by the wrist region, said cavity being adapted to receive a hand of a user inserted through the opening; and wherein the wrist region, palm region and digit region may be comprised of nitrile rubber that is free of or essentially free of sulfur and one or more of the index finger region, middle finger region, ring finger region, little finger region and thumb region includes a band region adapted to be located proximate one or more of a user's finger knuckles; and the band region comprises alternating ridges and valley's formed in the material of the glove.

In yet another aspect, the glove may provide a wrist region; a palm region extending outwardly from the wrist region; a thumb region, an index finger region, a middle finger region, a ring finger region and a little finger region all extending outwardly from the palm region and each having a fingertip region that extends from proximate a tip thereof to proximate where a first knuckle of a user's thumb or finger will be located when the glove is worn; wherein the fingertip region of the index finger region is of a first circumference and a first diameter; and wherein a remaining portion of the index finger region from the fingertip region thereof to the palm region is of a second circumference and a second diameter; and wherein the first circumference is smaller than the second circumference and the first diameter is smaller than the second diameter; and wherein the first circumference and first diameter of the fingertip region of the index finger region may be of a size that causes the fingertip region of the index finger region to tend to be pulled taut or tightly around a tip of a person's index finger when the glove is worn and applies pressure thereto.

In a further aspect, the disclosure may provide a method of using a glove for performing a medical procedure, said method comprising: providing a glove comprising: a wrist region; a palm region extending outwardly from the wrist region; a thumb region, an index finger region, a middle finger region, a ring finger region and a little finger region all extending outwardly from the palm region and each having a fingertip region that extends from proximate a tip thereof to proximate where a first knuckle of a user's thumb or finger will be located when the glove is worn; wherein the fingertip region of the index finger region is of a first circumference and a first diameter; and wherein a remaining portion of the index finger region from the fingertip region thereof to the palm region is of a second circumference and a second diameter; and wherein the first circumference is smaller than the second circumference and the first diameter is smaller than the second diameter; inserting a user's hand into the glove; said step of inserting including inserting the user's index finger into the index finger region of the glove; pulling material of the fingertip region of the index finger region tightly over the tip of user's index finger; applying pressure to the tip of the user's index finger as the material is pulled tightly over the tip of the user's index finger; placing the tip of the user's index finger on a pulse point of a patient's body and detecting the patient's blood pressure through the fingertip region of the index finger region of the glove.

In another aspect, the disclosure may provide a glove comprising a wrist region; a palm region extending outwardly from the wrist region; a thumb region, an index finger region, a middle finger region, a ring finger region and a little finger region all extending outwardly from the palm region and each having a fingertip region that extends from proximate a tip thereof to proximate where a first knuckle of a user's thumb or finger will be located when the glove is worn; and wherein the fingertip region of each of the thumb region, the index finger region, the middle finger region, the ring finger region, and the little finger region has a front surface adapted to be located adjacent a front of a user's thumb and fingers; and a back surface adapted to be located adjacent a back of the user's thumb and fingers; and wherein the front surfaces of the fingertip regions of one or more of the thumb region, the index finger region and the middle finger region are free of texture and some or all of a rest of the glove including the fingertip regions of the ring finger region and little finger region are textured.

Furthermore, in another aspect, the disclosure may provide a glove comprising a wrist region; a palm region extending outwardly from the wrist region; a thumb region, an index finger region, a middle finger region, a ring finger region and a little finger region all extending outwardly from the palm region and each having a fingertip region that extends from proximate a tip thereof to proximate where a first knuckle of a user's thumb or finger will be located when the glove is worn; and wherein the fingertip region of each of the thumb region, the index finger region, the middle finger region, the ring finger region, and the little finger region has a front surface adapted to be located adjacent a front of a user's thumb and fingers; and a back surface adapted to be located adjacent a back of the user's thumb and fingers; and wherein the front surfaces of the fingertip regions of one or more of the thumb region, the index finger region and the middle finger region are provided with a first texture; and some or all of a rest of the glove including the fingertip regions of the ring finger region and little finger region are provided with a second texture.

In another aspect, the present disclosure may provide a glove comprising a wrist region; a palm region extending outwardly from the wrist region; a thumb region, an index finger region, a middle finger region, a ring finger region and a little finger region all extending outwardly from the palm region and each having a fingertip region that extends from proximate a tip thereof to proximate where a first knuckle of a user's thumb or finger will be located when the glove is worn; and a remaining portion that extends from a lower end of the fingertip region to the palm region; wherein at least a front surface of the fingertip region of one or more of the thumb region, the index finger region, the middle finger region, the ring finger region, and the little finger is provided with a first texture and an associated remaining portion of the one or more of the thumb region, the index finger region, the middle finger region, the ring finger region, and the little finger is provided with a second texture.

In another aspect, the present disclosure may provide a glove comprising a wrist region; a palm region extending outwardly from the wrist region; a thumb region, an index finger region, a middle finger region, a ring finger region and a little finger region all extending outwardly from the palm region and each having a fingertip region that extends from proximate a tip thereof to proximate where a first knuckle of a user's thumb or finger will be located when the glove is worn; and a remaining portion that extends from a lower end of the fingertip region to the palm region; wherein at least a front surface of the fingertip region of one or more of the thumb region, the index finger region, the middle finger region, the ring finger region, and the little finger is provided with a first texture and an associated remaining portion of the one or more of the thumb region, the index finger region, the middle finger region, the ring finger region, and the little finger is free of texture.

In another aspect, the present disclosure may provide a glove comprising a wrist region; a palm region extending outwardly from the wrist region; a thumb region, an index finger region, a middle finger region, a ring finger region and a little finger region all extending outwardly from the palm region and each having a fingertip region that extends from proximate a tip thereof to proximate where a first knuckle of a user's thumb or finger will be located when the glove is worn; and a remaining portion that extends from a lower end of the fingertip region to the palm region; wherein at least a front surface of the fingertip region of the index finger region is provided with a first texture and wherein the remaining portion of the index finger region is provided with a second texture.

In yet another aspect, the present disclosure may provide a glove comprising a wrist region; a palm region extending outwardly from the wrist region; a thumb region, an index finger region, a middle finger region, a ring finger region and a little finger region all extending outwardly from the palm region and each having a fingertip region that extends from proximate a tip thereof to proximate where a first knuckle of a user's thumb or finger will be located when the glove is worn; and a remaining portion that extends from a lower end of the fingertip region to the palm region; wherein at least a front surface of the fingertip region of the index finger region is provided with a first texture and wherein the remaining portion of the index finger region is free of texture.

In another aspect, the present disclosure may provide a glove comprising a wrist region; a palm region extending outwardly from the wrist region; a thumb region, an index finger region, a middle finger region, a ring finger region and a little finger region all extending outwardly from the palm region; a fingertip region and a remaining portion provided on each of the thumb region, the index finger region, the middle finger region, the ring finger region, and the little finger region, wherein the fingertip region extends from proximate a tip to proximate where a first knuckle of a user's thumb or respective finger will be located when the glove is worn; and wherein the remaining portion extends from a lower end of the fingertip region to the palm region; and wherein at least one of the fingertip regions is of a reduced circumference relative to a circumference of the associated remaining portion.

In another aspect, the present disclosure may provide a glove comprising a wrist region; a palm region extending outwardly from the wrist region; a thumb region, an index finger region, a middle finger region, a ring finger region and a little finger region all extending outwardly from the palm region; wherein the glove is fabricated with an exterior surface thereof being of a first color and an interior surface thereof being of a second color, where the first color contrasts with the second color; and wherein the first color and the second color are a tear indicator when the glove is one of cut, ripped and torn; and a cuff provided at an end of the wrist region; wherein the cuff comprises a portion of the wrist region that is one of rolled and folded back upon itself; wherein the cuff is of the second color and a rest of the wrist region is of the first color. As by way of an example only, the first color may be white and the second color may be blue.

In yet another aspect, the present disclosure may provide a glove comprising a wrist region; a palm region extending outwardly from the wrist region; a thumb region, an index finger region, a middle finger region, a ring finger region and a little finger region all extending outwardly from the palm region; a fingertip region and a remaining portion provided on each of the thumb region, index finger region, middle finger region, ring finger region, and little finger region, wherein the fingertip region extends from proximate a tip to proximate where a first knuckle of one of a user's thumb and respective finger will be located when the glove is worn; and wherein the remaining portion extends from a lower end of the fingertip region to the palm region; and wherein at least one of the fingertip regions of the thumb region, the index finger region, the middle finger region, the ring finger region, and the little finger region is of a bullet-tip configuration.

In another aspect, the present disclosure may provide a glove comprising a wrist region; a palm region extending outwardly from the wrist region; a thumb region, an index finger region, a middle finger region, a ring finger region and a little finger region all extending outwardly from the palm region; a fingertip region and a remaining portion provided on each of the thumb region, the index finger region, the middle finger region, the ring finger region, and the little finger region, wherein the fingertip region extends from proximate a tip to proximate where a first knuckle of one of a user's thumb and respective finger will be located when the glove is worn; and wherein the remaining portion extends from a lower end of the fingertip region to the palm region; and wherein the fingertip regions of one or more of the thumb region, the index finger region, and the middle finger region has an appearance that is different from a rest of the glove.

In another aspect, the present disclosure may provide a glove comprising a wrist region; a palm region extending outwardly from the wrist region; a thumb region, an index finger region, a middle finger region, a ring finger region and a little finger region all extending outwardly from the palm region; wherein each of the thumb region, the index finger region, the middle finger region, the ring finger region, and the little finger region has a length measured from a tip thereof to the palm region; wherein at least one of the thumb region, the index finger region, the middle finger region, the ring finger region, and the little finger region is reduced in length.

BRIEF DESCRIPTION OF THE SEVERAL VIEWS OF THE DRAWINGS

An exemplary glove in accordance with an aspect of the present disclosure is set forth in the following description, is shown in the drawings and is particularly and distinctly pointed out and set forth in the appended claims.

FIG. 5 is a cross-sectional view of the glove taken on line 5-5 of FIG. 4;

FIG. 6 is a cross-sectional view similar to FIG. 5 but showing additional layers of the glove;

FIG. 29E is a side elevational view of the fingertip region similar to FIG. 29B except the fingertip region includes two fluted regions that are located side-by-side;

FIG. 29F is a side elevational view of the fingertip region similar to FIG. 29B except the fingertip regions includes a plurality of fluted regions that are horizontally oriented with respect to a longitudinal axis of the finger region; and FIG. 29G is a cross-section of the fingertip region of FIG. 29F taken along line 29G-29G thereof.

Similar numbers refer to similar parts throughout the drawings.

DETAILED DESCRIPTION

Figure 1:
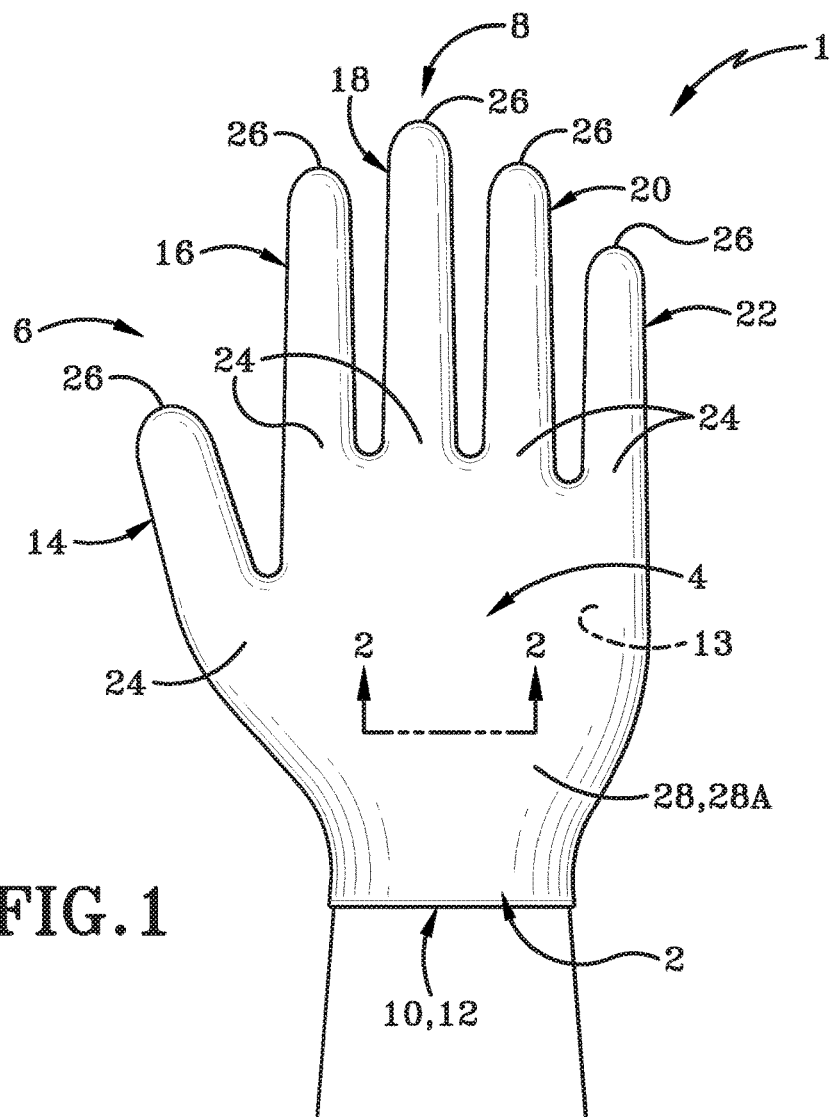
FIG. 1 is a front elevational view of a first embodiment of a glove in accordance with an aspect of the disclosure; where the glove is an ambidextrous glove and wherein a rear elevation view of the ambidextrous glove will be a mirror image of the glove shown in FIG. 1.

FIG. 1 shows a sample embodiment of an ambidextrous glove generally indicated at 1. Glove 1 includes a wrist region 2, a palm region 4, and a digit region 6. Glove 1 has a top 8 and a bottom 10 with a bottom entrance opening 12 of a hand-receiving cavity 12. Entrance opening 12 is at bottom 10 and serves to allow a user to insert his or her hand therethrough and into cavity 12. Entrance opening 12 is defined by wrist region 2. Cavity 12 extends from adjacent bottom 10 to adjacent top 8.

Digit region 6 includes five finger regions comprising a thumb region 14, an index region 16, a middle finger region 18, a ring finger region 20, and a little finger region 22. Each of the finger regions 14-22 has a base 24 and a tip 25. Each of the finger regions at its respective base 24 is secured to palm region 4 and extends upwardly and outwardly therefrom to the respective tip 25. Glove 1 has an exterior surface 28 and an interior surface 30.

Figure 2:
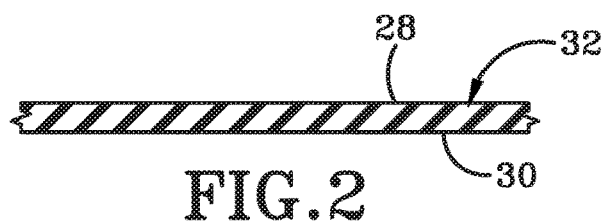
FIG. 2 is a cross-section of the front of the ambidextrous glove taken on line 2-2 of FIG. 1.
Figure 3:
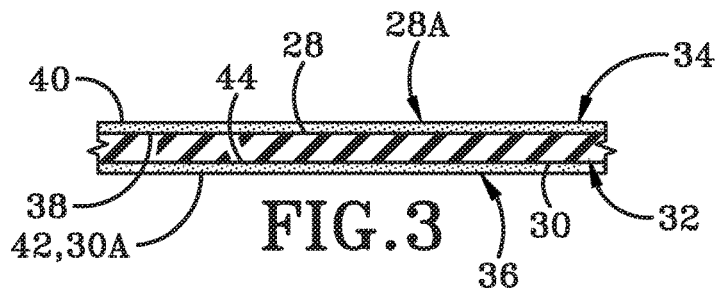
FIG. 3 is a cross-section of the front of the ambidextrous glove similar to FIG. 2 except showing an embodiment of the glove that includes additional layers in the glove.

Glove 1 may include a single first layer 32 as shown in FIG. 2, or a plurality of layers, such as layers 32, 34 and 36 as shown in FIG. 3. Where the single layer 32 is used, as shown in FIG. 2, exterior surface 28 of glove 1 is also the exterior surface of layer 32, and interior surface 30 of glove 1 is also the interior surface of layer 32.

Glove 1 may include one or more additional layers that make up the glove. FIG. 3 shows two additional layers used to form glove 1. In this particular example of a glove 1 with two additional layers, a second or intermediate layer 34 has interior and exterior surfaces 38 and 40, and an exterior or third layer 36 has interior and exterior surfaces 42 and 44. Interior surface 38 of layer 34 may be in contact with and secured to exterior surface 28 of first layer 32, while interior surface 42 of third layer 36 may be in contact with and secured to exterior surface 40 of second layer 34. Thus, exterior surface 44 of layer 36 serves as the exterior surface 28A of glove 1 when formed of these three layers. Interior surface 30 in either case defines cavity 12 and extends from adjacent bottom 10 to adjacent top 8 and serves as the interior surface of wrist region 2, palm region 4 and each of the finger regions 14-22. Glove 1 may comprise one, two, three, or more layers, as will be understood by those skilled in the art.

Where the single layer 32 is used, as shown in FIG. 2, exterior surface 28 extends from adjacent bottom 10 to adjacent top 8 and serves as the exterior surface of wrist region 2, palm region 4 and finger regions 14-22. Where the three layers are used as shown in FIG. 3, exterior surface 44 or 28A extends from adjacent bottom 10 to adjacent top 8 and serves as the exterior surface of wrist region 2, palm region 4, and finger regions 14-22.

Layer 32 may be formed of nitrile rubber. In particular, layer 32 may be formed of a nitrile rubber that is free of or essentially free of zinc and/or sulfur and/or accelerators. Thus, each of exterior and interior surfaces 28 and 30 may be free of these same components and compounds, thereby providing a glove that reduces or essentially eliminates, in users, hypersensitivity, or allergic reactions to compounds such as the zinc and/or sulfur and/or accelerators. It will be understood that people may have hypersensitivity to other compounds that may be used on occasion in nitrile gloves. It will be understood that the nitrile gloves in accordance with an aspect of the present disclosure may be free of or essentially free of compounds that cause hypersensitivity or allergic reactions in users who wear the glove 1.

In the case of glove 1 which includes more than one layer; layer 32 may likewise be formed of this same nitrile rubber that is free zinc and/or sulfur and/or accelerators. Layers 34 and 36 may be formed of various types of polymers that are typically elastomeric polymers that are different from layer 32 and which may be the same as or different from one another. Thus, the elastomeric polymer of any of the additional layers may have a different composition to the nitrile rubber used in the first layer. The layers other than interior layer 32 may be formed of polymers that may or may not include zinc and/or sulfur and/or an accelerator. The use of an additional polymer layer or layers to define exterior surface 28A thus may provide a multilayer glove that essentially eliminates the allergic reaction to compounds such as the zinc and/or sulfur and/or accelerators noted above for a person having hypersensitivity to such elements or compounds. This may be true even if the exterior layer or surface includes zinc and/or sulfur and/or an accelerator because allergic reactions of this nature are most commonly caused by prolonged contact with the allergen such as when a person wears the glove for an extended period so that contact of the wearer's hand and the interior layer/surface of the glove is the primary concern related to producing allergic reactions.

Figure 4:
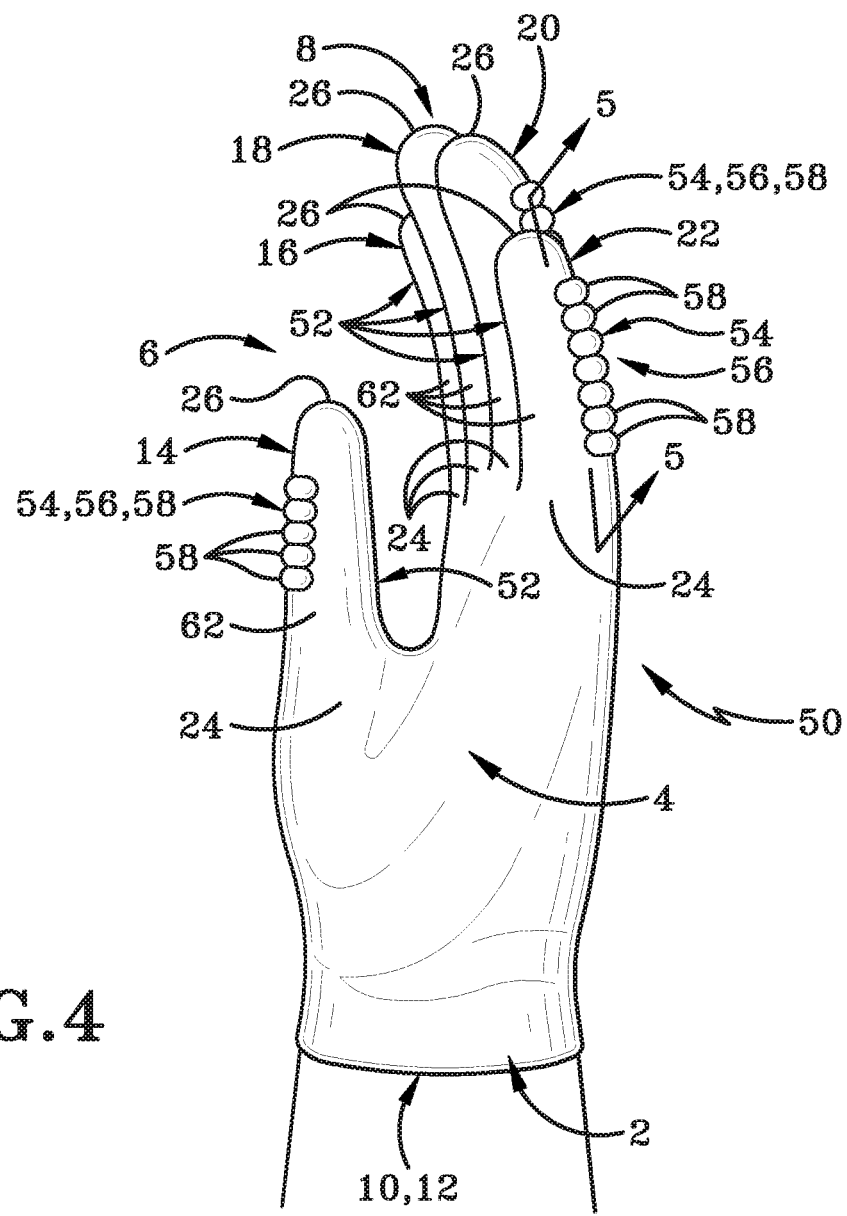
FIG. 4 is a side elevational view of a second embodiment of the glove in accordance with the present disclosure showing a hand-specific glove for a right hand; wherein the left handed glove will be a mirror image hereof; and wherein the glove includes a plurality of band regions formed in the digit regions.

Referring now to FIG. 4, a glove 50 is shown that is a hand-specific glove. In particular, FIG. 4 shows a right-handed glove although it will be understood that FIG. 4 should likewise represent a left-handed glove inasmuch as a left-handed glove is a mirror image of that shown in FIG. 4. Thus, unlike the ambidextrous glove 1 shown in FIG. 1 in which all of the finger regions including thumb region 14 are aligned along or intersected by a common plane, glove 50 is configured such that the four finger regions 16, 18, 20 and 22 may be aligned along a common plane whereas thumb region 14 is spaced from said plane. Aside from the fact that glove 50 is a hand-specific glove, it is nonetheless similar to glove 1 in that it includes a wrist region 2, a palm region 4, and a digit region 6 which includes five finger regions comprising a thumb region 14, index finger region 16, middle finger region 18, ring finger region 20 and little finger region 22. FIG. 4 also shows that each of the finger regions 14-22 has a base 24 and a tip 25 and is secured to palm region 4 as described with respect to glove 1. Each of finger regions 14-22 has a finger front 52 and a finger back 54. It is noted that the finger fronts 52 of finger regions 16-22 generally face in the same direction and that the finger backs 54 of finger regions 16-22 face generally in the same direction and the opposite direction as finger fronts 52 thereof. On the other hand, the finger front 52 of thumb region 14 faces in a different direction than that of the finger fronts 52 of the index, middle, ring and the little finger regions 16-22 and the finger back 54 of thumb region 14 likewise faces in a different direction than that of finger backs 54 of finger regions 16-22.

One or more of each of finger regions 14-22 along the finger back 54 thereof may include a band region 56 including a plurality of band segments 58 that include respective elastomeric bands 60. Each band region 56 also includes a plurality of trough segments 64 between each adjacent pair of band segments 58. In the sample embodiment, the top of the band region 58 of a given finger region may be spaced downwardly a distance from the tip 25 of the given finger region, for instance, about ½ or ¾ inch to about ¾, 1 or 1¼ inch and therefore may be positioned between a tip of the user's finger and the user's first knuckle in that finger. The bottom of each band region 58 may be located so that the bottom is located between the user's palm and lowermost knuckle on that particular finger or thumb (obviously only one knuckle is located on the thumb and the band region 58 associated therewith will originate between the tip and the knuckle and the bottom of the band region will fall between the user's palm and knuckle on the thumb. Each finger region 14-22 is formed of a peripheral wall 62 that defines the respective finger front and back 52 and 54, including the respective band region 56 of band segments 58 and trough segments 64.

With reference to FIGS. 5 and 6, band region 56 is described in this paragraph as viewed in a section view taken parallel to the longitudinal axis of the given finger region. Each band segment 58 has a concavely curved interior surface 66 and a convexly curved exterior surface 68 such that surfaces 66 and 68 extend from adjacent the top of the given band segment 58 to adjacent the bottom of the given band segment 58. Interior surface 66 faces the longitudinal axis of the given finger region and the portion of cavity 12 defined by the given finger region while exterior surface 68 faces away from the longitudinal axis of the given finger region and the portion of cavity 12 defined by the given finger region. For a given pair of adjacent band segments 58, the top of the lower band segment (including its surfaces 66 and 68) is adjacent the trough segment 64 between the given adjacent pair and the bottom of the higher band segment (including its surfaces 66 and 68), which is also adjacent the trough segment 64 between the given adjacent pair. Each band 60 has a convexly curved exterior surface 70 and an interior surface 72. Each of surfaces 70 and 72 extend from adjacent the top of the given band 60 to the bottom of the given band 60. Interior surface 72 faces the longitudinal axis of the given finger region and the portion of cavity 12 defined by the given finger region while exterior surface 70 faces away from the longitudinal axis of the given finger region and the portion of cavity 12 defined by the given finger region. Exterior surface 70 of a given band is in contact with and secured to the interior surface 66 of a given band segment 58.

Each band 60 is curved as viewed from above or parallel to the longitudinal axis of the given finger region so that interior surface 72 is concavely curved and exterior surface 70 is convexly curved as so viewed. Each band 60 is thus configured to partially wrap around the back of a given finger of a person wearing glove 50 with the given interior surface 72 contacting the back of the given finger. This configuration helps prevent glove 50 from sliding off of the person's hand, especially when worn over an extended period of time. Each band 60 in the sample embodiment extends only along the finger back 54 of a given finger region, and thus no portion of band 60 extends along the finger front 52 of the given finger region. The band regions 58 stretch or elongate when the user bend their finger regions 14-22 and elastically returns to the region's original configuration when the finger region 14-22 is straightened. Band regions 58 aid in reducing the forces applied to the finger regions 14-22 and thus tend to reduce the degree to which the finger regions may stretch over time.

As with the multilayer version of glove 1 in FIG. 3, where additional layers are used for glove 50 as shown in FIG. 6, the second or intermediate layer 34 has interior and exterior surfaces 38 and 40, and the exterior or third layer 36 has interior and exterior surfaces 42 and 44. Interior surface 38 of layer 34 is in contact with and secured to exterior surface 28 of first layer 32, while interior surface 42 of third layer 36 is in contact with and secured to exterior surface 40 of second layer 34. Thus, exterior surface 44 of layer 36 serves as the exterior surface 28A of glove 50 when formed of these three layers. Interior surface 30 in either case defines cavity 12 and extends from adjacent bottom 10 to adjacent top 8 and serves as the interior surface of wrist region 2, palm region 4 and each of the finger regions 14-22. Where the single layer 32 is used as shown in FIG. 2, exterior surface 28 extends from adjacent bottom 10 to adjacent top 8 and serves as the exterior surface of wrist region 2, palm region 4, and finger regions 14-22. Where the three layers are used as shown in FIG. 3, exterior surface 44 or 28A extends from adjacent bottom 10 to adjacent top 8 and serves as the exterior surface of wrist region 2, palm region 4, and finger regions 14-22.

Peripheral wall 62 is formed entirely from layer 32 in a single layer version of glove 50 (FIGS. 4, 5) and may be formed by a plurality of layers, such as layers 32, 34 and 36 in a multilayer version of glove 50 (FIGS. 4, 6). Thus, for the single layer version or multilayer version, interior surface 30 includes a finger region interior surface or peripheral wall interior surface 74 of a given finger region 14-22 or peripheral wall 62. For the single layer version, exterior surface 28 includes a finger region exterior surface or peripheral wall exterior surface 76 of a given finger region 14-22 or peripheral wall 62. For the multilayer version, exterior surface 28A/44 includes a finger region exterior surface or peripheral wall exterior surface 76 of a given finger region 14-22 or peripheral wall 62.

Layers 32, 34 and 36 of glove 50 are formed of the same materials as noted above with respect to glove 1, and each band 60 is formed of a nitrile rubber that is free of or essentially free of zinc and/or sulfur and/or accelerators. Thus, layer 32 and bands 60 provide the same hypoallergenic qualities noted above.

Figure 7:
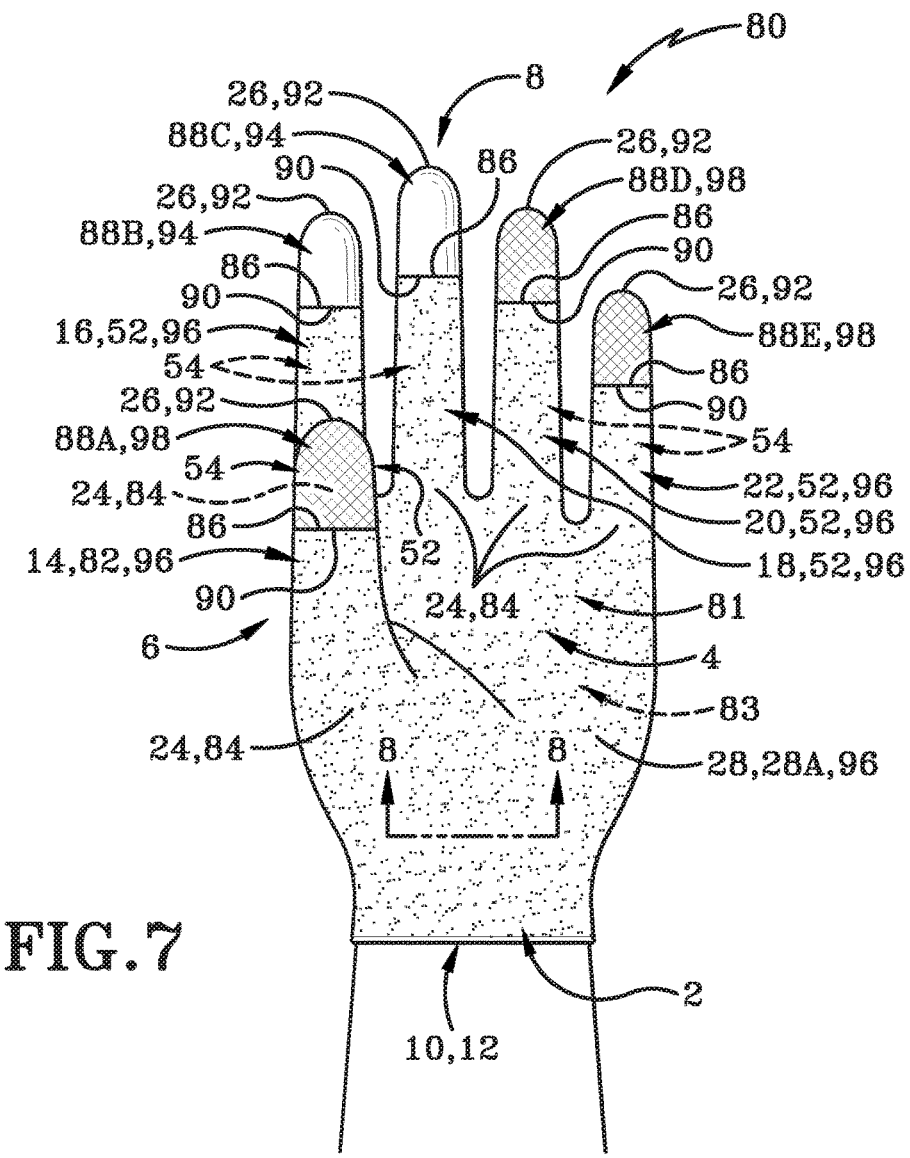
FIG. 7 is a front elevational view a third embodiment of a glove in accordance with an aspect of the disclosure; where the glove illustrated is a hand-specific glove for a user's left-hand; wherein a right hand hand-specific glove would be a mirror image hereof; and wherein the figure shows texturing on the palm and digit regions but not on the front surfaces of fingertip regions on the index finger region and the middle finger region.

Referring now to FIG. 7, a glove 80 is shown that is a hand-specific glove. In particular, FIG. 7 shows a left-handed glove although it will be understood that FIG. 7 should likewise represent a right-handed glove inasmuch as a right-handed glove is a mirror image of that shown in FIG. 7. Thus, glove 80 is configured such that the four finger regions 16, 18, 20 and 22 may be aligned along a common plane whereas thumb region 14 is spaced from said plane. Glove 80 includes a wrist region 2, a palm region 4, and a digit region 6 that includes five finger regions comprising a thumb region 14, index finger region 16, middle finger region 18, ring finger region 20 and little finger region 22. FIG. 7 also shows that each of finger regions 14-22 has a base 24 and a tip 25 and is secured to palm region 4 as described with respect to glove 1. Glove 80 has a front or front side 81 (or palm side) and a back or back side 83.

Each of finger regions 14-22 has a finger front 52 and a finger back 54. The finger fronts 52 of finger regions 16-22 generally face in the same direction and that the finger backs 54 of finger regions 16-22 face generally in the same direction and the opposite direction as finger fronts 52 thereof. On the other hand, the finger front 52 of thumb region 14 faces in a different direction than that of the finger fronts 52 of the index, middle, ring and the little finger regions 16-22 and the finger back 54 of thumb region 14 likewise faces in a different direction than that of finger backs 54 of finger regions 16-22. Each finger region 14-22 is formed of a peripheral wall 62 that defines the respective finger front and back 52 and 54.

Each of finger regions 14-22 has a finger base region 82 having a bottom 84 adjacent the respective base 24 and a top 86. Each of finger regions 14-22 has a fingertip region 88 that extends upwardly from the corresponding base region 82 to adjacent the corresponding tip 25. Each fingertip region 88 has a bottom 90 at or adjacent the corresponding top 86 and a top 92 at or adjacent the corresponding tip 25. Fingertip regions 88 may include fingertip region 88A of thumb region 14, fingertip region 88B of index finger region 16, fingertip region 88C of middle finger region 18, fingertip region 88D of ring finger region 20, and fingertip region 88E of little finger region 22.

In the sample embodiment, the fingertip region bottom 90 and finger base top 86 of a given finger region 14-22 is spaced downwardly a distance from the fingertip region top 92 and tip 25 of the given finger region, for instance, about ½ or ¾ inch to about ¾, 1 or 1¼ inch. Thus, each fingertip region 88 may have a height from bottom 90 to top 92 of about ½ or ¾ inch to about ½, 1, or 1¼ inch. Each finger base region 82 and fingertip region typically extends along the finger front 52 of the given finger region and may also extend along the corresponding finger back 54.

Whereas gloves 1 and 50 typically have an exterior surface that is smooth in its entirety, glove 80 may have an exterior surface that may have smooth portions and textured portions. In the sample embodiment, the exterior surface of glove 80 has one or more smooth exterior surfaces 94, one or more lighter textured exterior surfaces 96 that are coarser than smooth surface 94, and one or more even coarser textured exterior surfaces 98 that are coarser than smooth surface 94 and lighter textured surface 96. Fingertip region 88B of index finger region 16 and fingertip region 88C of middle finger region 18 may have smooth exterior surfaces 94 that extend from adjacent the corresponding bottom 90 to adjacent the corresponding top 92. Bottom 90 is located in a region that may be approximately positioned adjacent a front of the first knuckle on a user's hand. Smooth surface 94 extends from top 92 of index finger region 52 and middle finger region 54 downwardly for approximately a third of the total length of index finger region 52 and middle finger region 54. (The length will be understood to extend from the tip of any particular finger region to the palm region of the glove.) Smooth surface 94 may be confined to extend only along the given finger front 52 or may also extend along the given finger back 54.

Fingertip region 88A of thumb region 14, fingertip region 88D of ring finger region 20 and fingertip region 88E of little finger region 22 may have coarser textured exterior surfaces 98 that extend from adjacent the corresponding bottom 90 to adjacent the corresponding top 92. Coarser textured surface 98 may be confined to extend only along the given finger front 52 or may also extend along the given finger back 54.

The finger base region 82 of each of thumb region 14, index finger region 16, middle finger region 18, ring finger region 20 and little finger region 22 may have lighter textured exterior surfaces 96 that extend from adjacent the corresponding bottom 84 to adjacent the corresponding top 86. Lighter textured surface 96 may be confined to extend only along the given finger front 52 or may also extend along the given finger back 54.

Wrist region 2 and palm region 4 may have lightly textured exterior surfaces 96 that extend only along front side 81 of glove 80 or which may also extend along back side 83. Lightly textured exterior surface 96 may extend along the entirety of wrist region 2 along front side 81 and may extend along the entirety of wrist region 2 along back side 83. Lightly textured exterior surface 96 may extend along the entirety of palm region 4 along front side 81 and may extend along the entirety of palm region 4 along back side 83. Typically, lightly textured exterior surface 96 extends from adjacent the top of wrist region 2 to adjacent the base 24 of each of finger regions 14-22 along front side 81.

Figure 8:
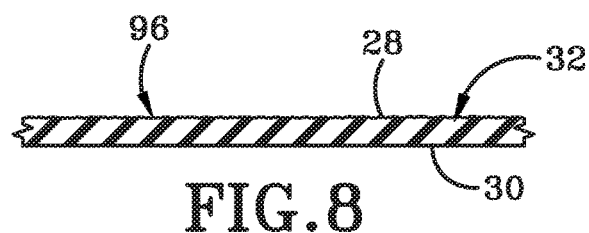
FIG. 8 is a cross-sectional view of the glove taken along line 8-8 of FIG. 7.
Figure 9:
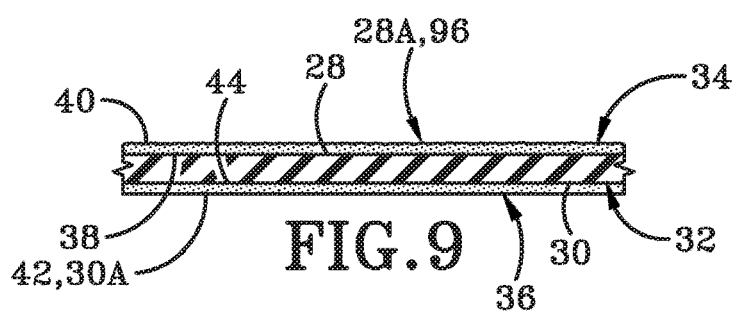
FIG. 9 is a cross-sectional view of the glove similar to FIG. 8 showing additional layers of the glove.

As with the multilayer version of glove 1 in FIG. 3 and glove 50 in FIG. 6, where additional layers are used for glove 80 as shown in FIG. 9, the second or intermediate layer 34 has interior and exterior surfaces 38 and 40, and the exterior or third layer 36 has interior and exterior surfaces 42 and 44. Interior surface 38 of layer 34 is in contact with and secured to exterior surface 28 of first layer 32, while interior surface 42 of third layer 36 is in contact with and secured to exterior surface 40 of second layer 34. Thus, exterior surface 44 of layer 36 serves as the exterior surface 28A of glove 80 when formed of these three layers. Interior surface 30 in either case defines cavity 12 and extends from adjacent bottom 10 to adjacent top 8 and serves as the interior surface of wrist region 2, palm region 4 and each of the finger regions 14-22. Where the single layer 32 is used as shown in FIG. 8, exterior surface 28 extends from adjacent bottom 10 to adjacent top 8 and serves as the exterior surface of wrist region 2, palm region 4, and finger regions 14-22. Where the three layers are used as shown in FIG. 9, exterior surface 44 or 28A extends from adjacent bottom 10 to adjacent top 8 and serves as the exterior surface of wrist region 2, palm region 4, and finger regions 14-22.

Peripheral wall 62 is formed entirely from layer 32 in a single layer version of glove 80 (FIGS. 7, 8) and may be formed by a plurality of layers, such as layers 32, 34 and 36 in a multilayer version of glove 80 (FIGS. 7, 9). Exterior surface 28 in the single layer version thus includes the smooth, lighter textured and coarser textured surfaces 94, 96 and 98, whereas exterior surface 28A/44 in the multilayer version includes the smooth, lighter textured and coarser textured surfaces 94, 96 and 98. Layers 32, 34, and 36 of glove 80 are formed of the same materials as noted above with respect to glove 1 so that layer 32 provides the same hypoallergenic qualities noted above. The textured surfaces provided on glove 80 may be provided on regions of glove 80 that will be contacted when an article is gripped when glove 80 is worn by a user. The textured surfaces will, thus, enhance the gripping ability of the user and reduce the tendency for objects to slip when being held by the user when wearing glove 80.

Figure 10:
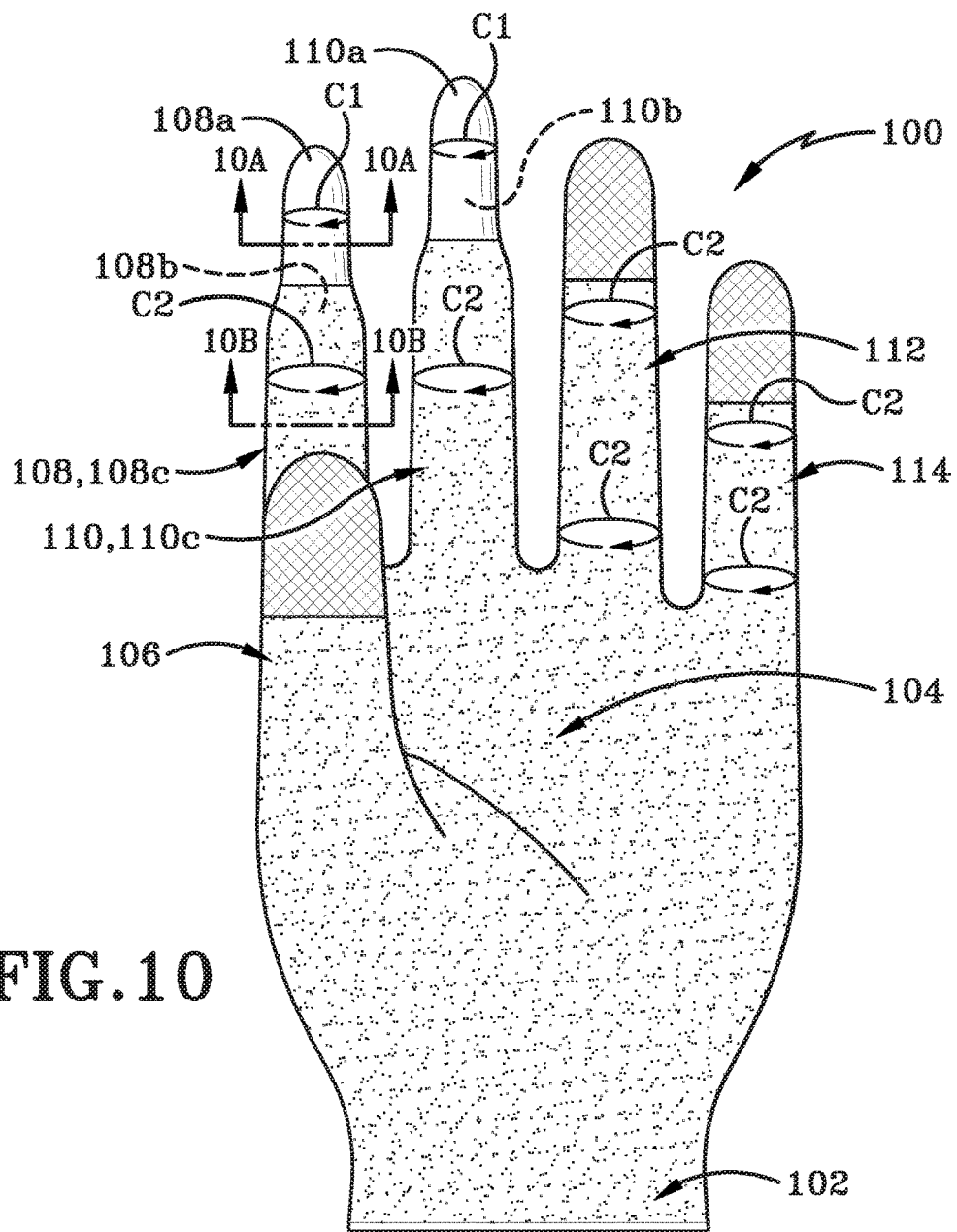
FIG. 10 is a front elevational view of a fourth embodiment of a glove in accordance with an aspect of the present disclosure, where the glove is a hand-specific glove and the fingertip regions of the index and middle finger regions are of a reduced or smaller circumference and diameter.
Figure 10A:
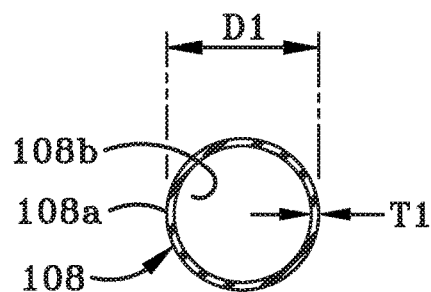
FIG. 10A is a cross-section through the fingertip region of the index finger region of the glove shown in FIG. 10.
Figure 10B:
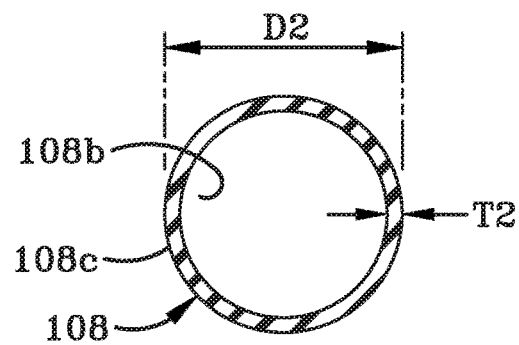
FIG. 10B is a cross-section through a wider portion of the index finger region of the glove of FIG. 10, where the wider portion is located below the fingertip region.

Referring to FIGS. 10-10B there is shown a fourth embodiment of a glove in accordance with an aspect of the disclosure, generally indicated at 100. Glove 100 includes a wrist region 102, a palm region 104, a thumb region 106, an index finger region 108, a middle finger region 110, a ring finger region 112, and a little finger region 114. Glove 100 is illustrated as a hand-specific glove but the same principles as will be discussed hereafter may be incorporated into an ambidextrous glove.

Glove 100 may be substantially identical to any of the gloves 1, 50, or 80 except that at least the fingertip region 108a, 110a of the index finger region 108 and the middle finger region 110 are fabricated to be of a smaller circumference and diameter than are the fingertip regions of the index finger regions and middle finger regions of any of the other glove embodiments disclosed herein. Additionally the fingertip regions 108a, 110a of the index and ring finger regions 108, 110 are of a smaller circumference and diameter than a circumference of the remaining portion of the respective one of the index and middle finger regions 108, 110. The remaining portion of each of these two finger regions is represented by the reference numbers 108c and 110c, respectively in FIG. 10. It should be noted that a step-down region 113 (FIG. 10C) is provided between the circumference of each of the remaining portion 108c, 110c and the associated smaller circumference of the fingertip region 108a, 110a. The step-down region 113 is a region that tapers in circumference from the circumference of the remaining portion 108c, 110c to the smaller or reduced circumference of the associated fingertip region 108a, 110a.

Furthermore, the fingertip regions 108a, 110a are smaller in diameter and circumference than the ring finger region 112, little finger region 114 and thumb region 106 of glove 100. The circumference of the fingertip regions 108a, 110a is measured around an exterior surface of the respective index finger region 108 or middle finger region 110 and in an orientation at right angles to the length of the respective finger region 108 or 110. The length is measured from a tip of the respective finger region down to the palm region 104. The reduced or smaller dimensions (i.e., circumference and diameter) ensure that the glove material in each fingertip region 108a, 110a is pulled tightly around the user's index and middle fingers. The tightly pulled material or film of glove 100 ensures that the user can more easily and readily locate a faint pulse in a patient than if the glove material was only fitted loosely around these two fingertips.

The dimensions of the fingertip region 108a of the index finger region and the fingertip region 110a of the middle finger region 110 may be reduced or smaller by from about 1% up to about 15% relative to the remaining portion of that particular finger region 108 or 110, and to the other finger regions 112, 114 and thumb region 106 in glove 100, or to the finger regions of any of the other embodiments of the glove, and relative to finger regions in prior art gloves. In particular, the fingertip regions 108a and 110a may be reduced or smaller by from about 3% up to about 10% relative to the remaining portion of the associated finger region 108, 110. This reduction in the dimensions of the fingertip regions helps ensure that the glove film/material is stretched to the point that the film/material fits tightly against the user's index and middle fingers. The film needs to be pulled tight enough to ensure that even a faint pulse may be detected through the film but the film should not be stretched so tight that the gloves are restrictive or uncomfortable to wear.

Instead of just the fingertip regions 108a, 110a being of a smaller diameter "D1" and circumference "C1" relative to the fingertip regions of the other finger regions of the gloves disclosed herein, substantially all of the fingertip regions of the finger regions on glove 100 (including the thumb region 106, ring finger region 112 and little finger region 114) may be fabricated to be of a reduced or smaller diameter and circumference relative to the remaining portions of those finger regions. Still further, instead of just the fingertip regions 108a, 110a being of smaller diameter and circumference, the entire index finger region 108 and entire middle finger region 110 may be fabricated to have smaller dimensions relative to the index finger region and middle finger regions of the other embodiments of the glove disclosed herein and relative to the ring finger region 112, little finger region 114 and thumb region 106 of glove 100. In other words, the index finger region 108 and 110 may be of smaller diameter and circumference along substantially the entire length thereof from the palm region to the tip of the respective finger region instead of only being smaller in dimension along the fingertip region 108a or 110a.

Referring to FIGS. 10 and 10A, there is shown a cross-section through fingertip region 108a of index finger region 108. Fingertip region 108a is shown to have a circumference "C1" measured around an exterior surface of the fingertip region 108a; and a diameter "D1". The circumference "C1" is of such a size that when glove 100 is donned, the fingertip region 108a will be smaller than the circumference and diameter of the user's finger that is received in the interior cavity 108b thereof. Because of this reduced or smaller circumference "C1", the film of index finger region 108 may tend to be pulled tightly around the user's finger as the material thereof stretches to allow of the user's index finger to enter into the interior 108b thereof. Because of the stretching of the film of fingertip region 108a to accommodate the user's index finger, the thickness of the wall of fingertip region 108a will be reduced or smaller to a thickness "T1". (A similar situation exists with fingertip region 110a when the user's middle finger is inserted into the interior 110b therein.)

FIG. 10B shows a cross-section through the wider part 108c of the index finger region 108. This wider part 108c is located below the fingertip region 108a. The circumference of the wider part 108c is greater than the circumference "C1" of the fingertip region 108a and is indicated in FIG. 10B as circumference "C2". The wider part 108c is of a diameter "D2" that is greater than the diameter "D1" of fingertip region 108a. The circumference "C2" is of a size that will be greater than the diameter of a user's index finger that will be received into the interior 108b of index finger region 108. The thickness "T2" of the wall of wider part 108c is greater than the thickness "T1" of the wall of fingertip region 108a. The thinner wall thickness "T1" of index finger region 108 ensures that the material of the fingertip region 108a is pulled tighter around the tip of the user's finger than is the material along the rest of the length of the wider part 108b.

FIG. 10 also shows that fingertip region 110a of middle finger region 110 is also of a circumference "C1" and that the rest of middle finger region 110 is of a circumference "C2". Fingertip region 110a of middle finger region 110 is also of a diameter "D1" (FIG. 10A) and the rest of middle finger region 110 is of a diameter "D2" (FIG. 10B). Ring finger region 112 is of a substantially constant circumference "C2" and diameter "D2" along substantially its entire length. Similarly, little finger region 114 is of a substantially constant circumference "C2" and diameter "D2" along substantially its entire length.

It should be noted that the first circumference "C1" and first diameter "D1" of fingertip region 108a of index finger region 108 and fingertip region 110a of middle finger region 110 are of a size that causes the fingertip regions 108a and 110a to be pulled tightly around the tips of a person's index finger and middle finger when the glove is worn. The reduced or smaller diameter "D1" and circumference "C1" of fingertip regions 108a and 110a also is of a size that will result in pressure being applied to the tips of the person's index finger and middle finger. Glove 10 may apply some pressure to the user's hand because of the diameter (and associated circumference) of wrist region 2, palm region 4 and the wider regions ("D2"/"C2") of index finger region 108, middle finger region 110, ring finger region 112 and little finger region 114. However, the smaller dimensions ("D1"/"C1") of fingertip regions 108a, 110a applies even greater pressure to the tips of the user's index finger and middle finger. The degree of pressure applied by fingertip regions 108a, 110a aids in ensuring that the tactile sensitivity of the user's fingers is not lost because the user is wearing a glove.

It will be understood that only one or the other of the fingertip regions 108a, 110a may be fabricated so as to have these reduced or smaller dimensions "D1"/"C1", if that is desired.

Glove 100 may be used while taking a patient's pulse by providing glove 100 that comprises wrist region 102, palm region 104; thumb region 106, index finger region 108, middle finger region 110, ring finger region 112 and little finger region 114; wherein the fingertip region 108a of index finger region 108 is of a first circumference "C1" and a first diameter "D1"; and wherein a remaining portion of the index finger region from below fingertip region 108a to palm region 104 is of a second circumference "C2" and a second diameter "D2"; and wherein the first circumference "C1" is smaller than the second circumference "C2" and the first diameter "D1" is smaller than the second diameter "D2"; inserting a user's hand into glove 100; said step of inserting including inserting the user's index finger into index finger region 108 of glove 100; pulling material of fingertip region 108a of index finger region 108 tightly over the tip of user's index finger; applying (inwardly directed) pressure to the tip of the user's index finger as the material of glove 100 is pulled tightly over the tip of the user's index finger; placing the tip of the user's index finger on a pulse point of a patient's body and detecting the patient's blood pressure through the fingertip region 108a of the index finger region 108 of glove 100. A similar pressure may be applied to the user's middle finger by fingertip region 110a where fingertip region 110a is similarly dimensioned to fingertip region 108a.

Figure 10C:
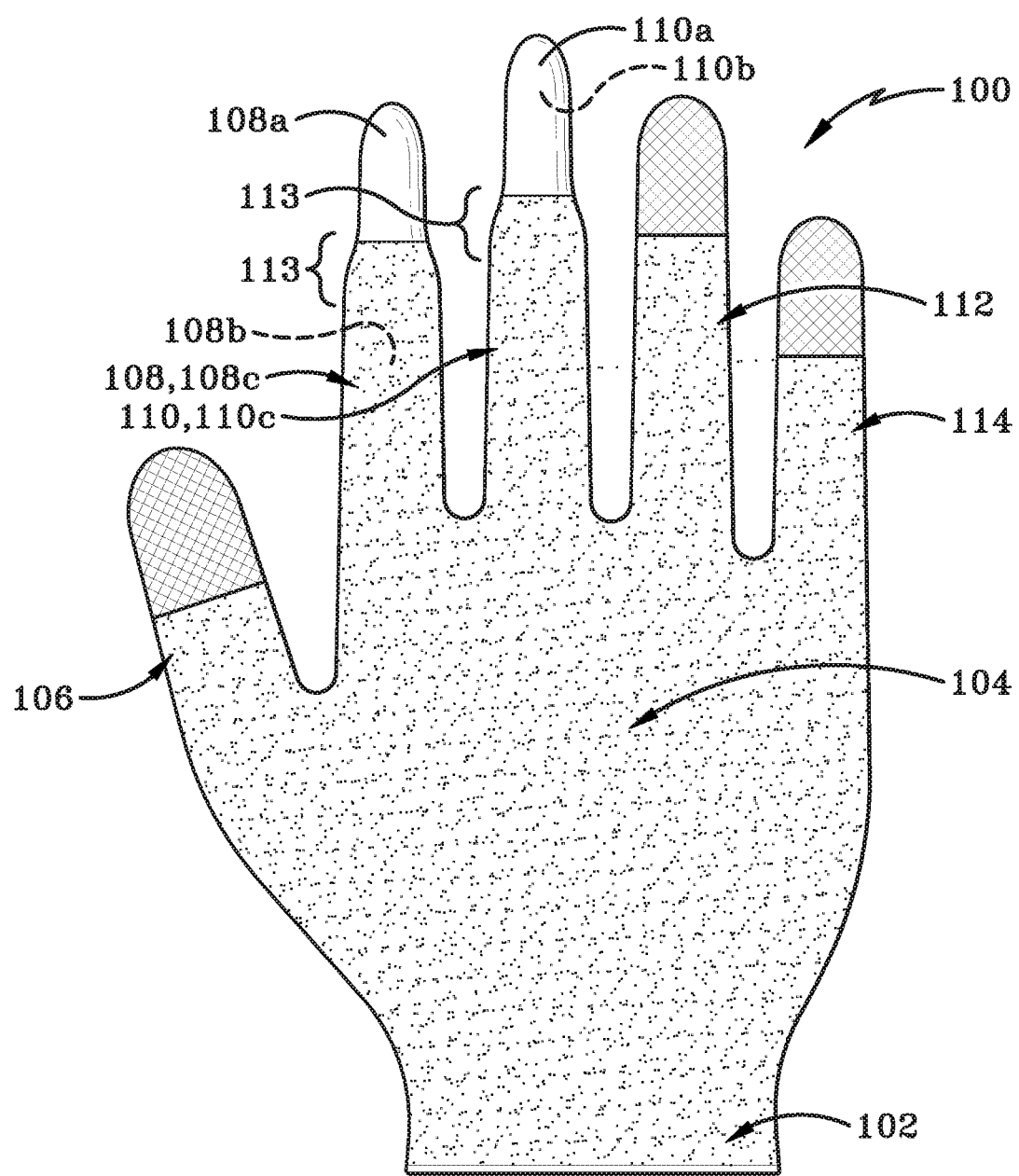
FIG. 10C is a front elevation view of the fourth embodiment of the glove shown as an ambidextrous glove.

FIG. 10 shows that fingertip regions 108a, 110a are smooth or free of texture, i.e., un-textured, thereby hindering the tactile sensitivity of the user's fingertips on their index and middle fingers to a lesser extent than if the fingertip regions 108a, 110a were textured. FIG. 10C is a front elevation view of the fourth embodiment of the glove. In this instance, the glove 100 is an ambidextrous glove instead of a hand-specific glove. It will be understood that the rear elevation view of this glove will be a mirror image of what is illustrated in FIG. 10C.

Figure 11:
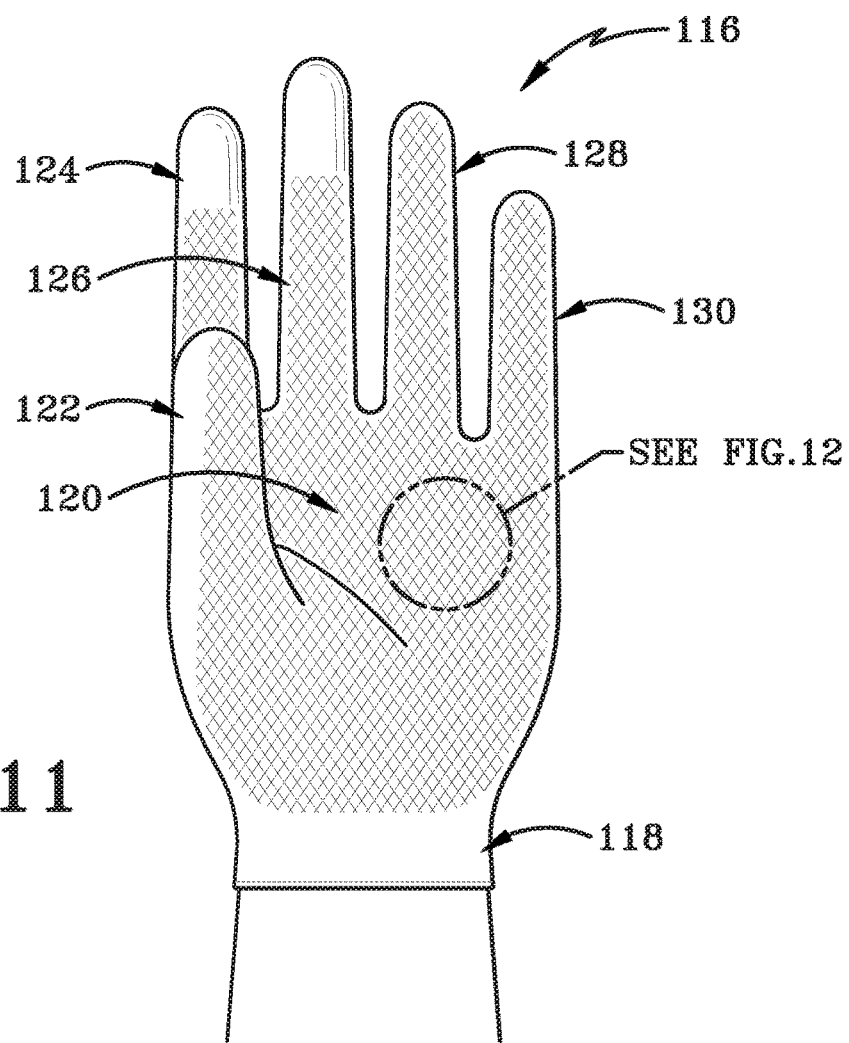
FIG. 11 is a front elevational view of another example of a glove in accordance with another aspect of the present disclosure, where the glove is a hand-specific glove that has texturing on the gripping surfaces of the glove but where the fingertip regions of the index finger region and middle finger region are free of texturing and are smooth.
Figure 12:
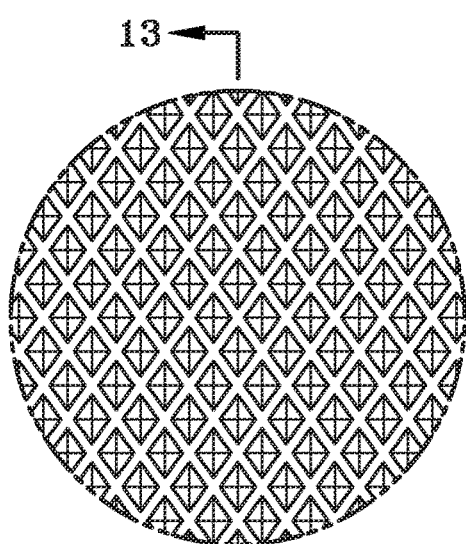
FIG. 12 is an enlargement of the highlighted region of FIG. 11 showing the diamond texture pattern.
Figure 13:
FIG. 13 is a cross-section taken along line 12-12 of FIG. 12 and showing the diamond texture pattern in greater detail.

Referring now to FIGS. 11-12, there is shown other examples of a glove in accordance with an aspect of the disclosure, generally indicated at 116. Glove 116 includes a wrist region 118, a palm region 120, a thumb region 122, an index finger region 124, a middle finger region 125, a ring finger region 128, and a little finger region 120. Glove 116 is illustrated as a hand-specific glove but the same principles as will be discussed hereafter may be incorporated into an ambidextrous glove.

Glove 116 may be substantially identical to any of the gloves 1, 50, 80, or 100 particularly as relating to the shape and features of these gloves. Glove 116 differs from the other gloves disclosed herein in that substantially the entire front surface of the glove, i.e., the gripping surfaces thereof, is textured except for the smooth and un-textured fingertip regions 124a and 125a in index finger region 124 and middle finger region 125. The rear surface and/or side surfaces of the glove 116 may also be textured if that is desired or if the glove is an ambidextrous glove.

The texture pattern utilized in glove 116 has been found to be most advantageous if the pattern is a diamond pattern, such as the pattern shown in FIGS. 12 and 12. The illustrated diamond pattern allows for better gripping ability when wearing glove 116 because of the additional friction provided by the raised diamond shapes on the glove's exterior surface. The diamond shapes in the pattern also effectively and efficiently wick water and other liquids away from the glove's exterior surface. This again improves the gripping ability of the exterior surface of the glove 116. It will be understood that instead of using a diamond pattern, other patterns may be utilized on glove 116.

Figure 11A:
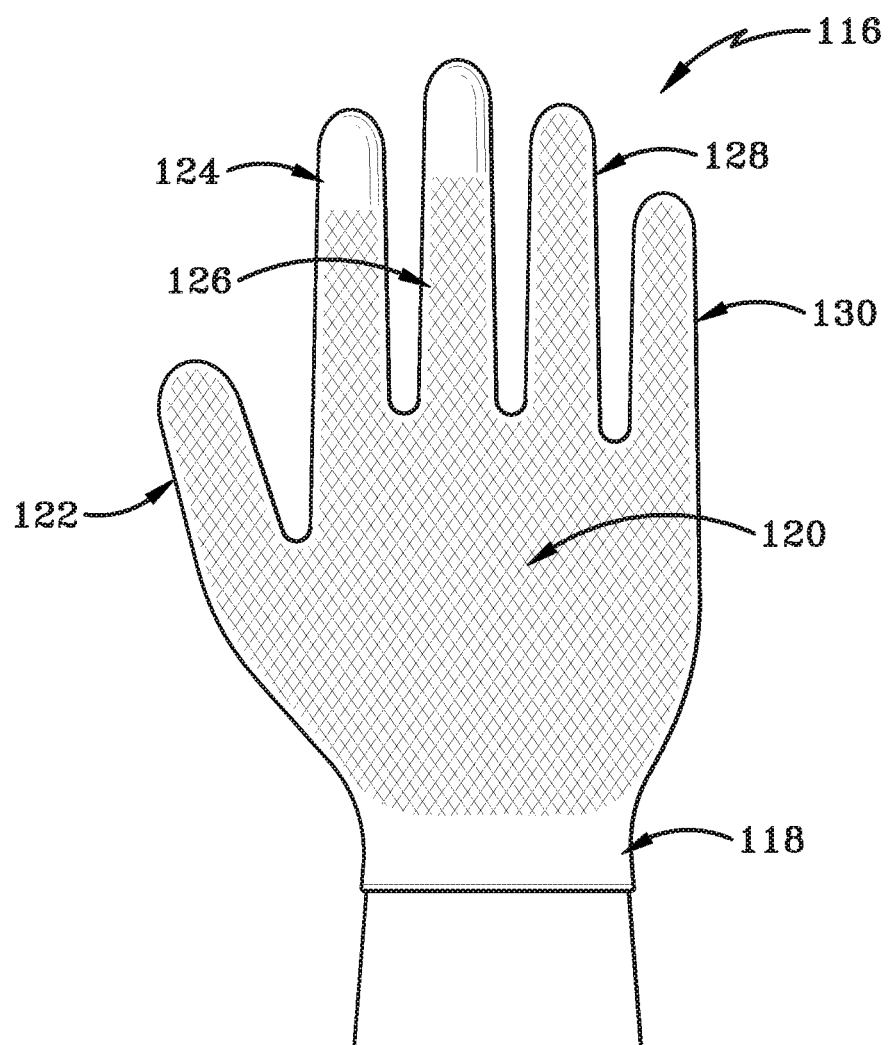
FIG. 11A is a front elevation view of another example of the glove shown as an ambidextrous glove.

FIG. 11A shows a front elevation view of another example of the glove 116 except that, in this instance, the glove 116 is an ambidextrous glove. It will therefore be understood that the rear elevation view of glove 116 will be a mirror image of what is illustrated in FIG. 11A. FIG. 11A also shows the same diamond pattern texturing the exterior surface of glove 116 that is illustrated in FIGS. 12 and 12.

FIGS. 14A-14E show a sixth embodiment of a glove 217. Glove 217 is illustrated as a hand-specific glove that includes a wrist region 202, palm region 204, thumb region 206, index finger region 208, middle finger region 210, ring finger region 212, and little finger region 214. FIGS. 14A-14E show exemplary hand-specific gloves 217 that have fingertip regions 206a, 208a, 210a, 212a, 214a that are generally of the same circumference as a remaining portion of the associated thumb region 206, index finger region 208, middle finger region 210, ring finger region 212, or little finger region 214. Collectively, each of these gloves 217 may be considered to be an example of a glove in accordance with the present disclosure that has one or more fingertip regions that are smooth (i.e., free of texture) and the rest of the glove is textured.

Figure 14A:
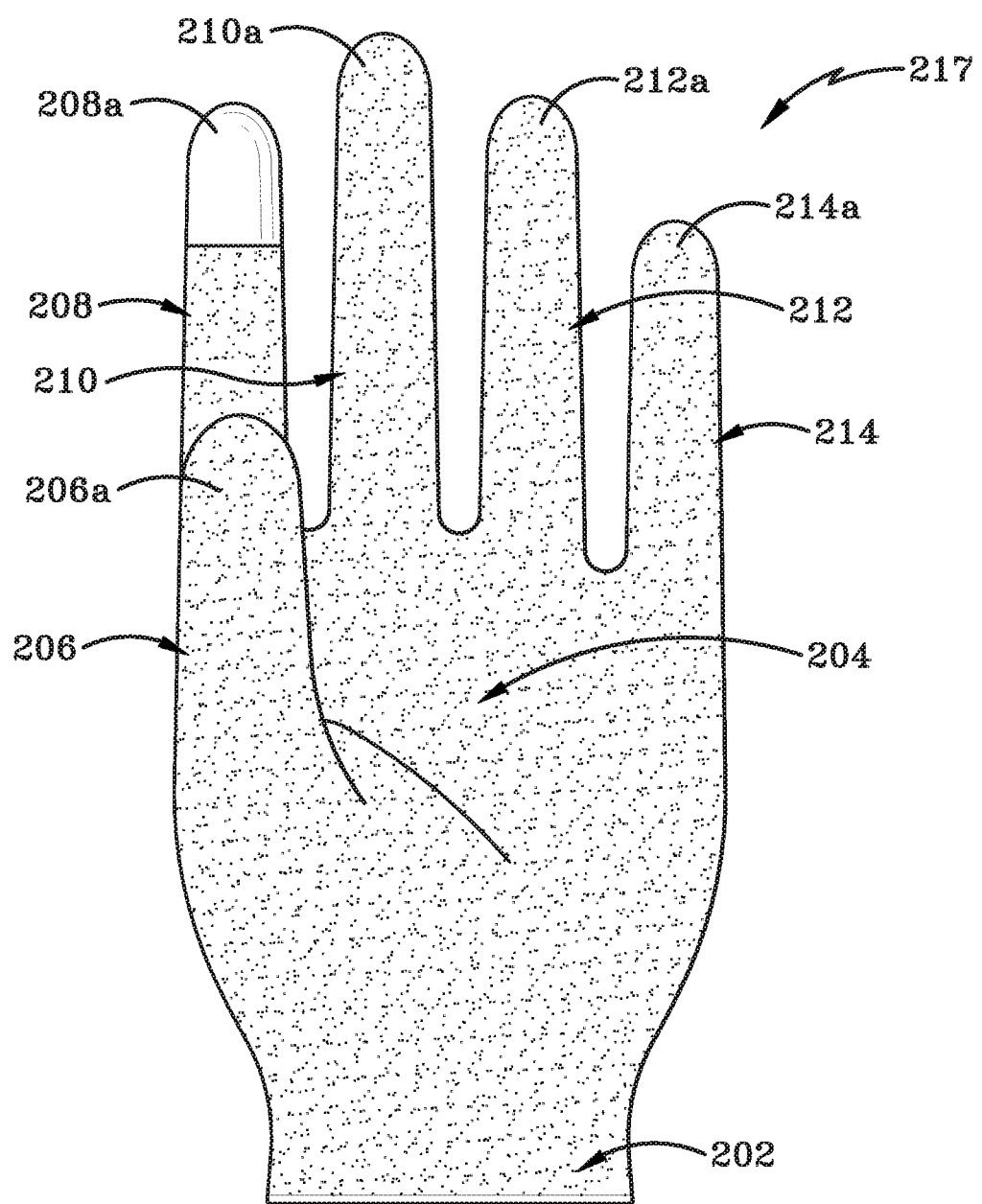
FIG. 14A is a front elevational view of a first example of a fifth embodiment of a glove in accordance with an aspect of the present disclosure, where the glove is a hand-specific glove that has texturing on the gripping surfaces of the glove but the fingertip region of the index finger region is free of texturing and is smooth.

FIG. 14A shows glove 217 having a fingertip region 208a on index finger region 208 that is smooth. The rest of the glove 210 may be textured.

Figure 14B:
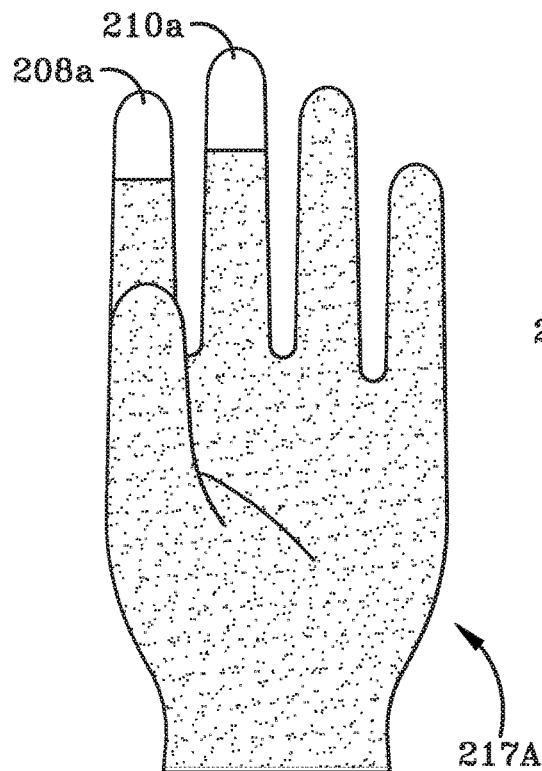
FIG. 14B is a front elevational view of a second example of the fifth embodiment where the glove is a hand-specific glove that has texturing on the gripping surfaces of the glove but the fingertip regions of the index finger region and middle finger region are free of texturing and are smooth.

FIG. 14B shows glove 217A having a fingertip region 208a, 210a on each of index finger region 208 and middle finger region 210 that is smooth. The rest of glove 217 may be textured. (The same glove is also shown in FIG. 11).

Figure 14C:
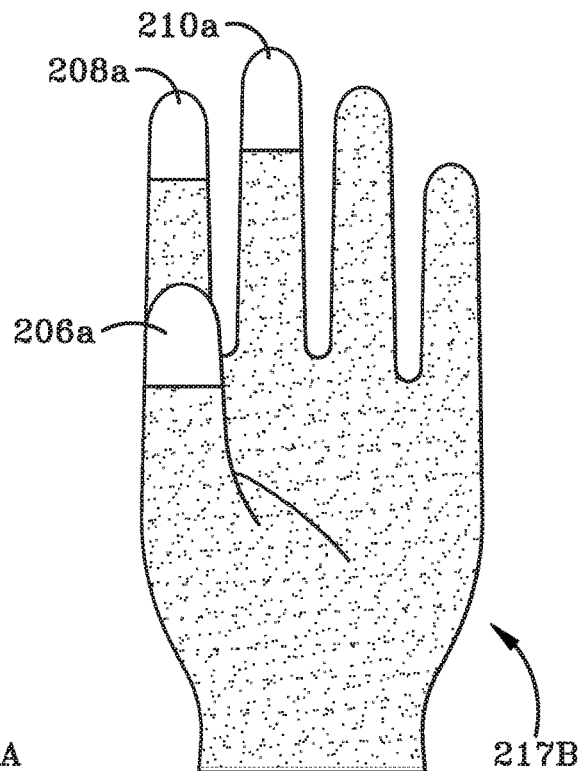
FIG. 14C is a front elevational view of a third example of the fifth embodiment where the glove is a hand-specific glove that has texturing on the gripping surfaces of the glove but the fingertip regions of the thumb region, index finger region, and middle finger region are free of texturing and are smooth.

FIG. 14C shows glove 217B having a fingertip region 206a, 208a, 210a on each of thumb region 206, index finger region 208, and middle finger region 210 that is smooth. The rest of glove 217 may be textured.

Figure 14D:
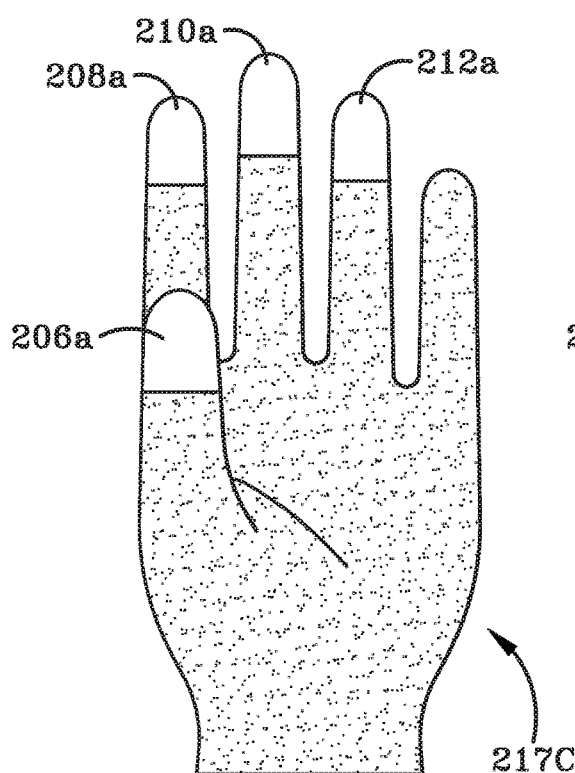
FIG. 14D is a front elevational view of a fourth example of the fifth embodiment where the glove is a hand-specific glove that has texturing on the gripping surfaces of the glove but the fingertip regions of the thumb region, index finger region, middle finger region and ring finger region are free of texturing and are smooth.

FIG. 14D shows glove 217C having a fingertip region 206a, 208a, 210a, 212a on each of thumb region 206, index finger region 208, middle finger region 210, and ring finger region 212 and all of these fingertip regions are smooth. The rest of glove 217 may be textured. It will be understood that in other exemplary gloves, the fingertip region 214a of little finger region 214 may be smooth instead of fingertip region 212a of ring finger region 212 and the rest of glove 217 including ring finger region 212 may be textured. It should further be understood that any four of the five fingertip regions 206a, 208a, 210a, 212a, or 214a may be textured while the fifth fingertip region may be un-textured along with the rest of glove 217.

Figure 14E:
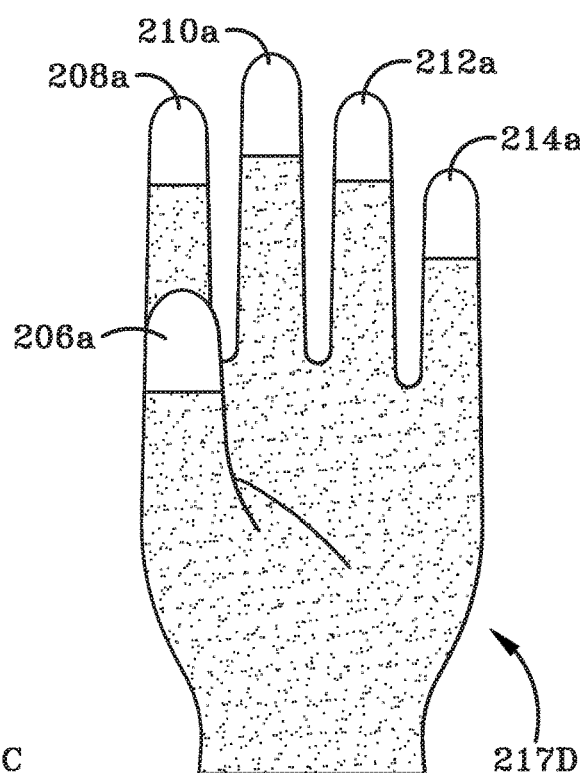
FIG. 14E is a front elevational view of a fifth example of the fifth where the glove is a hand-specific glove that has texturing on the gripping surfaces of the glove but all the fingertip regions are free of texturing and are smooth.

FIG. 14E shows glove 217D having a fingertip region 206a, 208a, 210a, 212a, 214a on each of thumb region 206, index finger region 208, middle finger region 210, ring finger region 212, and little finger regions 214 and all of these fingertip regions are smooth. The rest of glove 217 may be textured.

It will be understood that the smooth or un-textured portion of the fingertip region(s) on the gloves of FIGS. 14A-14E may be provided on that part of the fingertip region that would typically come into contact with objects if the user was holding the object in a gloved hand. In other examples, substantially the entire circumferential surface of the respective fingertip region may be smooth.

It will further be understood that only the front surface of the gloves 217-217D may be textured, i.e., that surface that will be adjacent the palm of the user's hand. The back surface, i.e., that surface that is adjacent the back of the user's hand may be textured or free of texture.

FIGS. 15A-15E show a sixth embodiment of a glove 317. Glove 317 is illustrated as a hand-specific glove that includes a wrist region 302, palm region 304, thumb region 306, index finger region 308, middle finger region 310, ring finger region 312, and little finger region 314. The lower ends of thumb region 306, index finger region 308, middle finger region 310, ring finger region 312, and little finger region 314 join an upper end of palm region 304. Gloves 317 shown in FIGS. 15A-15E have fingertip regions 306a, 308a, 310a, 312a, 314a that are generally of the same circumference as the remaining portion of the associated thumb region 306, index finger region 308, middle finger region 310, ring finger region 312, or little finger region 314. Collectively, each of these gloves 317 shown in FIGS. 15A-15E may be considered to be an example of a glove accordance with the present disclosure that includes one or more fingertip regions 306a, 308a, 310a, 312a, or 314a that are textured while the rest of the glove is smooth.

Figure 15A:
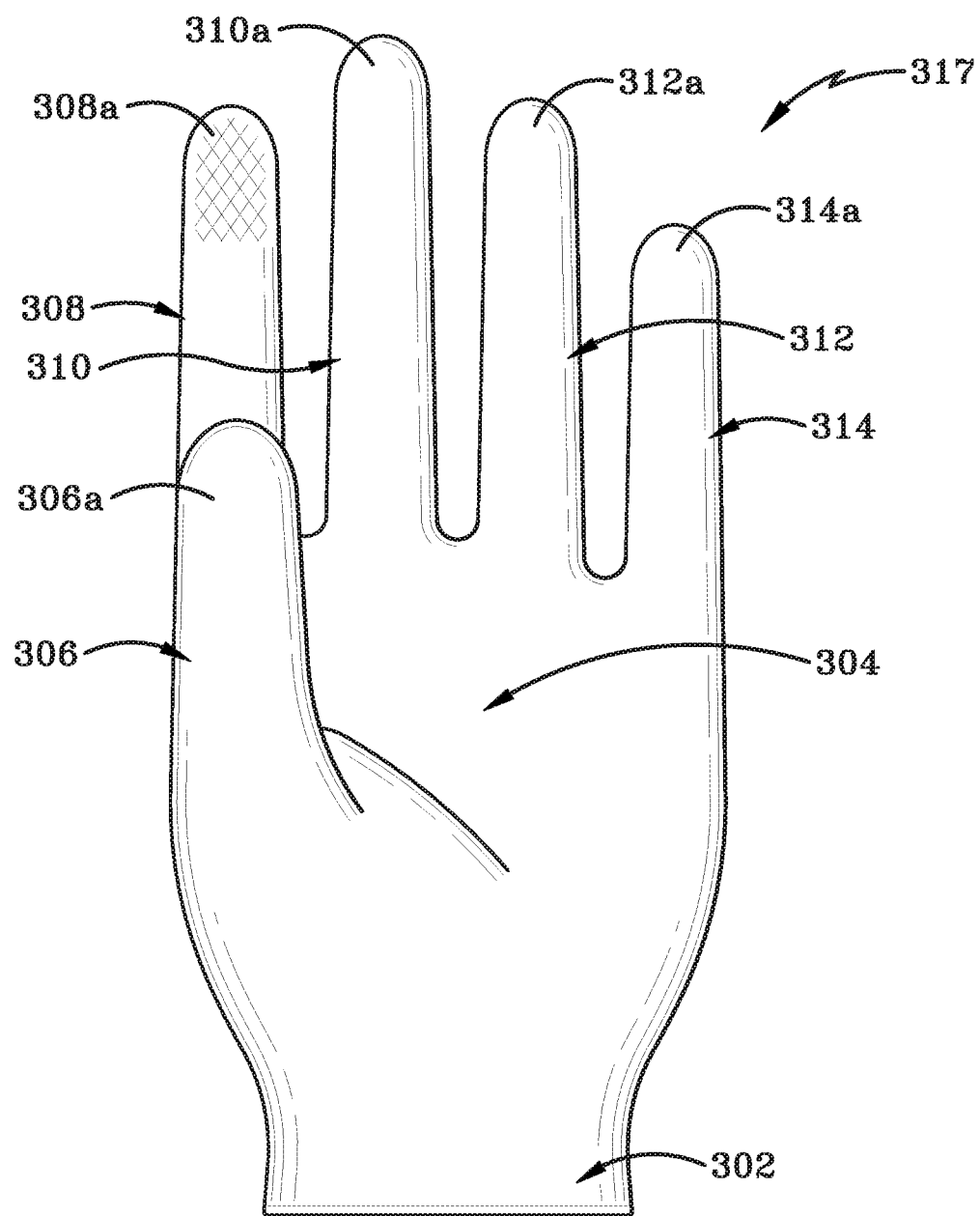
FIG. 15A is a front elevational view of a first example of a sixth embodiment of a glove in accordance with an aspect of the present disclosure, where the glove is a hand-specific glove that has smooth gripping surfaces and where the fingertip region of the index finger region is textured.

FIG. 15A shows glove 317 having a fingertip region 308a on index finger region 308 that is textured. The rest of glove 317 may be smooth.

Figure 15B:
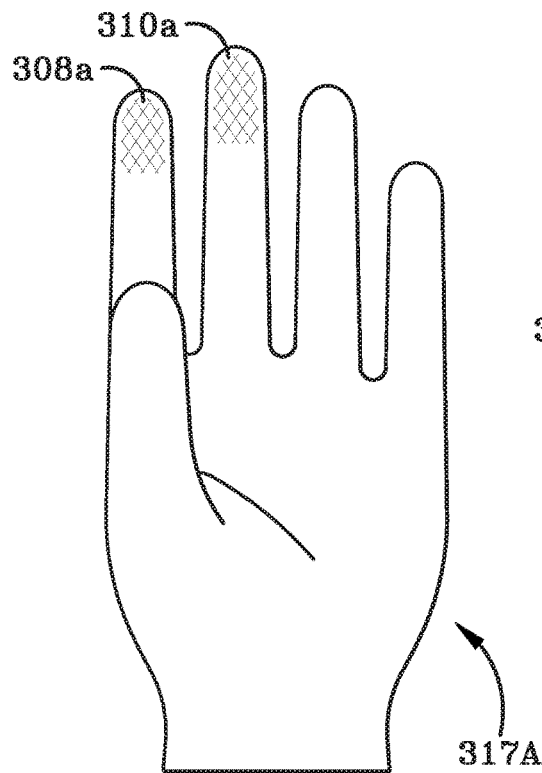
FIG. 15B is a front elevational view of a second example of the sixth embodiment where the glove is a hand-specific glove that has smooth gripping surfaces and where the fingertip regions of the index finger region and middle finger region are textured.

FIG. 15B shows glove 317A having a fingertip region 308a, 310a on each of index finger region 308 and middle finger region 310 that is textured. The rest of glove 317A may be smooth.

Figure 15C:
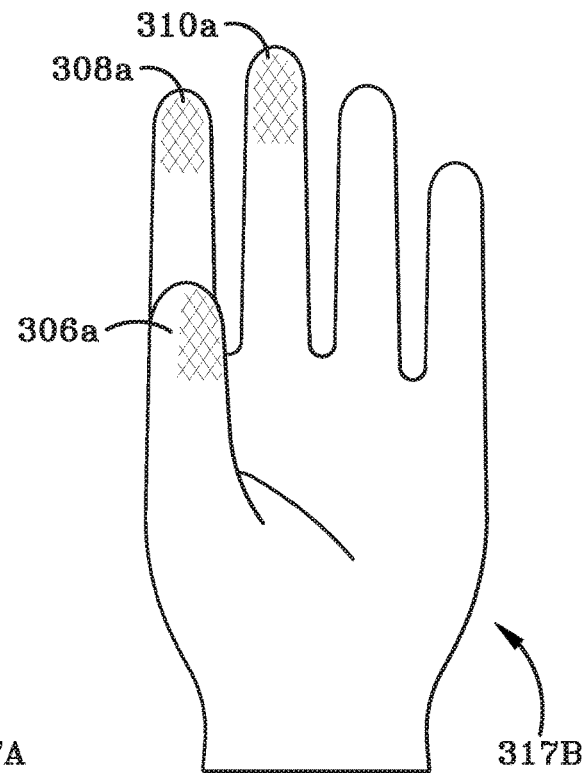
FIG. 15C is a front elevational view of a third example of the sixth where the glove is a hand-specific glove that has smooth gripping surfaces and the fingertip regions of the thumb region, index finger region, and middle finger region are textured.

FIG. 15C shows glove 317B having a fingertip region 306a, 308a, 310a on each of the thumb region 306, index finger region 308, and middle finger region 310 that is textured. The rest of glove 317B may be smooth. In particular, the gripping surfaces of fingertip regions 306a, 308a, and 310a may be textured. The remaining surfaces of fingertip regions 306a, 308a, and 310a (such as the back surface thereof) other than the gripping surfaces may be smooth or un-textured or they may be textured as desired.

Furthermore, the specific pattern of texturing shown on fingertip regions 306a, 308a, and 310a is illustrated as a diamond pattern. It will be understood that other differently configured patterns may be used instead of the diamond pattern. The specific pattern selected may be chosen based on the specific purpose or arena in which glove 317 is to be utilized.

Figure 15D:
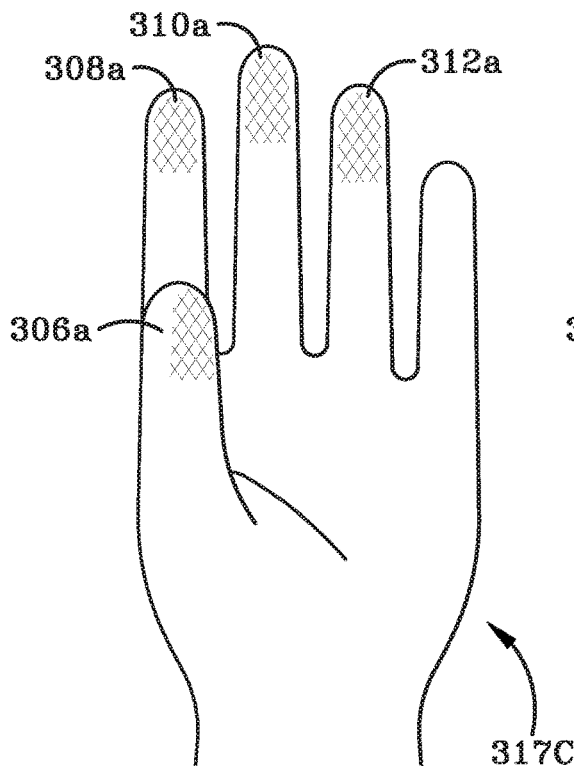
FIG. 15D is a front elevational view of a fourth example of the sixth embodiment where the glove is a hand-specific glove that has smooth gripping surfaces and the fingertip regions of the thumb region, index finger region, middle finger region and ring finger region are textured.

FIG. 15D shows glove 317C having a fingertip region 306a, 308a, 310a, 312a on each of thumb region 306, index finger region 308, middle finger region 310, and ring finger region 312 and all of these fingertip regions are textured. The rest of glove 317C may be smooth. Although not illustrated herein, it will be understood that the fingertip region 314a on little finger region 314 may be textured instead of fingertip region 312a of ring finger region 312. Any four out of the five fingertip regions 306a, 308a, 310a, 312a, 314a of thumb region 306, index finger region 308, middle finger region 310, ring finger region 312 and little finger region 314 may be textured and the fifth fingertip region may be smooth along with the rest of glove 317C.

Figure 15E:
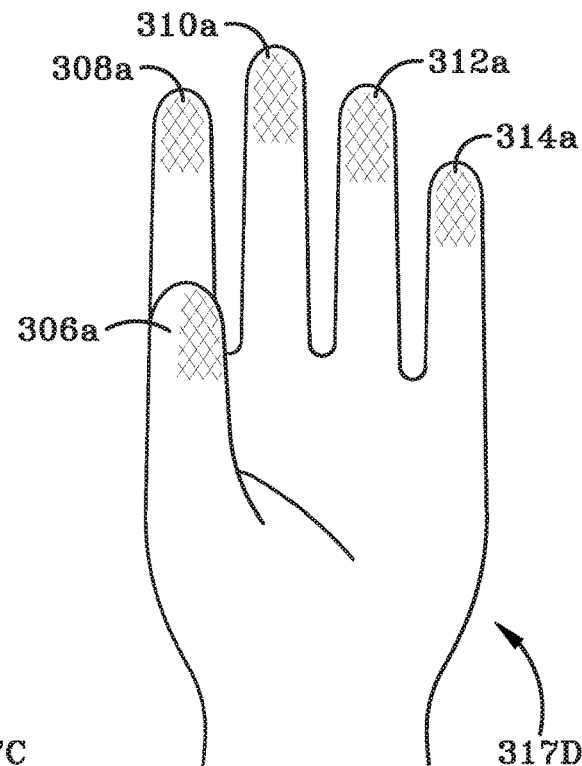
FIG. 15E is a front elevational view of a fifth example of the sixth embodiment where the glove is a hand-specific glove that has smooth gripping surfaces and all the fingertip regions are textured.

FIG. 15E shows glove 317D having a fingertip region 306a, 308a, 310a, 312a, 314a on each of thumb region 306, index finger region 308, middle finger region 310, ring finger region 312 and little finger region 314 and all of these fingertip regions may be textured. The rest of glove 317D may be smooth.

It will further be understood that the textured portion of the fingertip region(s) 306a, 308a, 310a, 312a, 314a may be provided on that part of the fingertip region that would typically come into contact with object if held in a gloved-hand. In other examples, substantially the entire circumferential surface of the fingertip region may be textured.

The texturing on one or more fingertip regions 306a, 308a, 310a, 312a, 314a helps improve the gripping ability of the user's gloved hand.

Figure 16A:
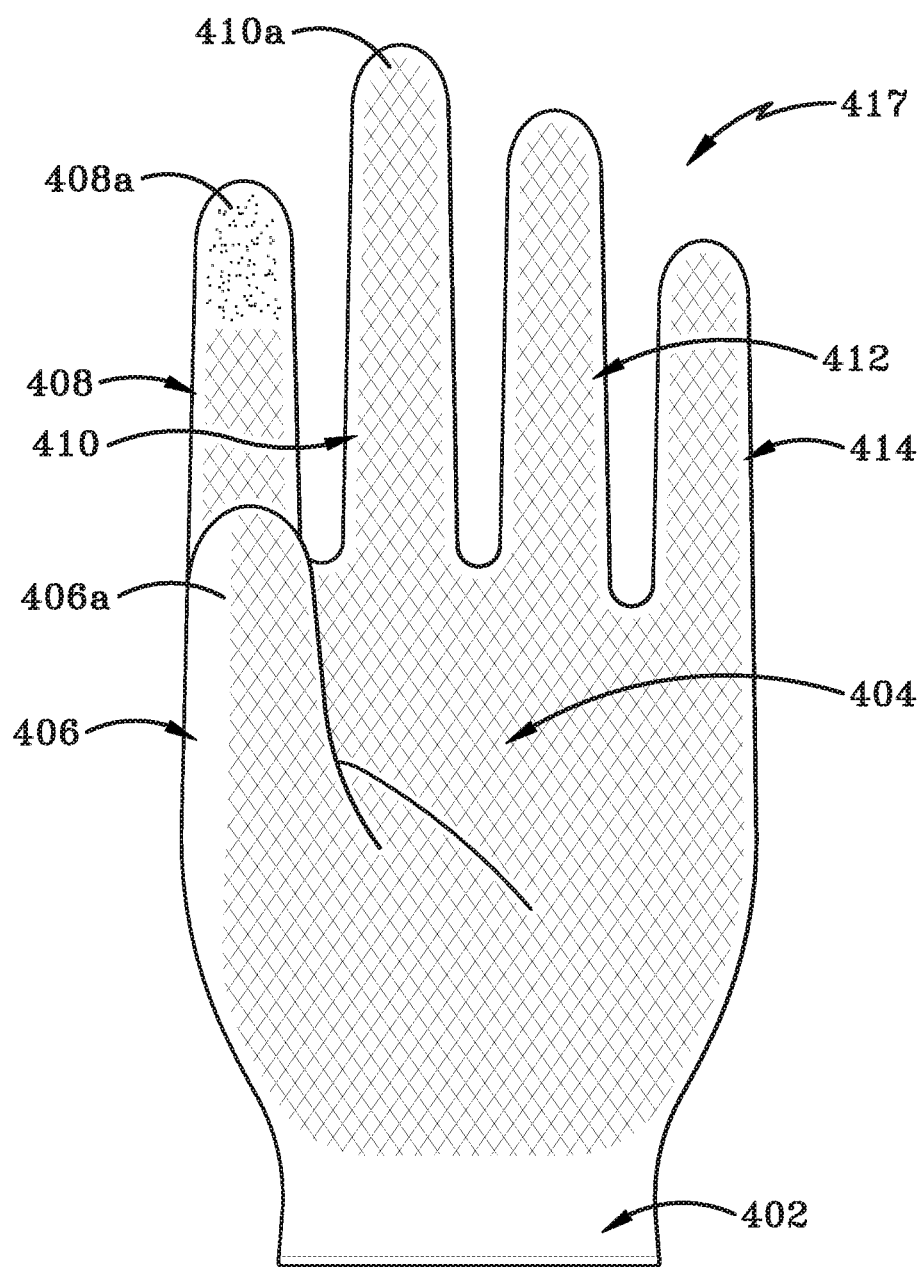
FIG. 16A is a front elevation view of a first example of a seventh embodiment of a glove in accordance with an aspect of the present disclosure, shown as a hand-specific glove, with a fingertip region of the index finger region being provided with a first texture and a rest of the glove being provided with a second texture.
Figure 16B:
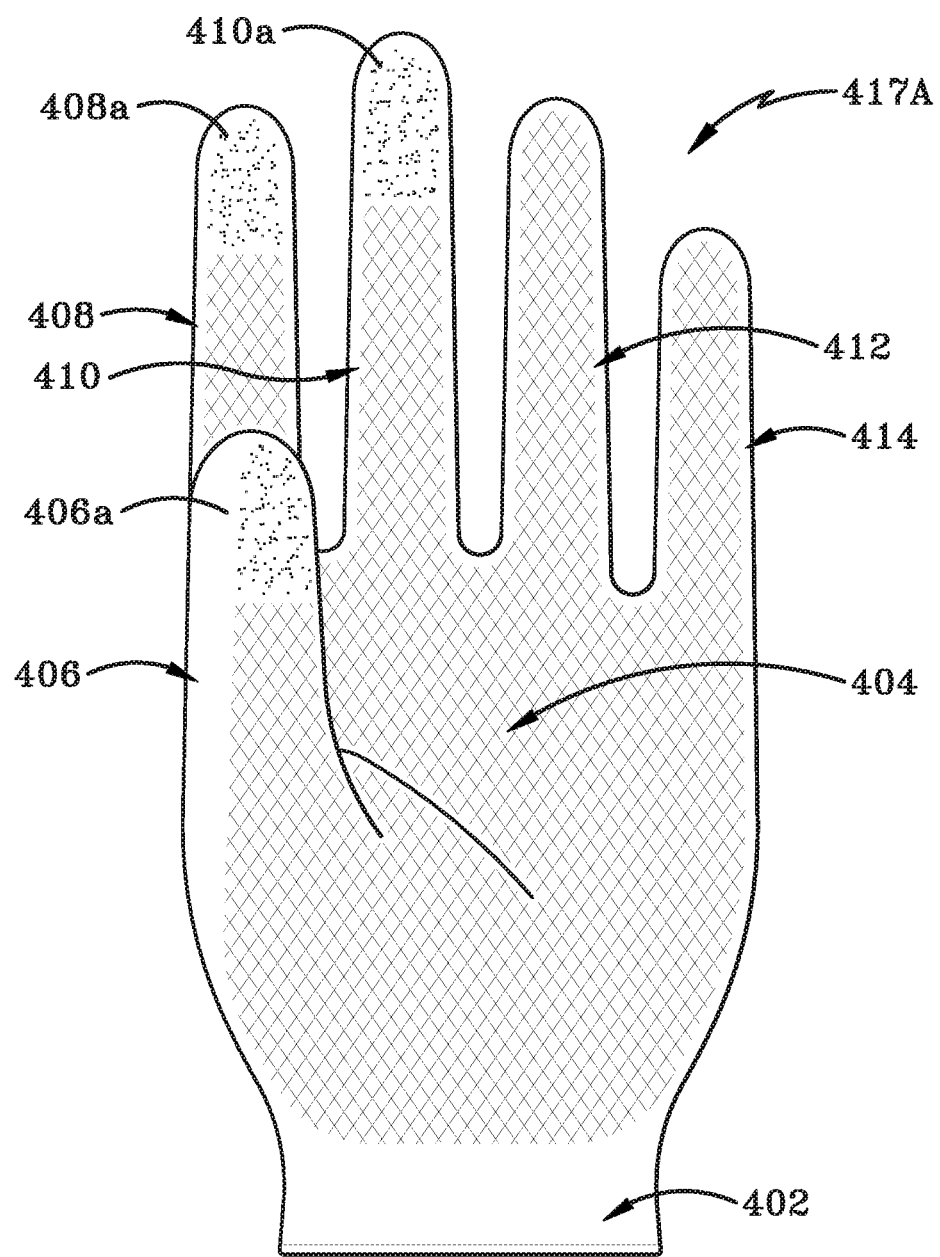
FIG. 16B is a front elevation view of second example of the seventh embodiment shown as a hand-specific glove; and showing the fingertip regions of the thumb region, index finger region and middle finger region having a first texture thereon and the rest of the glove with a second texture thereon.
Figure 16C:
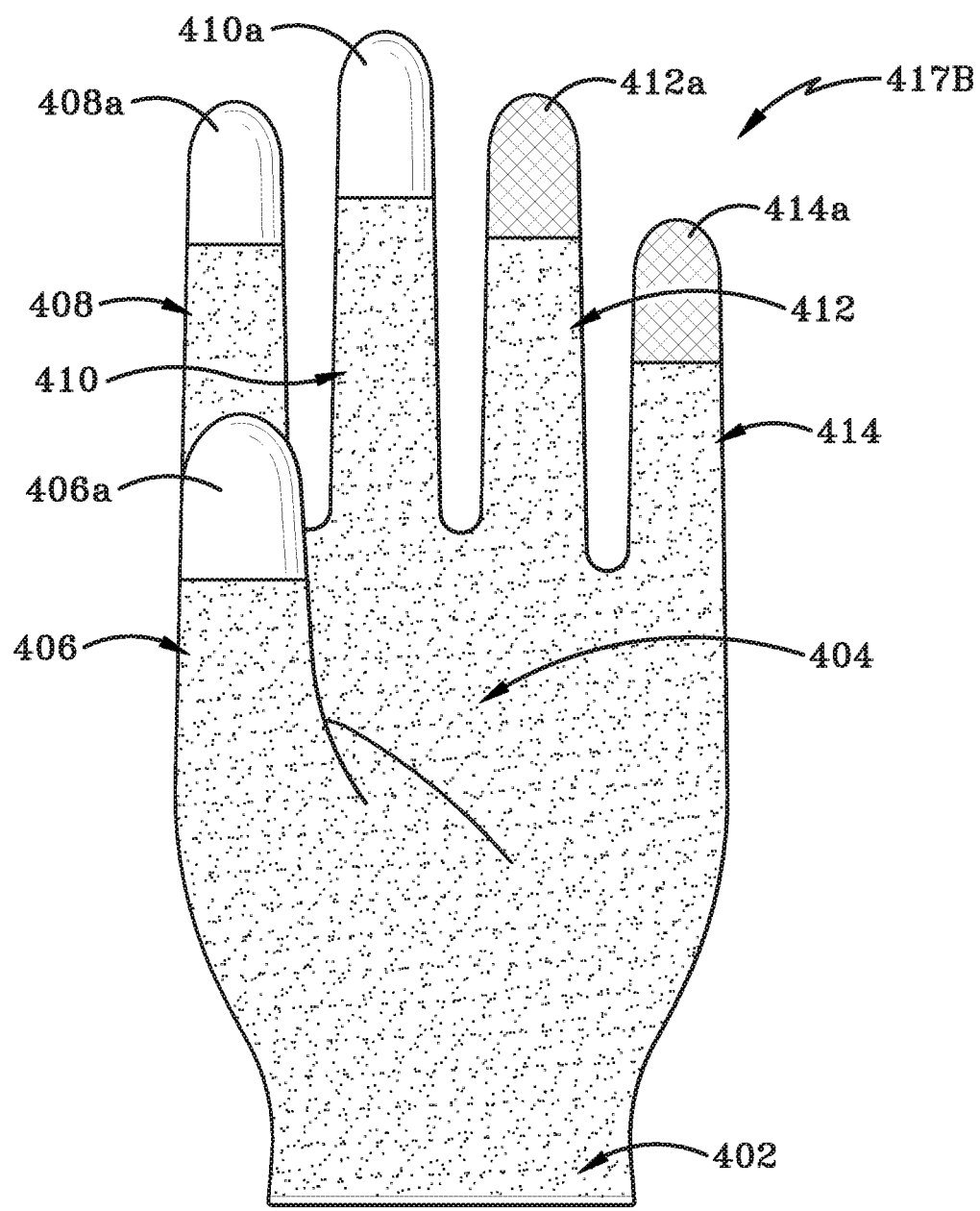
FIG. 16C is a front elevation view of third example of the seventh embodiment shown as a hand-specific glove and showing the fingertip regions of the thumb region, index finger region and middle finger region free of texture, the fingertip regions of the ring finger region and little finger region being provided with a first texture, and the rest of the glove being provided with a second texture.

FIGS. 16A-16C show a seventh embodiment of the glove 417. Glove 417 is illustrated as a hand-specific glove that includes a wrist region 402, palm region 404, thumb region 406, index finger region 408, middle finger region 410, ring finger region 412, and little finger region 414. Gloves 417 shown in FIGS. 16A-16C have fingertip regions 406a, 408a, 410a, 412a, 414a that are generally of the same circumference as the remaining portion of the associated thumb region 406, index finger region 408, middle finger region 410, ring finger region 412, or little finger region 414. Collectively, each glove 417 may be considered to be an example of a glove in accordance with the present invention that may include some fingertip regions that are smooth, other fingertip regions that may be provided with one or more different textures, while the rest of the glove may be smooth or textured with a first texture or a second texture. FIGS. 16A through 16C are provided by way of example only to illustrate some of the numerous combinations of textured and smooth areas that may be provided on glove 417.

FIG. 16A shows glove 417 having a fingertip region 408a on index finger region 408 that is provided with a first texture. The rest of glove 417 is provided with a second texture.

FIG. 16B shows glove 417A having a fingertip region 406a, 408a, 410a, on each of the thumb region 406, index finger region 408, and middle finger region 410 that is provided with a first texture. The rest of glove 417A is provided with a second texture.

FIG. 16C shows glove 417B having a fingertip region 406a, 408a, 410a on each of the thumb region 406, index finger region 408, and middle finger region 410 that is smooth. Fingertip regions 412a on ring finger region 412 and little finger region 414 are provided with a first texture. The rest of glove 417B is provided with a second texture.

It should be noted that FIG. 7, previously described herein, also shows a glove 80 that is of a similar type to those illustrated in FIGS. 16A-16C. Glove 80 has fingertip regions 88B, 88C on index finger region 16 and middle finger region 18 that are smooth; the fingertip regions 88A, 88D, 88E on thumb region 14, ring finger region 20, and little finger region 22 are provided with a first texture; and the rest of the glove is provided with a second texture. The smooth and textured surfaces shown in FIGS. 16A-16C and FIG. 7 may be provided on only those areas of the gloves that will come into contact with an object that is held. The opposite surface of the glove (i.e., the back surface of the glove) may be smooth or textured in any desired manner.

FIGS. 17A-17E show an eighth embodiment of a glove 517 in accordance with the present disclosure. Glove 517 is illustrated as a hand-specific glove that includes a wrist region 502, palm region 504, thumb region 506, index finger region 508, middle finger region 510, ring finger region 512, and little finger region 514. Collectively, each of these gloves 517 shown in FIGS. 17A-17E may be considered to be an example of a glove accordance with the present disclosure that includes one or more fingertip regions 506a, 508a, 510a, 512a, 514a that may be of a smaller circumference than the circumference of the remaining portion of the associated thumb region 506, index finger region 508, middle finger region 510, ring finger region 512, and little finger region 514. A step-down region 513 (FIGS. 17A, 17E) is provided between the circumference of each of the remaining portions 506c, 508c, 510c, 512c, 514c and the associated smaller circumference of the fingertip region 506a, 508a, 510a, 512a, 514a.

One or more of the other fingertip regions 506a, 508a, 510a, 512a, 514a may be of generally a same circumference as the remaining portion of the associated thumb region 506, index finger region 508, middle finger region 510, ring finger region 512, and little finger region 514; i.e., the other fingertip regions are not molded to be specifically narrower so that they are thinned and pulled taut over the fingertips when the glove 517 is donned.

Figure 17A:
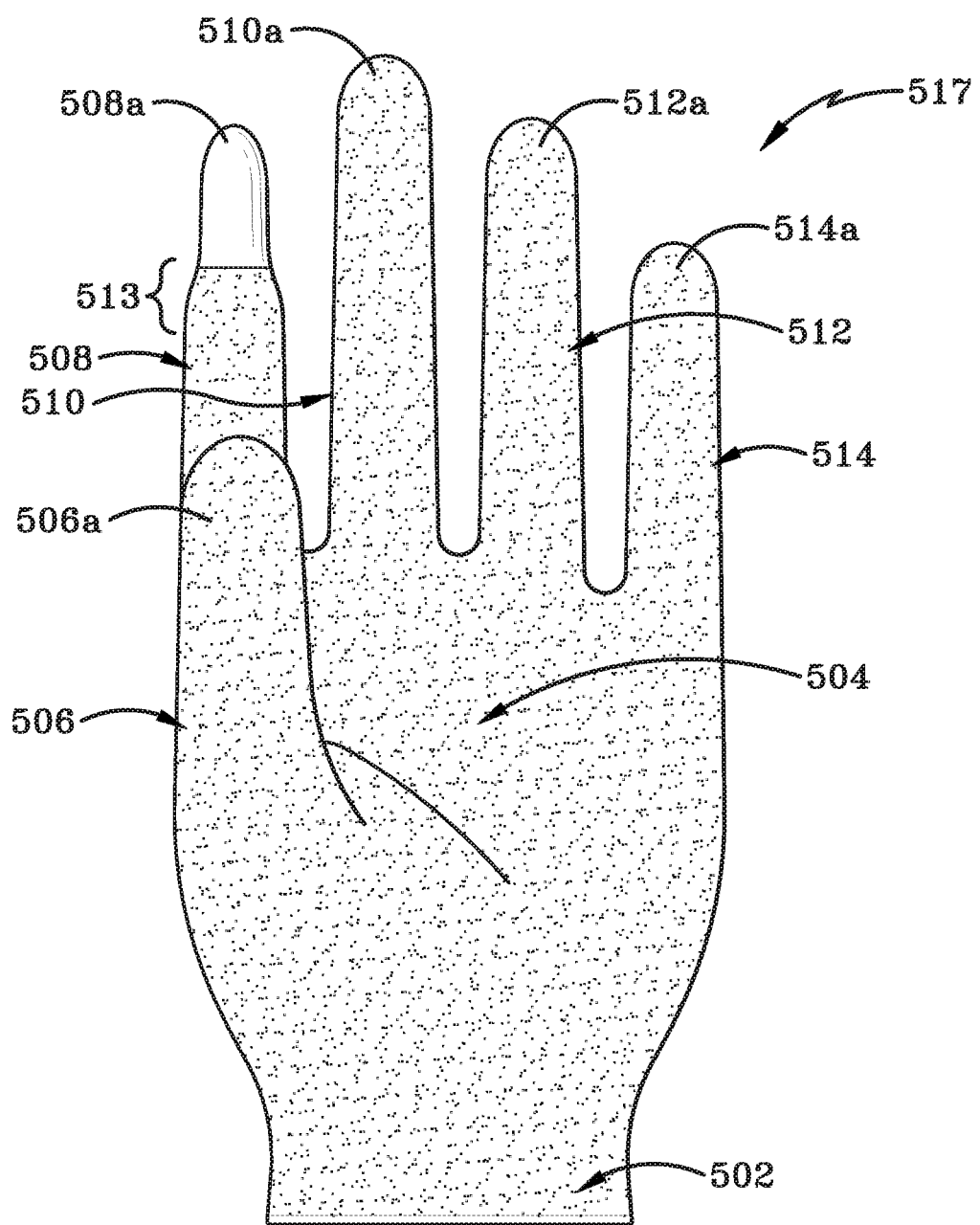
FIG. 17A is a front elevational view of a first example of an eighth embodiment of a glove in accordance with an aspect of the present disclosure, where the glove is a hand-specific glove that has texturing on the gripping surfaces of the glove but the fingertip region of the index finger region is of smaller circumference than a remaining portion of the index finger region and is free of texturing and is smooth.

FIG. 17A shows glove 517 having a fingertip region 508a on index finger region 508 that is of a smaller circumference than a remaining portion 508c of the index finger region 508. The fingertip region 508a of index finger region 508 is smooth. The rest of glove 517 may be textured.

Figure 17B:
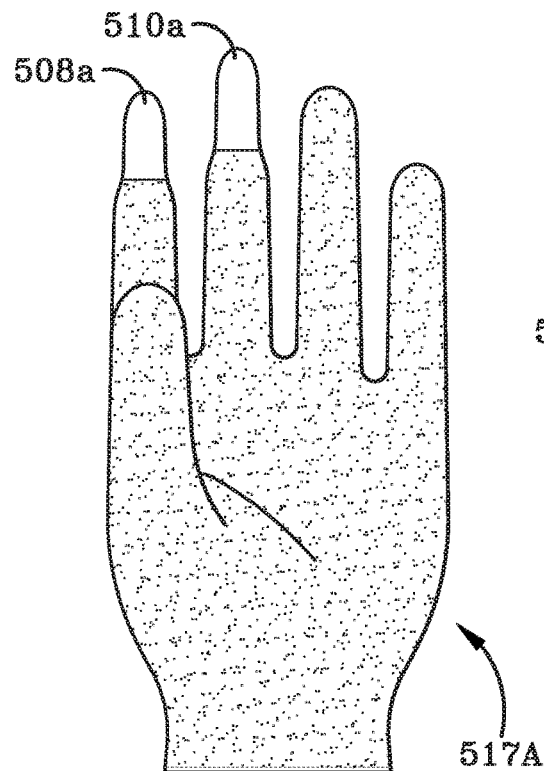
FIG. 17B is a front elevational view of a second example of the eighth embodiment where the glove is a hand-specific glove that has texturing on the gripping surfaces of the glove but the fingertip regions of the index finger region and middle finger region are of a smaller circumference than a remaining portion of the associated index finger region and middle finger region and are free of texturing and are smooth.

FIG. 17B shows glove 517A having a fingertip region 508a, 510a on index finger region 508 and on middle finger region 510 that are of a smaller circumference than an associated remaining portion 508c, 510c of index finger region 508 and middle finger region 510. The fingertip regions 508a, 510a on index finger region 508 and middle finger region 510 are smooth. The rest of glove 517A may be textured.

Figure 17C:
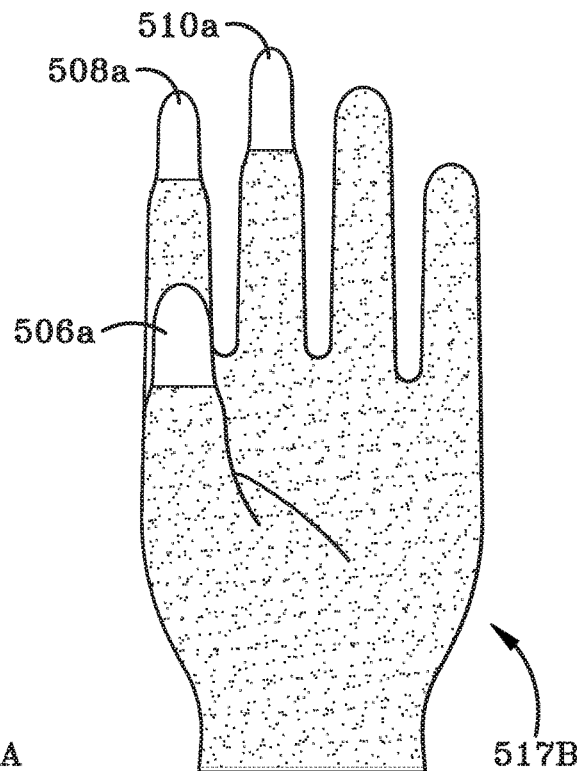
FIG. 17C is a front elevational view of a third example of the eighth embodiment where the glove is a hand-specific glove that has texturing on the gripping surfaces of the glove but the fingertip regions of the thumb region, index finger region, and middle finger region of smaller circumferences than the remaining portions of the associated thumb region or finger regions and are free of texturing and are smooth.

FIG. 17C shows glove 517B having fingertip regions 506a, 508a, 510 on thumb region 506, index finger region 508, and middle finger region 510 that are of a smaller circumference than an associated remaining portion 506c, 508c, 510c of thumb region 506, index finger region 508, and middle finger region 510. The fingertip regions 506a, 508a, 510a on thumb region 506, index finger region 508, and middle finger region 510 are smooth. The rest of glove 517B may be textured.

Figure 17D:
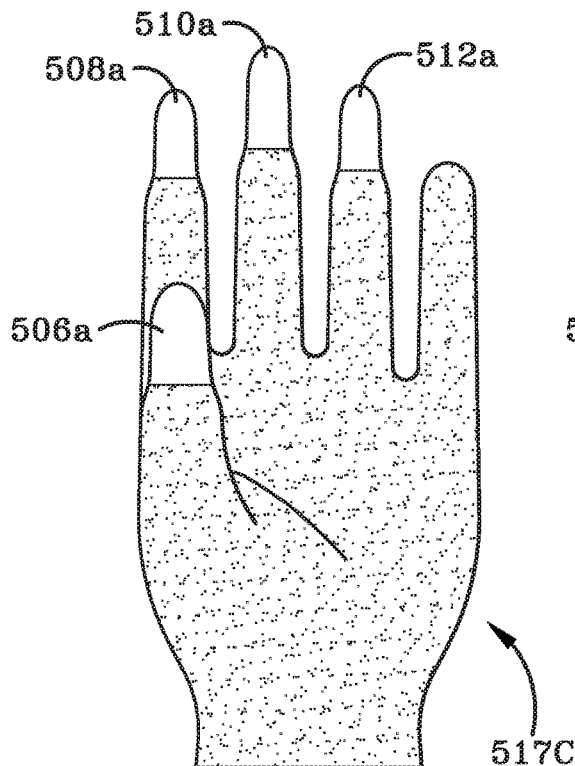
FIG. 17D is a front elevational view of a fourth example of the eighth embodiment where the glove is a hand-specific glove that has texturing on the gripping surfaces of the glove but the fingertip regions of the thumb region, index finger region, middle finger region and ring finger region are of smaller circumferences than the remaining portions of the associated thumb region or finger regions and are free of texturing and are smooth.

FIG. 17D shows glove 517C having fingertip regions 506a, 508a, 510a, 512a that are of a smaller circumference than an associated remaining portion 506c, 508c, 510c, 512c of the thumb region 506, index finger region 508, middle finger region 510, ring finger region 512. These fingertip regions are smooth while the rest of the glove (including fingertip region 514a) is textured. Although not illustrated herein, it will be understood that fingertip region 514a of little finger region 514 may be of a smaller circumference that the remaining portion 514c of little finger region 514 and that fingertip region 512a may not be of a smaller circumference relative to remaining portion 512c of ring finger region. The four fingertip regions may be smooth while the rest of the glove 517C may be textured.

Figure 17E:
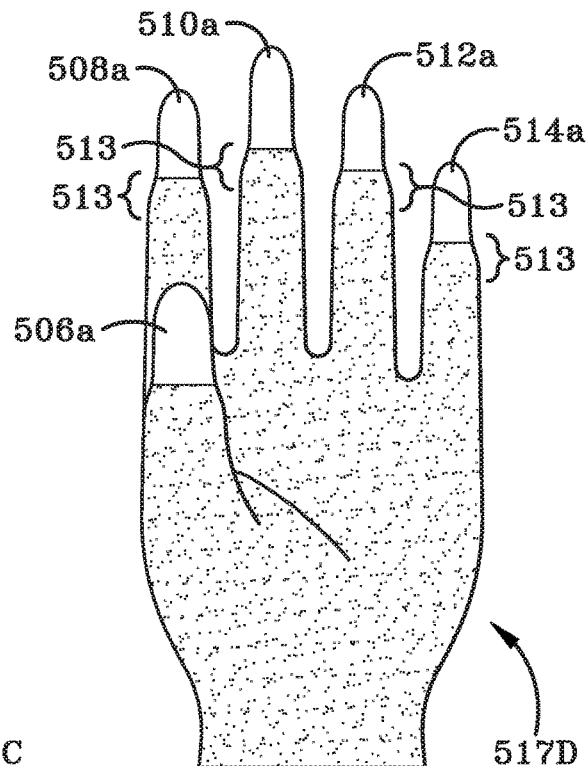
FIG. 17E is a front elevational view of a fifth example of the eighth where the glove is a hand-specific glove that has texturing on the gripping surfaces and all the fingertip regions are of smaller circumferences than the associated thumb region or finger region and are free of texturing and are smooth.

FIG. 17E shows glove 517D having fingertip regions 506a, 508a, 510a, 512a, 514a on all five of the thumb region 506, index finger region 508, middle finger region 510, ring finger region 512, and little finger region 514 that are of a smaller circumference than an associated remaining portion 506c, 508c, 510c, 512c, 514c of the associated thumb region 506, index finger region 508, middle finger region 510, ring finger region 512, or little finger region 514. The fingertip regions may all be smooth. The rest of the glove 517D may be textured.

It will further be understood that the smooth portion of the fingertip region(s) may be provided on only that part of the fingertip region that will come into contact with objects if held in a gloved hand, i.e., the front surface of the fingertip regions. In other examples, substantially the entire circumferential surface of the fingertip region may be smooth.

It will be understood that in other exemplary gloves in accordance with the present disclosure, the gloves may be substantially identical to the gloves shown in FIGS. 17A-17E except that the smaller circumference fingertip region(s) may be textured instead of being smooth; and the rest of the glove may be smooth instead of being textured.

Figure 18A:
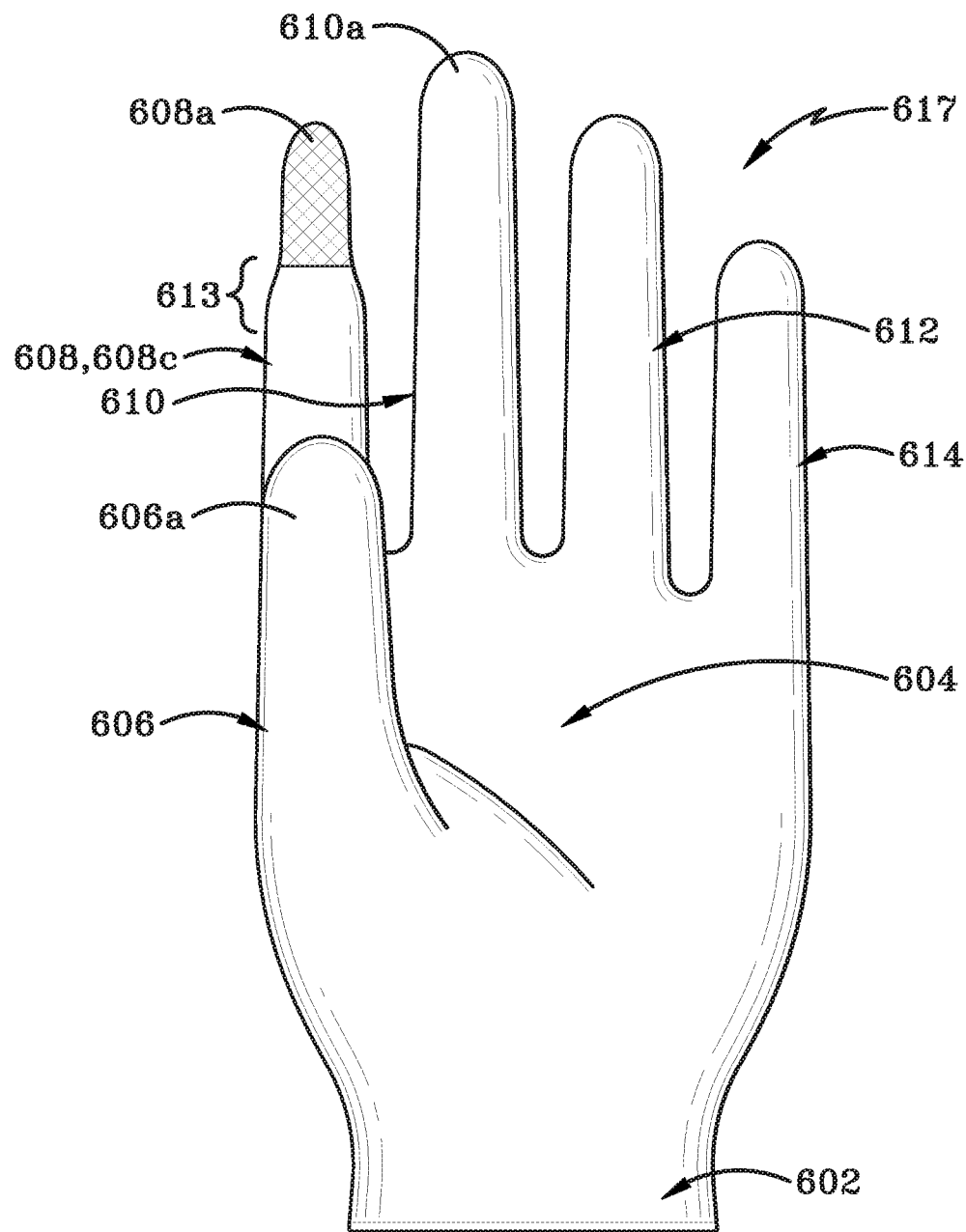
FIG. 18A is a front elevation view of a first example of a ninth embodiment of the glove in accordance with an aspect of the present disclosure, shown as a hand-specific glove, with a narrowed and textured fingertip region on the index finger region, and where a rest of the glove is smooth/non-textured.

FIG. 18A shows a first example of a ninth embodiment of a glove in accordance with an aspect of the present disclosure, generally indicated as glove 617. Glove 617 is a hand-specific glove that includes a wrist region 602, palm region 604, thumb region 606, index finger region 608, middle finger region 610, ring finger region 612 and little finger region 614. Glove 617 has fingertip regions 606a, 608a, 610a, 612a, 614a. Fingertip region 608a on index finger region 608 is of a circumference that is smaller than a circumference of an associated remaining portion 608c of index finger region 608. A step-down region 613 is provided between the circumference of the remaining portions 608c and the associated smaller circumference of the fingertip region 608a. The fingertip regions 606a, 610a, 612a, 614a are of generally a same circumference as the remaining portions of the associated thumb region 606, middle finger region 610, ring finger region 612 and little finger region 614.

In glove 617, the gripping surface of fingertip region 608a of index finger region 608 is textured. The gripping surface of fingertip region is that portion of the glove surface that would tend to typically contact an object if the user holds or picks up the object while wearing glove 617. The texturing on fingertip region 608a helps a user to better grip articles and objects than if this fingertip region 608a was smooth. Because of the reduced or smaller circumference of fingertip region 608a relative to the remaining portion 608c, the fingertip region 608a may tend to be thinned and pulled taut over a tip of the user's index finger when glove 617 is donned. This means that tactile sensitivity is maintained in the user's index finger while the user's gripping ability while wearing glove 617 is enhanced by the texturing provided on fingertip region 608a.

Furthermore, the specific pattern of texturing shown on fingertip region 608a is a diamond pattern. It will be understood that other differently configured patterns may be used instead of the diamond pattern. The specific pattern selected may be chosen based on the specific purpose or arena in which glove 617 is to be utilized.

Figure 18B:
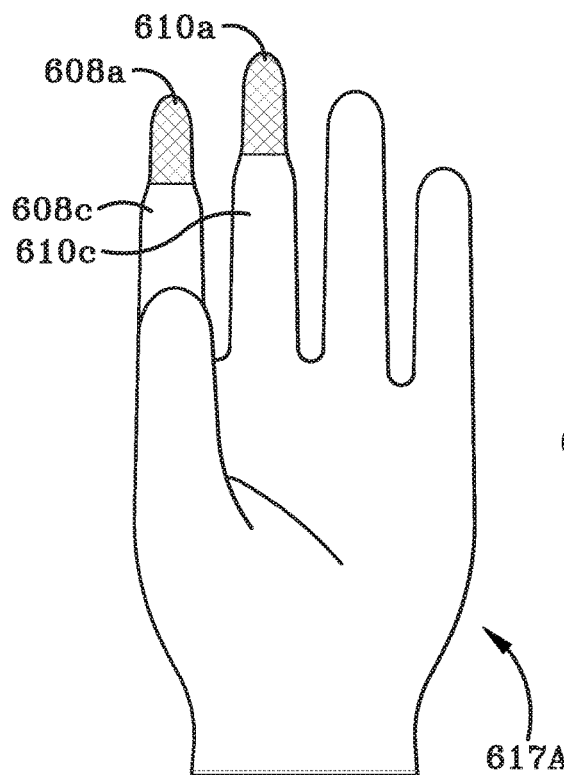
FIG. 18B is a front elevational view of a second example of the ninth embodiment where the glove is a hand-specific glove with a narrowed and textured fingertip region on the index finger region and middle finger region, and where a rest of the glove is smooth/non-textured.
Figure 18C:
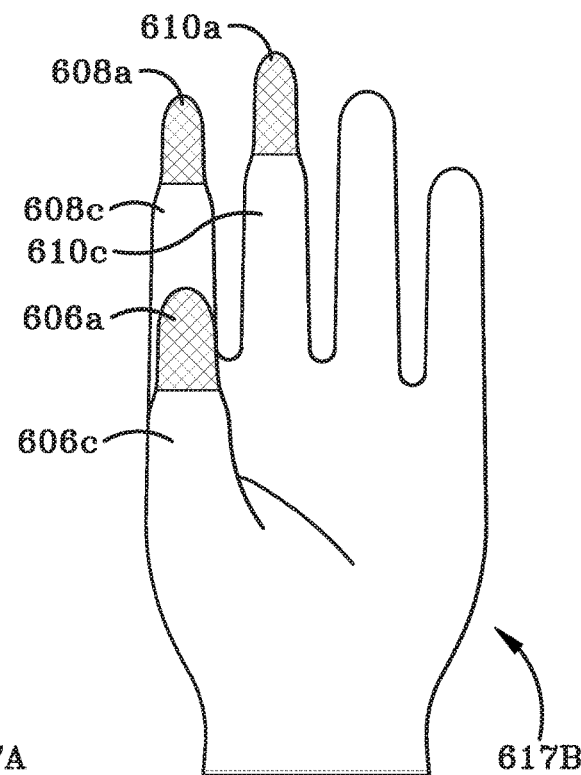
FIG. 18C is a front elevational view of a third example of the ninth embodiment where the glove is a hand-specific glove with a narrowed and textured fingertip region on the thumb region, the index finger region, and the middle finger region, and where a rest of the glove is smooth/non-textured.

FIG. 18B shows a glove 617A that is substantially identical to glove 617 except that both of the fingertip regions 608a, 610a are of a reduced or smaller circumference relative to a remaining portion of index finger region 608 and middle finger region 610. The reduced or smaller circumference fingertip regions 608a, 610a are provided with a texture while the rest of glove 617A is smooth/non-textured;

FIG. 18C shows a glove 617B that is substantially identical to glove 617 except that the fingertip regions 606a, 608a, 610a of thumb region 606, index finger region 608, and middle finger region 610 are of a reduced or smaller circumference relative to a remaining portion of thumb region 606, index finger region 608, and middle finger region 610. The reduced or smaller circumference fingertip regions 606a, 608a, 610a are provided with a texture while the rest of glove 617B is smooth/non-textured. Glove 617B is therefore substantially identical to glove 517B shown in FIG. 17C except for the location of the textured and smooth areas.

Figure 18D:
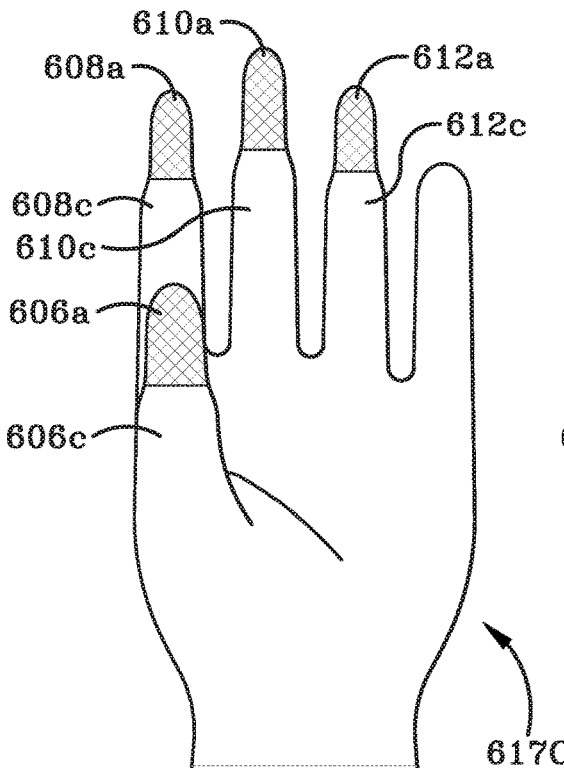
FIG. 18D is a front elevational view of a fourth example of the ninth embodiment, where the glove is a hand-specific glove with a narrowed and textured fingertip region on the thumb region, the index finger region, the middle finger region and the ring finger region; and where a rest of the glove is smooth/non-textured.

FIG. 18D shows a glove 617C that is substantially identical to glove 617 except that the fingertip regions 606a, 608a, 610a, 612a of thumb region 606, index finger region 608, middle finger region 610, and ring finger region 612 are of a reduced or smaller circumference relative to a remaining portion of thumb region 606, index finger region 608, middle finger region 610, and ring finger region 612. The reduced or smaller circumference fingertip regions 606a, 608a, 610a, 612a are provided with a texture while the rest of glove 617C is smooth/non-textured. It will be understood that fingertip region 614a of little finger region 614 may be fabricated to be of a reduced or smaller circumference relative to the associated remaining portion of little finger region 614 instead of providing the reduced or smaller circumference fingertip region 612a. In this instance, fingertip region 614a will be provided with a texture. The rest of glove 617C will be smooth or non-textured.

Figure 18E:
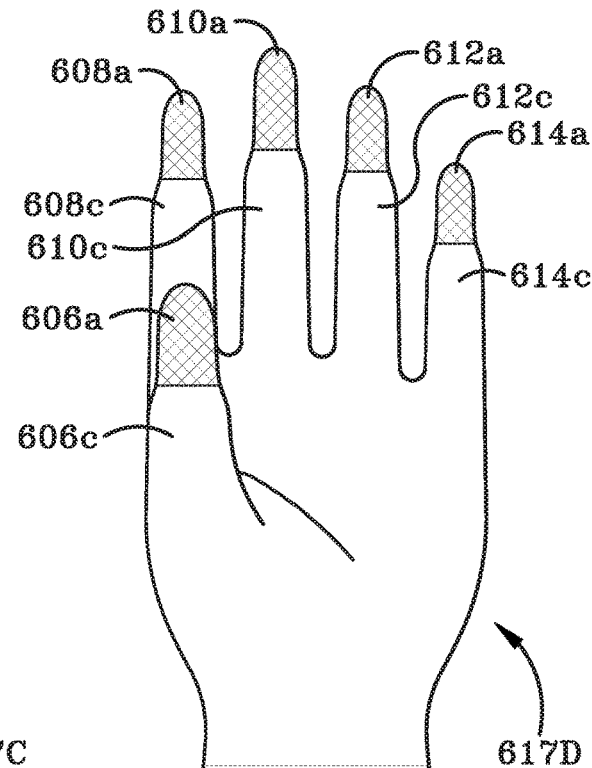
FIG. 18E is a front elevational view of a fifth example of the ninth with five narrowed and textured fingertip regions and where a rest of the glove is smooth/non-textured.

FIG. 18E shows a glove 617D having five fingertip regions 606a, 608a, 610a, 612a, and 614a that are all textured and of a reduced or smaller circumference relative to the remaining portions of thumb region 606, index finger region 608, middle finger region 610, ring finger region 612, and ring finger region 614. The rest of glove 617D is smooth or non-textured. Although not specifically numbered, it will be understood that in each of the gloves illustrated in FIGS. 18B-18E, a step-down region similar to step-down region 613 shown in FIG. 18A, may be provided between the circumference of each of the remaining portions 606c, 610c, 612c, 614c and any associated smaller circumference of the fingertip region 606a, 610a, 612a, 614a.

Figure 19A:
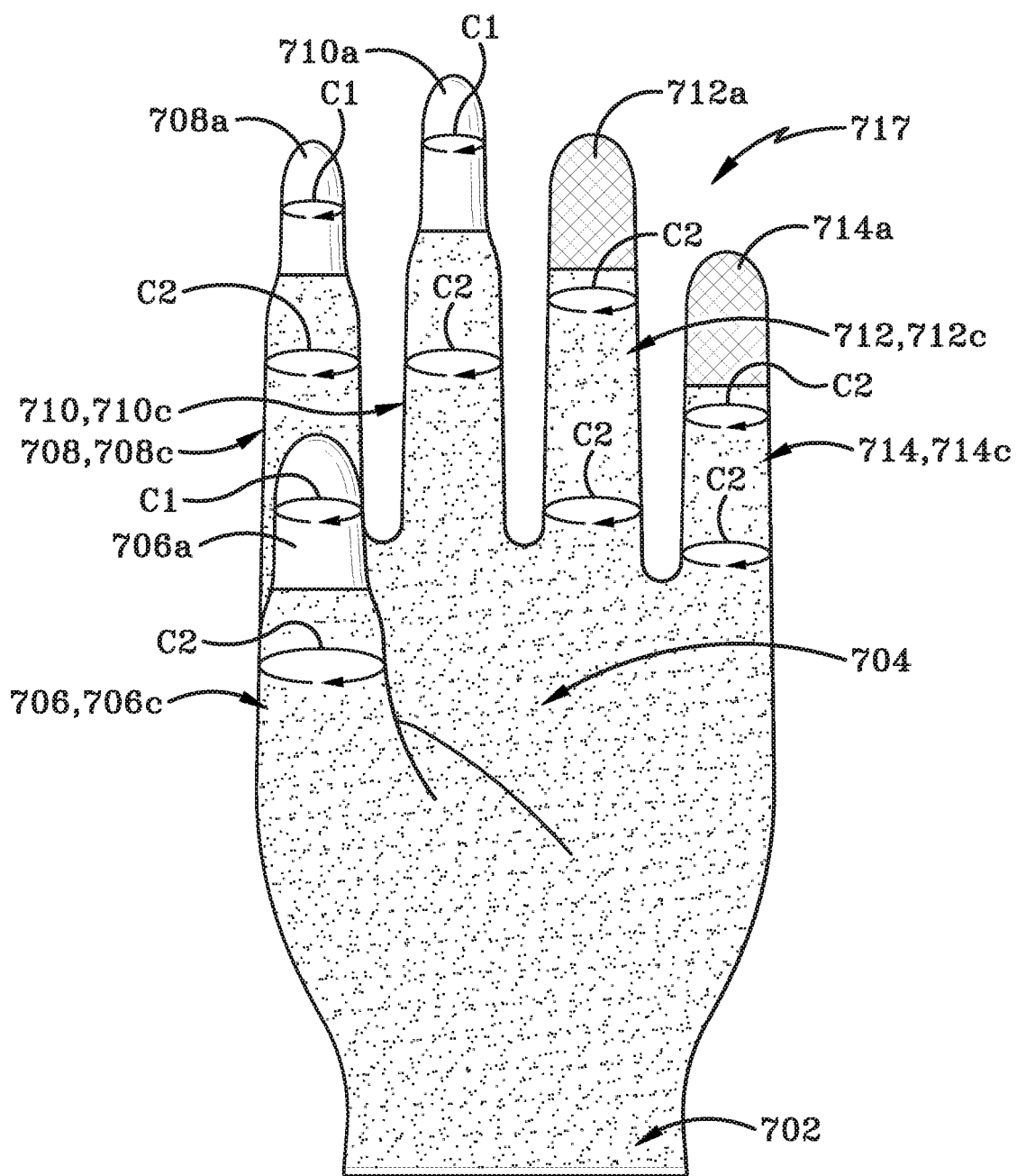
FIG. 19A is a front elevation view of first example of a tenth embodiment of the glove in accordance with an aspect of the present disclosure, shown as a hand-specific glove and showing a reduced circumference fingertip region in the thumb region, index finger region, and middle finger region, as well as areas of the glove that are differently textured; n in addition to the tapered middle and index finger regions.
Figure 19B:
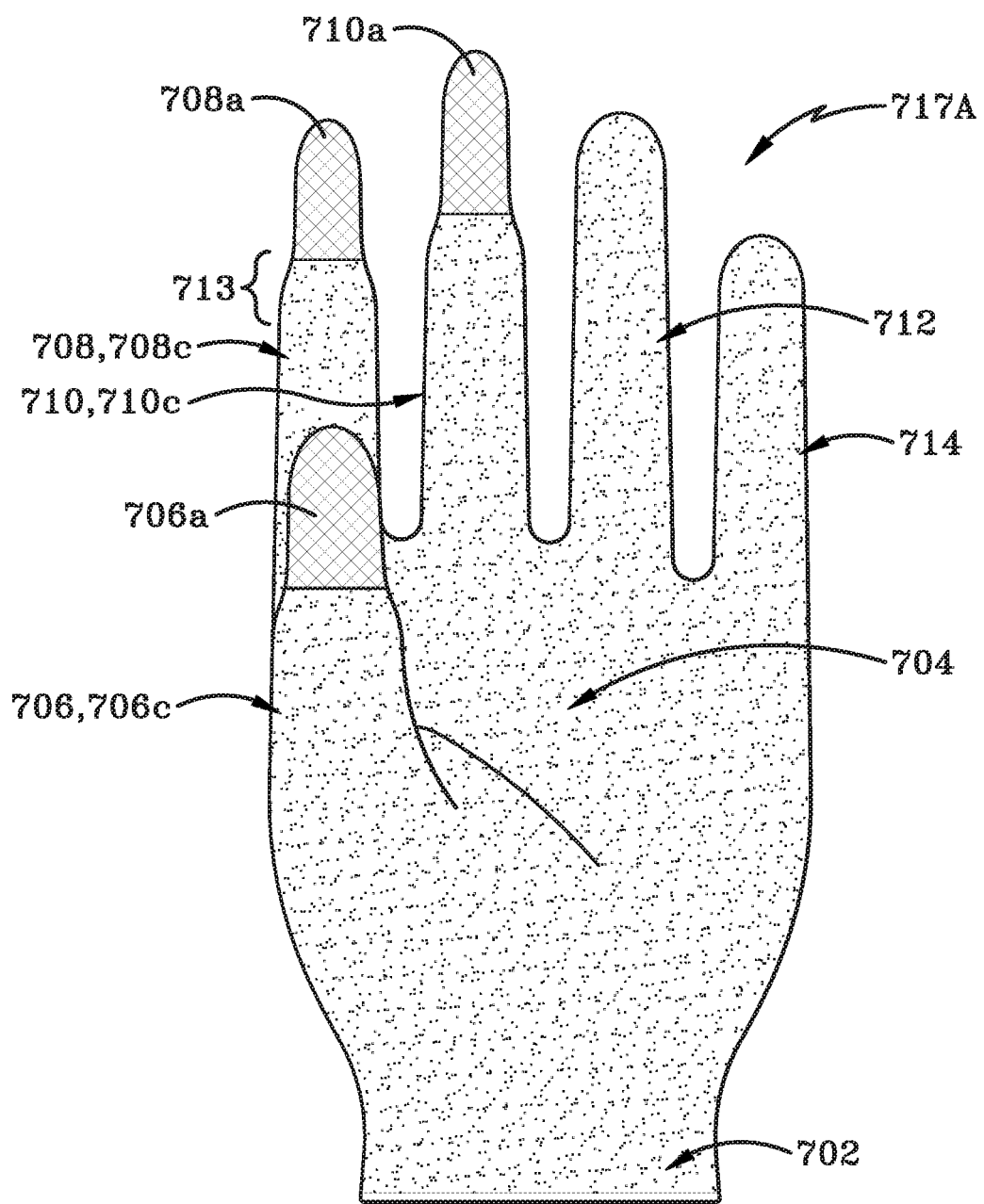
FIG. 19B is a front elevation view of second example of the tenth embodiment shown as a hand-specific glove and showing a reduced circumference fingertip region in the thumb region, index finger region, and middle finger region, as well as areas of the glove that are differently textured.
Figure 19C:
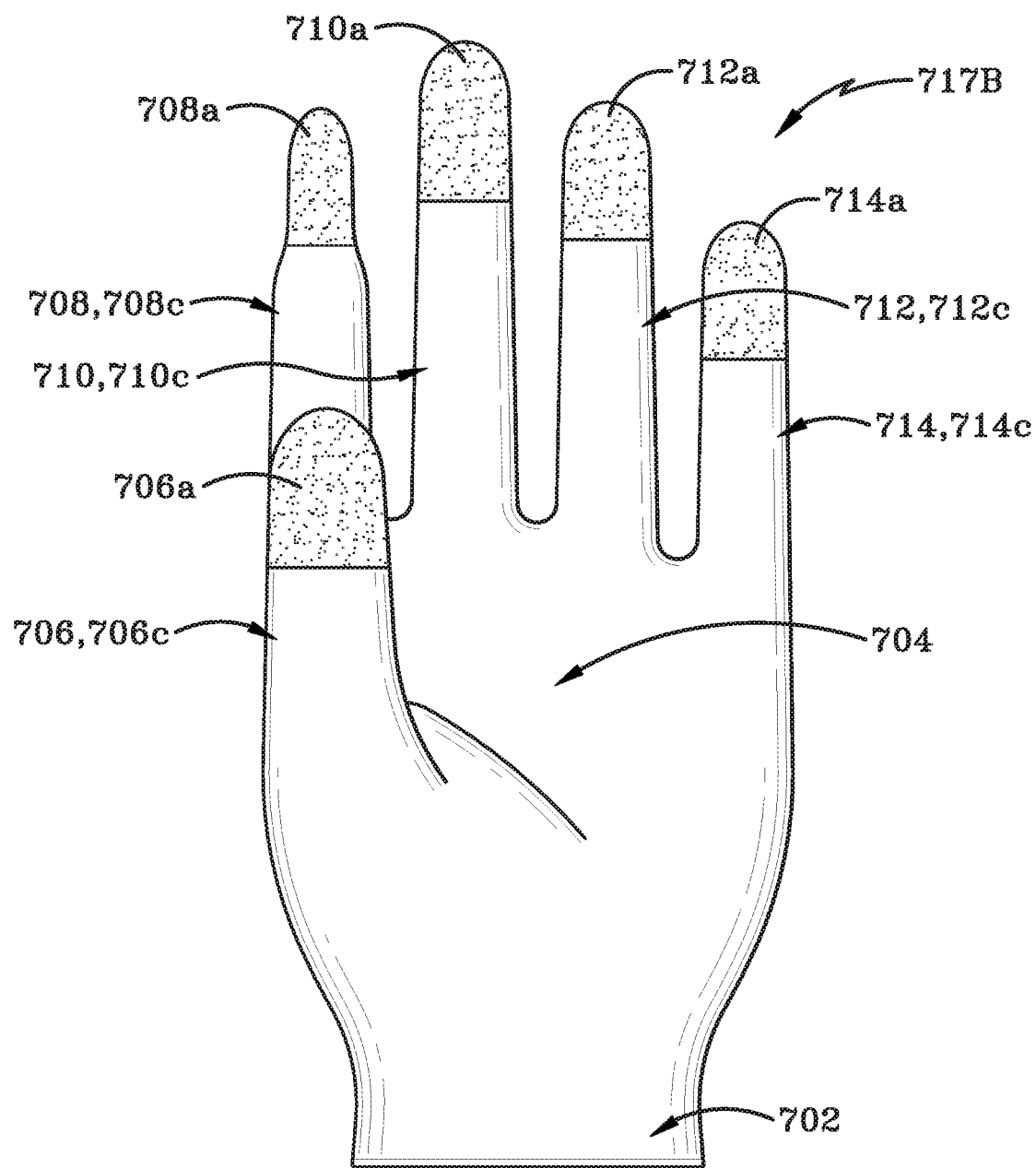
FIG. 19C is a front elevation view of third example of the tenth embodiment shown as a hand-specific glove and showing a reduced circumference fingertip region in the index finger region as well as areas of the glove that are smooth or differently textured.

FIG. 19A to 19C show additional examples of the eighth embodiment of gloves in accordance with the present disclosure, generally indicated as glove 717. Glove 717 is illustrated as a hand-specific glove that includes a wrist region 702, palm region 704, thumb region 706, index finger region 708, middle finger region 710, ring finger region 712, and little finger region 714. Collectively, each of the gloves shown in FIGS. 19A-19C may be substantially identical to one of the gloves 517-517D that are illustrated in one of FIGS. 17A-17E except for the positioning of various smooth and textured areas on the glove 717. FIGS. 19A through 19C are provided as examples of utilizing different combinations of one or more smaller circumference fingertip regions, with none, one or more fingertip regions that are of generally the same circumference as the circumference of associated remaining portions; along with utilizing smooth and/or textured areas. Gloves 717 may include one or more fingertip regions 706a, 708a, 710a, 712a, 714a that are of a smaller circumference than the remaining portion of the associated thumb region 706, index finger region 708, middle finger region 710, ring finger region 712, and little finger region 714. None, one, or more of fingertip regions 706a through 714a may be of generally a same circumference as the associated remaining portion of the thumb region 706, index finger region 708, middle finger region 710, ring finger region 712, and little finger region 714. In each finger region or thumb region that has a fingertip region that is of a reduced or smaller circumference than the circumference of the associated remaining portion, a step-down region similar to region 613 (FIG. 18A) is provided. One such exemplary step-down region 713 is identified in FIG. 19B.

Gloves 717 may differ from gloves 517 in that they show different exemplary combinations of smooth areas and areas that are provided with a first texture or with a second texture. (Even third or fourth textures may be utilized if desired.) The gloves illustrated in FIGS. 19A and 19B have three fingertip regions 706a, 708a, 710a that are of a smaller circumference than the associated remaining portions 706c, 708c, 710c, while the other two fingertip regions 712a, 714a are of substantially a same circumference as the associated remaining portions 712c, 714c.

FIG. 19A shows glove 717 where each of the fingertip regions 706a, 708a and 710a of the thumb region 706, index finger region 708 and middle finger region 710 are of a smaller circumference "C1" and diameter relative to the circumference "C2" of a remaining portion 706c, 708c, and 710c of the respective one of each of the thumb region 706, index finger region 708 and middle finger region 710. It will be understood that the circumferences of the reduced or smaller circumference fingertip regions are indicated by the single reference number "C1" but the use of the single reference number is not intended to imply that the circumferences of these fingertip regions are all of the same size. Similarly, it should be understood that the circumferences of the remaining portions are indicated by the single reference number "C2" but the use of the single reference number is also not meant to imply that the circumferences of the remaining portions are all of the same size.

The circumferences of the various fingertip regions 706a, 708a, 710a, 712a, 714a are measured around an exterior surface of the respective thumb region 706, index finger region 708, middle finger region 710, ring finger region 712, and little finger region 714. The circumference is measured at an orientation of right angles relative to a length of the respective thumb region or finger region 706, 708, 710. (The length of the thumb region or any finger region is measured from a tip of the respective thumb region or finger region down to palm region 704.) It should be understood that in all embodiments of the gloves disclosed in this document, the circumferences of the fingertip regions and the remaining portions are measured in this same manner.

The reduced or smaller dimensions (i.e., circumference and diameter) of fingertip regions 706a, 708a, 710a may ensure that the material or film of each fingertip region 706a, 708a, and 710a will tend to become thinner and be pulled tightly around the tips of the user's thumb, index, and middle fingers, thus maintaining tactile sensitivity therein.

FIG. 19A further illustrates that the smaller circumference fingertip regions 706c, 708c, 710c are all smooth (i.e., free of texture). Fingertip regions 712a, 714a are not of a smaller circumference than the associated remaining portions 712c, 714c and fingertip regions 712a, 714a are provided with a first texture. The rest of glove 717 is provided with a second texture.

FIG. 19B shows a glove 717A that is substantially identical to glove 717 except that the fingertip regions 706a, 708a, 710a are all provided with a first texture and the rest of the glove 717 is provided with a second texture. In particular, the gripping surfaces of fingertip regions 706a, 708a, and 710a on glove 717A are textured with the first texture (in this instance a diamond pattern texture). The gripping surfaces of the fingertip regions 706a, 708a, 710a are those portions of the surface that would tend to typically contact an object if the user holds or picks up the object while wearing glove 717A. The rest of the glove 717A, including the remaining portions of fingertip regions 706a, 708a, 710a may be textured with a sand-type texture. The texturing on fingertip regions 706a, 708a, 710a helps a user to better grip articles and objects than if the fingertip regions 706a, 708a, 710a were smooth. Because of the reduced or smaller circumferences of fingertip regions 706a, 708a, 710a the glove material in these regions may tend to be pulled thin and taut over a tip of the user's thumb or associated finger because these regions are under tension. The material on the rest of the glove is not thinned because it is not under tension. The thinning of the material aids in ensuring that tactile sensitivity is maintained in the thumb, index, and middle fingers while the user's gripping ability while wearing glove 717A is enhanced because of the texturing. The specific patterns selected for the first texture and the second texture may be chosen based on the specific purpose or arena in which glove 710 is to be utilized.

FIG. 19C shows a glove 717B where only a single fingertip region (706a of index finger region 706) is of a smaller or reduced circumference than the circumference of the remaining portion 706c thereof. The other four fingertip regions 708a, 710a, 712a, 714a are of the type that is generally of a same circumference as the associated remaining portions 708c, 710c, 712c, and 714c. In this glove 717B, all of the fingertip regions 706a, 708a, 710a, 712a, 714a are provided with a first texture, while the rest of glove 717 is smooth.

Although not specifically illustrated herein, it will be understood that in a similar fashion, only two smaller circumference fingertip regions, or four smaller circumference fingertip regions, or five smaller circumference fingertip regions may be provided on gloves 717, 717A, 717B. The other fingertip regions may not be of the type that is of a smaller circumference relative to the associated remaining portion. In each instance, some or all of the smaller circumference fingertip regions may be smooth, while in other instances they may be textured with a first texture, a second texture, or even a third texture. The rest of the glove may be provided with various areas having a same texture as the fingertip regions or a different texture relative thereto. Other areas may be smooth (particularly if some or all of the fingertip regions are textured). Any desired combination of smoothness, texturing with a first texture or with a second texture or with a third texture may be utilized in glove 717, 717A, 717B in any combination with any number of smaller circumference or generally the same circumference fingertip regions.

The dimensions of the fingertip regions 706a, 708a, 710a may be reduced or made smaller by from about 1% up to about 20% (and preferably from about 3% up to about 10%) relative to the associated remaining portion 710 and relative to the circumference of a fingertip region in a standard size gloves. This reduction in the dimensions of the fingertip regions helps ensure that the glove film/material is thinned and stretched to the point that the film/material fits tightly around the tips of the user's thumb, index and middle fingers. The film needs to be pulled tight enough to ensure that even a faint pulse may be detected through the film but the film should not be stretched so tight that the gloves are restrictive or uncomfortable to wear. The tightly pulled material or film will tend to apply pressure to the user's thumb or fingertip and ensures that the user can more easily and readily locate even a faint pulse in a patient than if the glove material in the fingertip regions was only fitted loosely around the user's thumb or fingers. The tightly pulled material or film of thumb region 706 also tends to help the user can more readily grasp and capture a section of a patient's skin between their thumb and index finger in order to locate a vein when performing procedures such as inserting a catheter.

FIGS. 20A through 20E show an eleventh embodiment of a glove in accordance with the present disclosure, generally indicated at 817. Glove 817 includes a wrist region 802, palm region 804, thumb region 806, index finger region 808, middle finger region 810, ring finger region 812, and little finger region 814. Gloves 817 may include one or more fingertip regions 806a, 808a, 810a, 812a, 814a that are of a smaller circumference than the remaining portion of the associated thumb region 806, index finger region 808, middle finger region 810, ring finger region 812, and little finger region 814. One or more of the fingertip regions 806a through 814a may not have a smaller circumference than the remaining portion of the associated thumb region 806, index finger region 808, middle finger region 810, ring finger region 812, and little finger region 814.

Gloves 817 are substantially identical to gloves 517 shown in FIGS. 17A-17E except that instead of gloves 817 being hand-specific, the gloves 817 are ambidextrous gloves. The smaller circumference fingertip regions on gloves 817 are smooth while the rest of glove 817 is textured. Because glove 817 is an ambidextrous glove, all of the thumb region 806, index finger region 808, middle finger region 810, ring finger region 812 and little finger region 814 are aligned along a same plane. This is different from the hand-specific gloves, such as glove 517 for example, where the index finger region 508, ring finger region 510, middle finger region 512, a little finger region 514 are all aligned along a same plane but the thumb region 506 is located in a different plane.

Figure 20A:
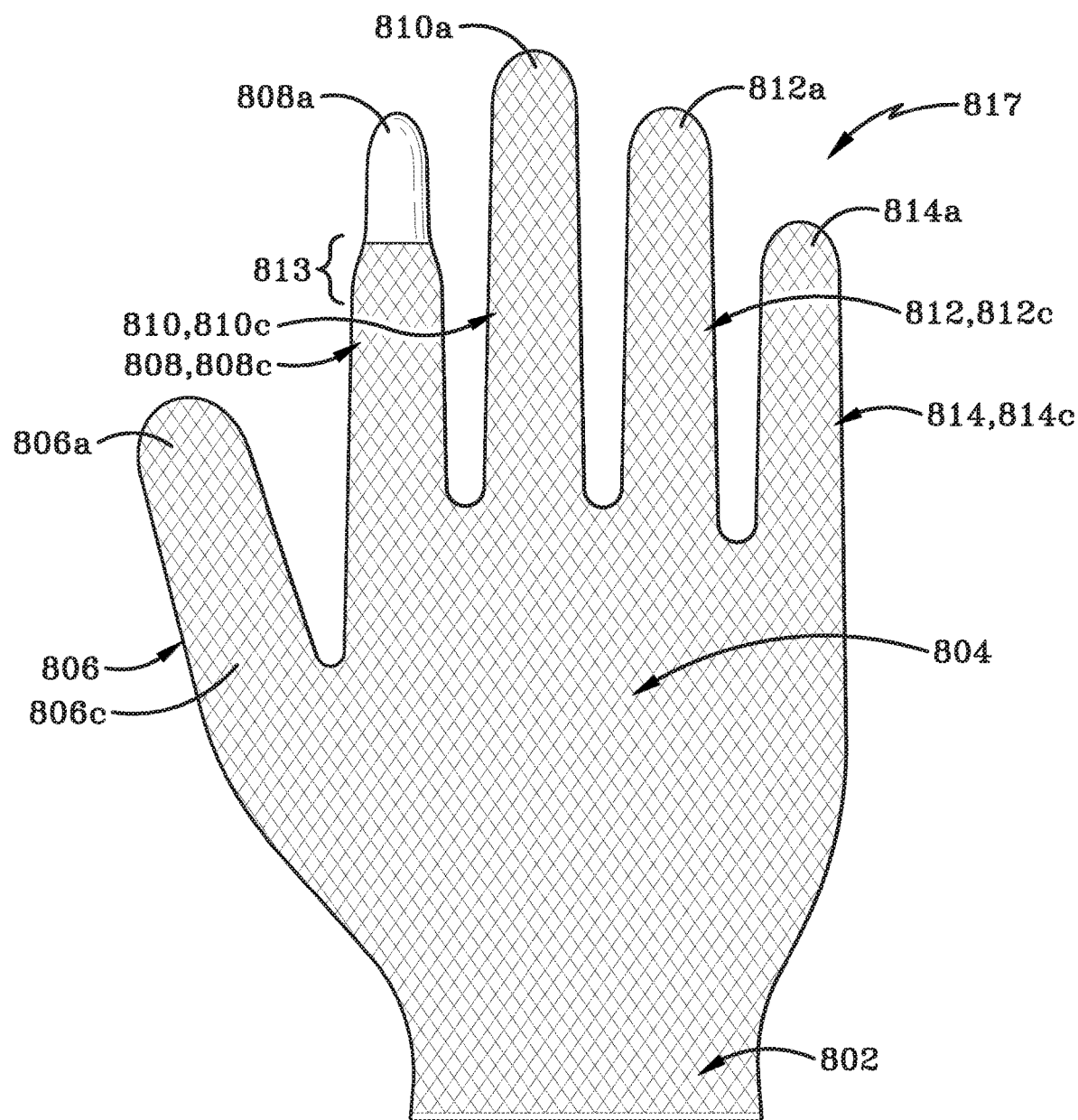
FIG. 20A is a front elevational view of a first example of an eleventh embodiment of a glove in accordance with an aspect of the present disclosure, where the glove is an ambidextrous glove that has texturing on the gripping surfaces of the glove but the fingertip region of the index finger region is of smaller circumference than a remaining portion of the index finger region, is free of texturing and is smooth.

FIG. 20A shows glove 817, where fingertip region 808a is of a reduced circumference relative to a remaining portion 808c of the index finger region 808. All other fingertip regions 806a, 810a, 812a, 814a are of generally a same size as the remaining portions 806c, 810c, 812c, and 814c. Fingertip region 808a is smooth while the rest of the glove 817 is textured.

Figure 20B:
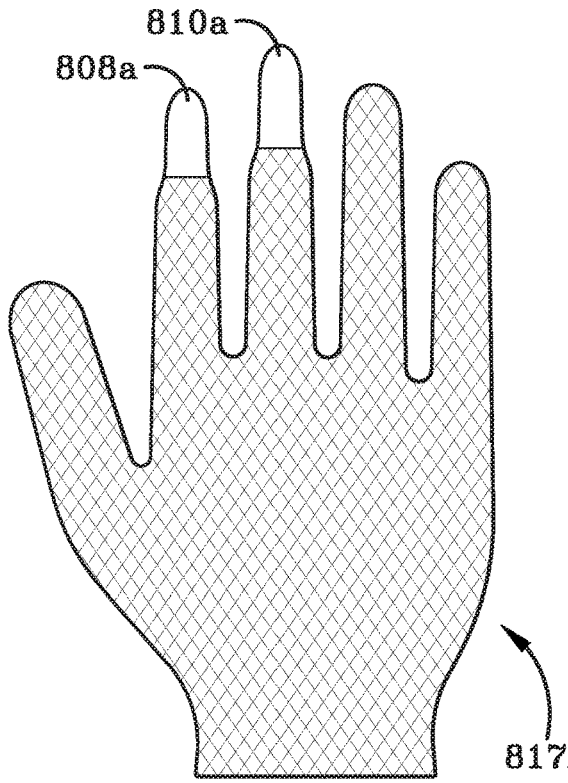
FIG. 20B is a front elevational view of a second example of the eleventh embodiment where the glove is an ambidextrous glove that has texturing on the gripping surfaces of the glove and the fingertip regions of the index finger region and middle finger region are of a smaller circumference than a remaining portion of the associated index finger region and middle finger region and are free of texturing and are smooth.

FIG. 20B shows glove 817A, where fingertip regions 808a, 810a are of a reduced circumference relative to an associated remaining portion 808c, 810c of the index finger region 808 and middle finger region 810. All other fingertip regions 806a, 812a, 814a are of generally a same size as the remaining portions 806c, 812c, and 814c. Fingertip regions 808a, 810a are smooth while the rest of the glove 817A is textured. Fingertip regions 808a, 810a therefore have a different appearance to the rest of glove 817A.

Figure 20C:
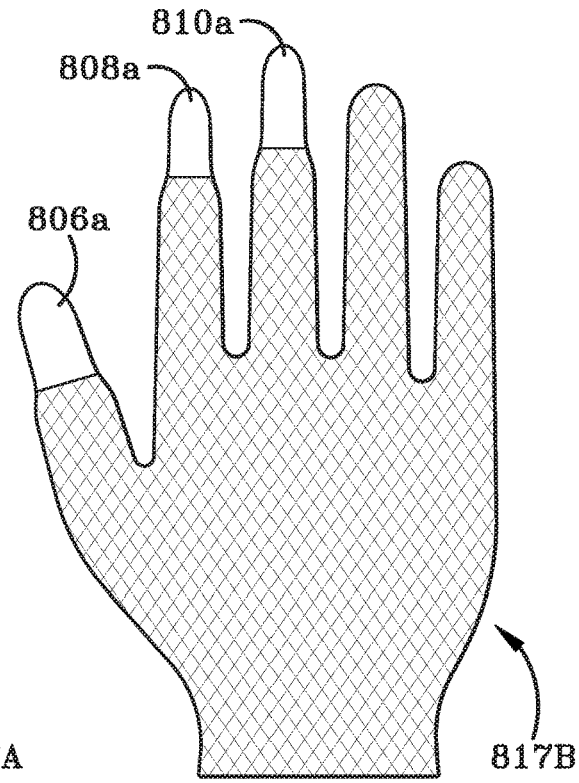
FIG. 20C is a front elevational view of a third example of the eleventh embodiment where the glove is an ambidextrous glove that has texturing on the gripping surfaces of the glove and the fingertip regions of the thumb region, index finger region, and middle finger region are of smaller circumferences than the remaining portions of the associated thumb region or finger regions and are free of texturing and are smooth.

FIG. 20C shows glove 817B, where fingertip regions 806a, 808a, 810a are of a reduced circumference relative to an associated remaining portion 806c, and 808c, 810c of the thumb region 806, index finger region 808, and middle finger region 810. All other fingertip regions 812a, 814a are of generally a same size as the remaining portions 812c, 814c. Fingertip regions 806a, 808a, 810a are smooth while the rest of the glove 817B is textured. In particular, FIG. 20C shows that wrist region 802, palm region 804, ring finger region 812, little finger region 814 and remaining portions 806c, 808c, and 810c of thumb region 806, index finger region 808, and middle finger region 810, respectively, are textured. Fingertip regions 806a, 808a, and 810a of thumb region 806, index finger region 808, and middle finger region 810 are free of texture.

It should be noted that because glove 817B is an ambidextrous glove, the front surface and the back surface of each of the wrist region 802, palm region 804, ring finger region 812, little finger region 814 and remaining portions 806c, 808c, and 810c of thumb region 806, index finger region 808, and middle finger region 810, may all be textured. Similarly, front and back surfaces of fingertip regions 806a, 808a, and 810a may be smooth or free of texture. The same pattern of textured and smooth areas on the front and back surfaces ensures that glove 817 may be used as an ambidextrous glove on either of the left hand or the right hand of the user.

Furthermore, the reduced or smaller circumferences of fingertip regions 806a, 808a, 810a relative to the remaining portions 806c, 808c, and 810c may tend to cause the material of these regions to be pulled thin and taut over a tip of the user's thumb or associated finger, thereby applying pressure thereto. This means that tactile sensitivity is maintained in the thumb, index, and middle fingers. The smooth, un-textured surfaces on fingertip regions 806a, 808a, 810a helps to ensure that medical personnel may readily be able to detect a patient's pulse, even if that pulse is faint.

The specific pattern of texturing shown on the reminder of glove 817B, i.e., on regions other than fingertip regions 806a, 808a, and 810a, is illustrated as being a diamond pattern. It will be understood that other differently configured patterns may be used instead of the diamond pattern. The specific pattern selected may be chosen based on the specific purpose or arena in which glove 817 is to be utilized.

Figure 20D:
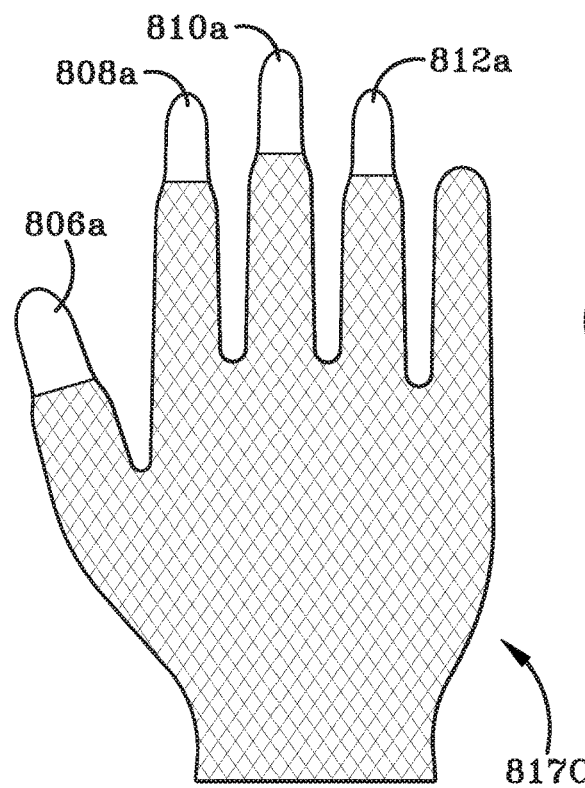
FIG. 20D is a front elevational view of a fourth example of the eleventh embodiment where the glove is an ambidextrous glove that has texturing on the gripping surfaces of the glove and the fingertip regions of the thumb region, index finger region, middle finger region and ring finger region are of smaller circumferences than the remaining portions of the associated thumb region or finger regions and are free of texturing and are smooth.

FIG. 20D shows glove 817C, where fingertip regions 806a, 808a, 810a, 812a are of a reduced circumference relative to an associated remaining portion 806c, 808c, 810c, 812c of the thumb region 806, index finger region 808, middle finger region 810, and ring finger region 812. Fingertip region 814a is of generally a same size as the remaining portions 814c. Fingertip regions 806a, 808a, 810a, 812a are smooth while the rest of the glove 817C is textured. In other exemplary gloves, instead of fingertip region 812a being of a reduced circumference, the fingertip region 814a is of a reduced circumference relative to remaining portion 814c and the fingertip region 812a is of a generally same circumference as remaining portion 812c. In this instance, fingertip region 814a may be smooth and the rest of glove 817D including fingertip region 812a may be textured.

Figure 20E:
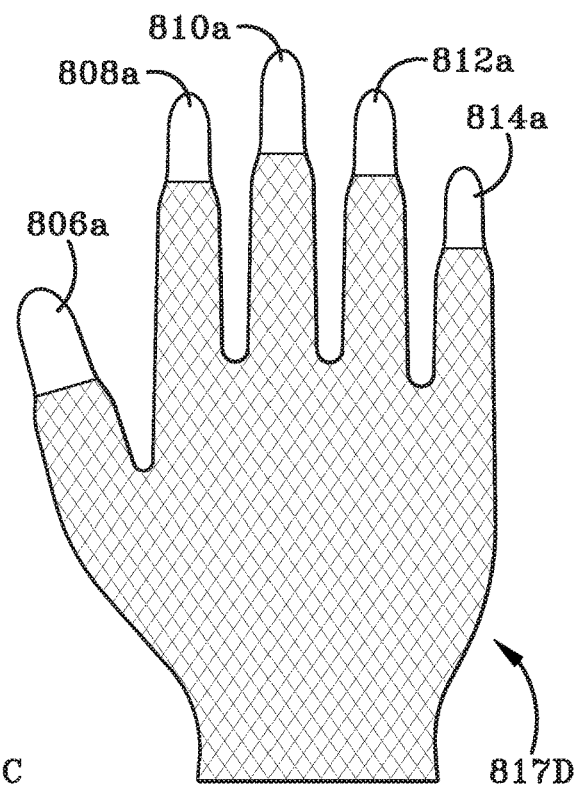
FIG. 20E is a front elevational view of a fifth example of the eleventh embodiment where the glove is an ambidextrous glove that has texturing on the gripping surfaces and all the fingertip regions are of smaller circumferences than the associated thumb region or finger region and are free of texturing and are smooth.

FIG. 20E shows glove 817D, where all five fingertip regions 806a, 808a, 810a, 812a, 814a are of a reduced circumference relative to an associated remaining portion 806c, 808c, 810c, 812c, 814c of the thumb region 806, index finger region 808, middle finger region 810, ring finger region 812, and little finger region 814. Fingertip regions 806a, 808a, 810a, 812a, 814a may be smooth while the rest of the glove 817D is textured.

In each finger region or thumb region of the gloves illustrated in FIGS. 20A-20E that has a fingertip region that is of a reduced or smaller circumference than the circumference of the associated remaining portion, a step-down region similar to region 613 (FIG. 18A) is provided. One such exemplary step-down region 813 is identified in FIG. 20A.

FIGS. 21A through 21E show a twelfth embodiment of a glove in accordance with the present disclosure, generally indicated at 917. Glove 917 includes a wrist region 902, palm region 904, thumb region 906, index finger region 908, middle finger region 910, ring finger region 912, and little finger region 914. Gloves 917 may include one or more fingertip regions 906a, 908a, 910a, 912a, 914a that are of a smaller circumference than the remaining portion of the associated thumb region 906, index finger region 908, middle finger region 910, ring finger region 912, and little finger region 914. One or more of the fingertip regions 906a through 914a may not have a smaller circumference than the remaining portion of the associated thumb region 906, index finger region 908, middle finger region 910, ring finger region 912, and little finger region 914.

Gloves 917 are substantially identical to the gloves shown in FIGS. 20A-20E except that the smaller circumference fingertip regions are textured and the rest of glove is smooth.

Figure 21A:
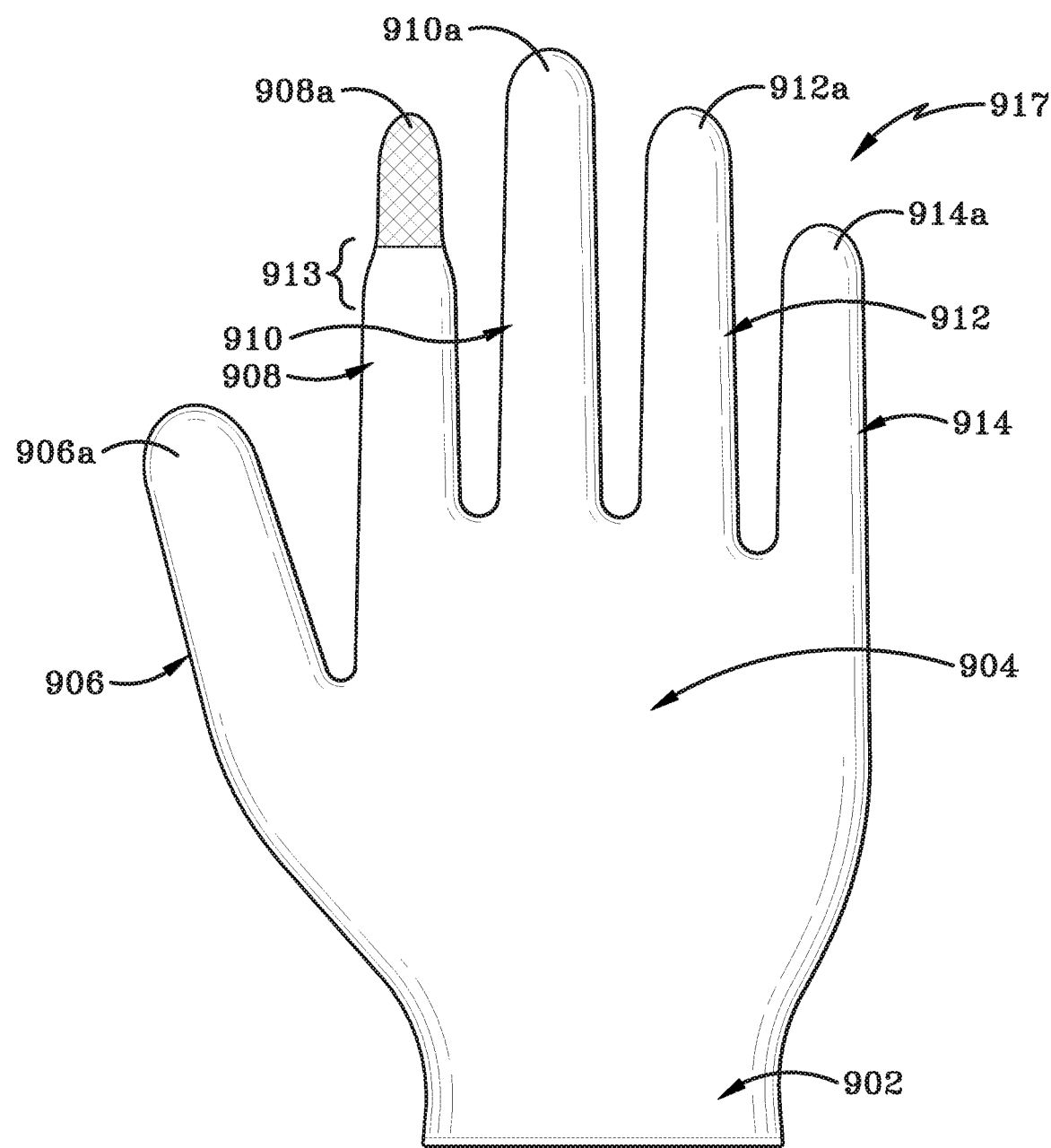
FIG. 21A is a front elevational view of a first example of a twelfth embodiment of a glove in accordance with an aspect of the present disclosure, where the glove is an ambidextrous glove that is smooth or non-textured on the gripping surfaces of the glove and the fingertip region of the index finger region is of smaller circumference than a remaining portion of the index finger region and is textured.

FIG. 21A shows glove 917, where fingertip region 908a is of a reduced circumference relative to a remaining portion 908c of the index finger region 908. All other fingertip regions 906a, 910a, 912a, 914a are of generally a same size as the remaining portions 906c, 910c, 912c, and 914c. Fingertip region 908a is textured while the rest of the glove 917 is smooth or non-textured.

Figure 21B:
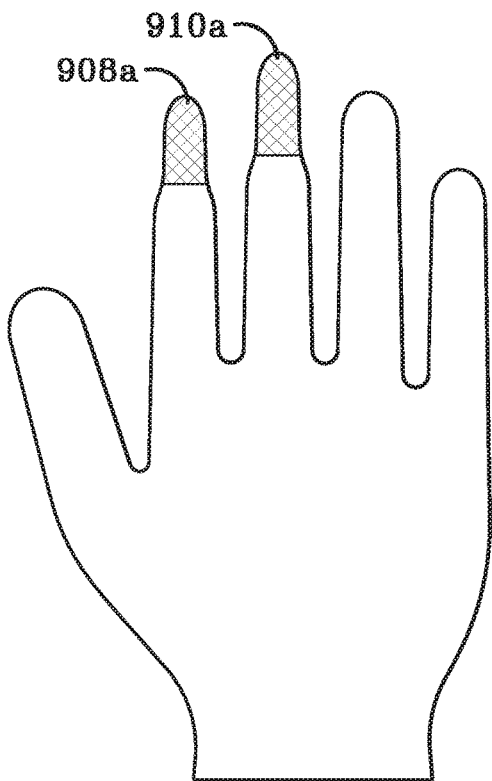
FIG. 21B is a front elevational view of a second example of the twelfth embodiment where the glove is an ambidextrous glove that is smooth or non-textured on the gripping surfaces of the glove and the fingertip regions of the index finger region and middle finger region are of a smaller circumference than a remaining portion of the associated index finger region and middle finger region and are textured.

FIG. 21B shows glove 917A, where fingertip regions 908a, 910a are of a reduced circumference relative to an associated remaining portion 908c, 910c of the index finger region 908 and middle finger region 910. All other fingertip regions 906a, 912a, 914a are of generally a same size as the remaining portions 906c, 912c, and 914c. Fingertip regions 908a, 910a are textured while the rest of the glove 917A is smooth or non-textured.

Figure 21C:
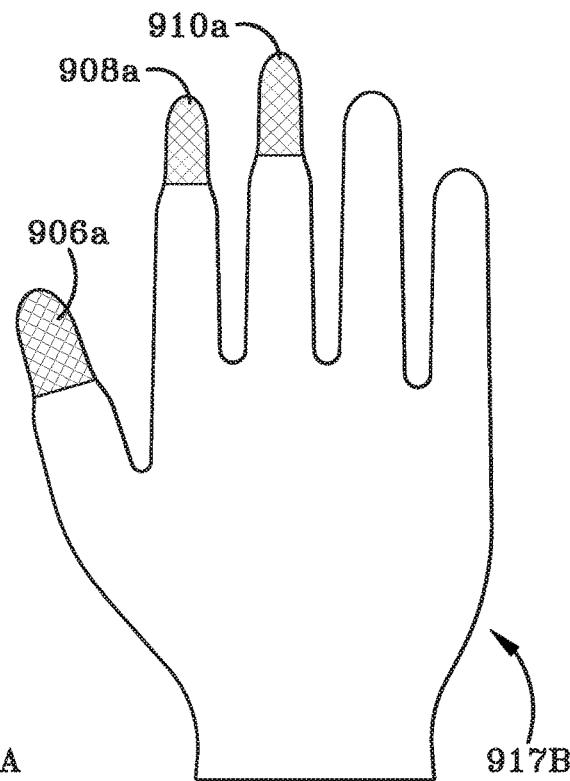
FIG. 21C is a front elevational view of a third example of the twelfth embodiment where the glove is an ambidextrous glove that is smooth or non-textured on the gripping surfaces of the glove and the fingertip regions of the thumb region, index finger region, and middle finger region are of smaller circumferences than the remaining portions of the associated thumb region or finger regions and are textured.

FIG. 21C shows glove 917B, where fingertip regions 906a, 908a, 910a are of a reduced circumference relative to an associated remaining portion 906c, and 908c, 910c of the thumb region 906, index finger region 908, and middle finger region 910. All other fingertip regions 912a, 914a are of generally a same size as the remaining portions 912c, 914c. Fingertip regions 906a, 908a, 910a are textured while the rest of the glove 917B is smooth or non-textured. In particular, FIG. 21C shows that wrist region 902, palm region 904, ring finger region 912, little finger region 914 and remaining portions 906c, 908c, and 910c of thumb region 906, index finger region 908, and middle finger region 910, respectively, are smooth. Fingertip regions 906a, 908a, and 910a of thumb region 906, index finger region 908, and middle finger region 910 are textured.

It should be noted that because glove 917B is an ambidextrous glove, the front surface and the back surface of each of the wrist region 902, palm region 904, ring finger region 912, little finger region 914 and remaining portions 906c, 908c, and 910c of thumb region 906, index finger region 908, and middle finger region 910, may all be smooth or non-textured. Similarly, front and back surfaces of fingertip regions 906a, 908a, and 910a may be textured. The same pattern of textured and smooth areas on the front and back surfaces of any of the gloves 917-917D may be used as an ambidextrous glove on either of the left hand or the right hand of the user.

Furthermore, the reduced or smaller circumferences of fingertip regions 906a, 908a, 910a relative to the remaining portions 906c, 908c, and 910c may tend to cause the material of these regions to be pulled thin and taut over a tip of the user's thumb or associated finger, thereby applying pressure thereto. This means that tactile sensitivity is maintained in the thumb, index, and middle fingers. The textured surfaces on fingertip regions 906a, 908a, 910a helps to ensure that medical personnel may readily be able to grip onto objects to be held, such as a patient's skin when try to find a vein.

The texturing shown on glove 917B, is illustrated as being a diamond pattern. It will be understood that other differently configured patterns may be used instead of the diamond pattern. The specific pattern selected may be chosen based on the specific purpose or arena in which glove 917B is to be utilized.

Figure 21D:
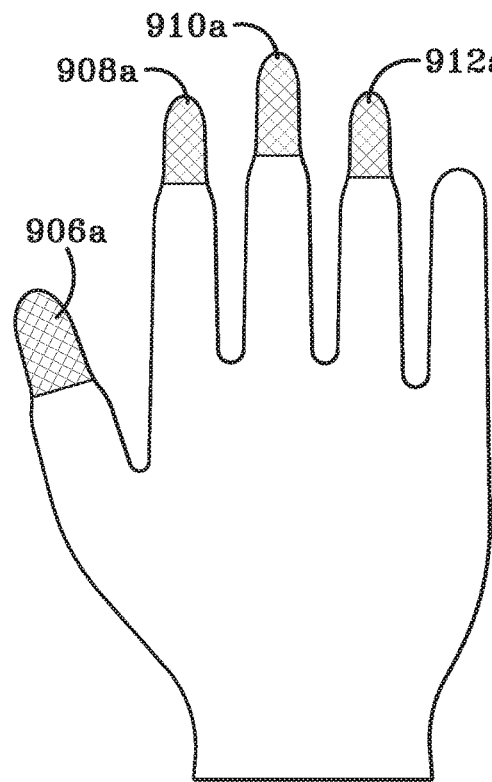
FIG. 21D is a front elevational view of a fourth example of the twelfth embodiment, where the glove is an ambidextrous glove that is smooth or non-textured on the gripping surfaces of the glove and the fingertip regions of the thumb region, index finger region, middle finger region and ring finger region are of smaller circumferences than the remaining portions of the associated thumb region or finger regions and are textured.

FIG. 21D shows glove 917C, where fingertip regions 906a, 908a, 910a, 912a are of a reduced circumference relative to an associated remaining portion 906c, 908c, 910c, 912c of the thumb region 906, index finger region 908, middle finger region 910, and ring finger region 912. Fingertip region 914a is of generally a same size as the remaining portions 914c. Fingertip regions 906a, 908a, 910a, 912a are textured while the rest of the glove 917C is smooth or non-textured. In other exemplary gloves, instead of fingertip region 912a being of a reduced circumference, the fingertip region 914a is of a reduced circumference relative to remaining portion 914c and the fingertip region 912a is of a generally same circumference as remaining portion 912c. In this instance, fingertip region 914a may be textured and the rest of glove 917D including fingertip region 912a may be smooth or non-textured.

Figure 21E:
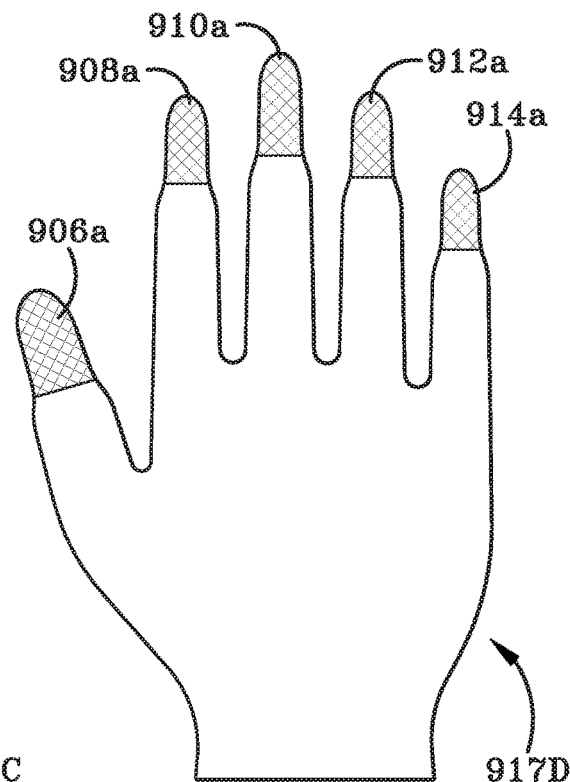
FIG. 21E is a front elevational view of a fifth example of the twelfth embodiment where the glove is an ambidextrous glove that is smooth or non-textured on the gripping surfaces and all the fingertip regions are of smaller circumferences than the associated thumb region or finger region and are textured.

FIG. 21E shows glove 917D, where all five fingertip regions 906a, 908a, 910a, 912a, 914a are of a reduced circumference relative to an associated remaining portion 906c, 908c, 910c, 912c, 914a of the thumb region 906, index finger region 908, middle finger region 910, ring finger region 912, and little finger region 914. Fingertip regions 906a, 908a, 910a, 912a, 914a may be textured while the rest of the glove 917D is smooth or non-textured.

Furthermore, as indicated above, the reduced or smaller circumferences of one or more of fingertip regions 906a, 908a, 910a, 912a, 914a may cause the material of the glove tend to be thinned and pulled taut over a tip of the user's thumb or associated finger. When fingertip regions are pulled taut in this manner they tend to apply pressure to the associated thumb or finger in that part of glove. This means that tactile sensitivity is maintained in the thumb or associated fingers and the user's gripping ability while wearing glove 917 is enhanced by the texture applied to reduced circumference fingertip regions. The texture on fingertip regions helps to ensure that medical personnel may readily be readily grip objects while tactile sensitivity in their thumb and fingers (particularly the index and middle fingers) is maintained. This type of glove 917-917D is also useful in other fields. For example, the glove may be worn by gun enthusiasts where the textured fingertip region 908a, in particular, helps maintain contact with a trigger, for example, but also provides tactile sensitivity to the user.

The specific pattern of texturing shown on the fingertip regions is illustrated as a sand finish or sand texturing. It will be understood that other differently configured patterns may be used instead, such as a diamond pattern. The specific pattern selected may be chosen based on the specific purpose or arena in which glove 917 is to be utilized.

In each finger region or thumb region of the gloves illustrated in FIGS. 21A-21E that has a fingertip region that is of a reduced or smaller circumference than the circumference of the associated remaining portion, a step-down region similar to region 613 (FIG. 18A) is provided. One such exemplary step-down region 913 is identified in FIG. 21A.

Figure 22:
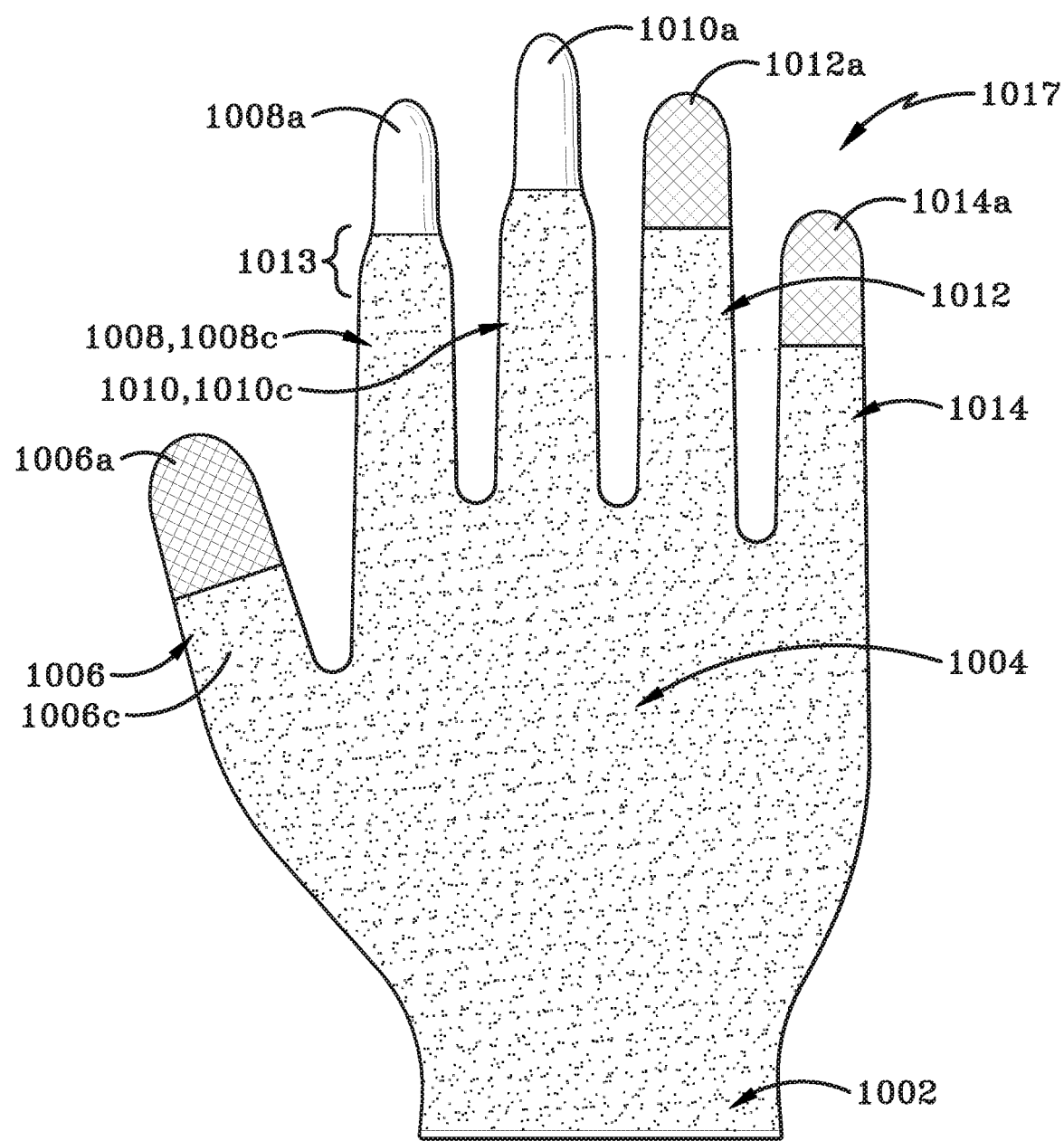
FIG. 22 is a front elevational view of a thirteenth embodiment of a glove in accordance with an aspect of the present disclosure, where the glove is an ambidextrous glove that may include one or more fingertip regions that have reduced circumferences relative to the associated remaining portion of the thumb region or finger region; and that has areas that are smooth or non-textured and other areas that are provided with a first texture, or a second texture or a third texture.

FIG. 22 shows an exemplary thirteenth embodiment of a glove in accordance with the present disclosure, generally indicated at 1017. Glove 1017 is an ambidextrous glove that includes a wrist region 1002, palm region 1004, thumb region 1006, index finger region 1008, middle finger region 1010, ring finger region 1012, and little finger region 1014. Glove 1017 may include one or more fingertip regions 1006a, 1008a, 1010a, 1012a, 1014a that are of a smaller circumference than the remaining portion of the associated thumb region 1006, index finger region 1008, middle finger region 1010, ring finger region 1012, and little finger region 1014. One or more of the fingertip regions 1006a through 1014a may not have a smaller circumference than the remaining portion of the associated thumb region 1006, index finger region 1008, middle finger region 1010, ring finger region 1012, and little finger region 1014 but may rather have generally a same circumference as a remaining portion thereof. Glove 1017 may be substantially identical to any of the gloves 817 or 917 except that some areas glove 1017 may be smooth, some areas may be provided with a first texture, and other areas may be provided with a second texture. By way of example only, FIG. 22 shows glove 1017 with fingertip regions 1006a, 1008a, 1010a that are of smaller circumference relative to the remaining portions 1006c, 1008c, 1010c of thumb region 1006, index finger region 1008, and middle finger region 1010. Fingertip regions 1006a, 1008a, 1010a are textured with a first texture. Fingertip regions 1012a, 1014a are not of a smaller circumference than remaining portions 1012c, 1014c and are smooth or non-textured. The rest of glove 1017 may be provided with a second texture. It will be understood that any desired combination of texturing or smoothness, reduced circumference fingertip regions, and non-reduced circumference fingertip regions may be utilized in glove 1017.

In each finger region or thumb region of the glove discussed above and illustrated in FIG. 22 that has a fingertip region that is of a reduced or smaller circumference than the circumference of the associated remaining portion, a step-down region similar to region 613 (FIG. 18A) is provided. One such exemplary step-down region 1013 is identified in FIG. 22.

FIGS. 23A through 23E show a fourteenth embodiment of a glove 1117 in accordance with an aspect of the present disclosure. Glove 1117 is illustrated as a hand-specific glove that includes wrist region 1102, palm region 1104, thumb region 1106, index finger region 1108, middle finger region 1110, ring finger region 1112, and little finger region 1114. Collectively, each of these gloves 1117 shown in FIGS. 23A-23E may be considered to be an example of a glove accordance with the present disclosure that includes fingertip regions 1106a, 1108a, 1110a, 1112a, 1114a that are of a bullet-tip configuration. The bullet-tip configuration is one where one or more of the fingertip regions is of a smaller circumference than a circumference of the associated remaining portion 1106c, 1108c, 1110c, 1112c, 1114c of the thumb region 1106, index finger region 1108, middle finger region 1110, ring finger region 1112, and little finger region 1114. A flared skirt extends between the bullet-tip type fingertip region and the associated remaining portion. The skirt tapers in circumference from the remaining portion to the associated fingertip region. The skirt is of a smallest circumference proximate the bullet-tip and is of a largest circumference proximate the associated remaining portion. Additionally, the circumference of the bullet-tip is substantially constant from the skirt to substantially adjacent the end 1106e, 1108e, 1110e, 1112e, or 1114e of the associated thumb region 1106, index finger region 1108, middle finger region 1110, ring finger region 1112, or little finger region 1114. FIGS. 23A to 23E show examples of glove 1117 that are entirely smooth or non-textured. It will be understood however that in other instances, the gloves shown in FIGS. 23A to 23E may be entirely textured. In yet other instances, the bullet-tip fingertip regions may be smooth (i.e., non-textured) and the rest of the glove may be textured. In yet other instances, the bullet-tip fingertip regions may be textured and the rest of the glove may be smooth (i.e., non-textured).

Figure 23A:
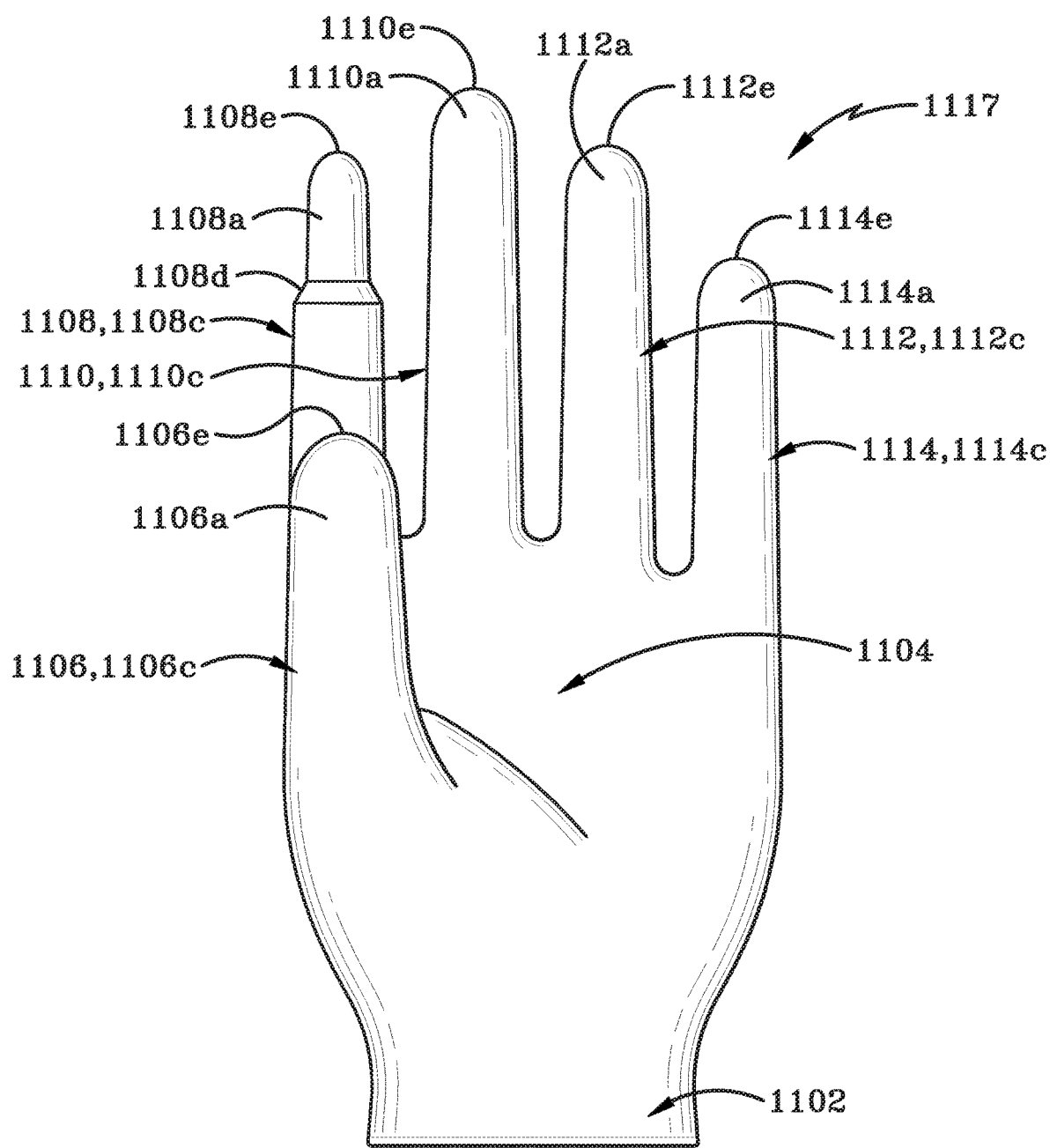
FIG. 23A is a front elevational view of a first example of a fourteenth embodiment of a glove in accordance with an aspect of the present disclosure, where the glove is a hand-specific glove that has a bullet-tip type fingertip region provided on the index finger region; and showing a skirt extending between the fingertip region and a remaining portion of the index finger region; and where the entire glove is smooth and non-textured.

FIG. 23A shows a first example glove 1117 having a bullet-tip fingertip region 1108a on index finger region 1108. A skirt 1108d extends between fingertip region 1108a and remaining portion 1108c. Fingertip region 1108a is of a substantially constant circumference from skirt 1108d to end 1108e. Similarly, the circumference of the remaining portion 1108c is substantially constant from skirt 1108d to palm region 1104. The circumference of remaining portion 1108c is larger than the reduced circumference of fingertip region 1108. Skirt 1108d acts as a step-down region between fingertip region 1108a and remaining portion 1108c. The step-down region may be more sharply pronounced than the step-down regions of previous embodiments. Step-down region, i.e., skirt 1108d tapers in circumference from the circumference of the remaining portion 1108c to the circumference of fingertip region 1108a. The fingertip region 1108a of index finger region 1108 may be smooth. The rest of glove 1117 may also be smooth.

Figure 23B:
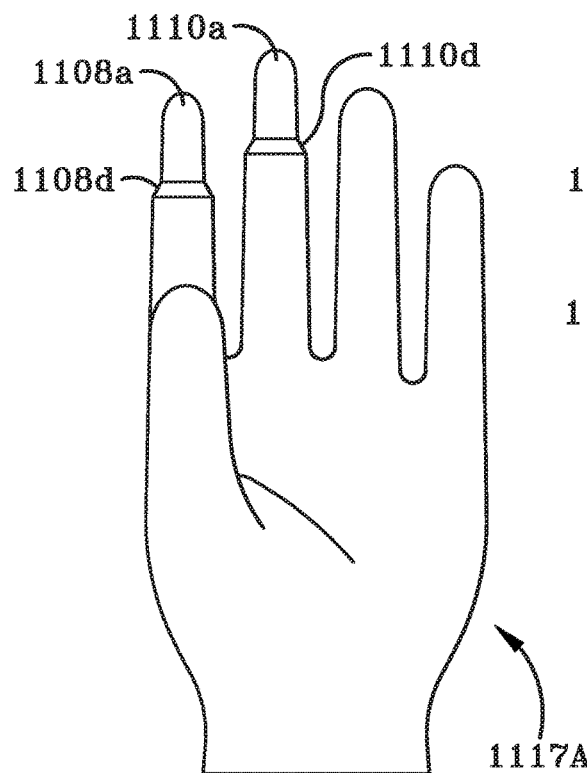
FIG. 23B is a front elevational view of a second example of the fourteenth embodiment where the glove is a hand-specific glove having a bullet-tip type fingertip region provided on the index finger region and middle finger region, and having a skirt between the bullet-tip and remaining portion thereof.

FIG. 23B shows glove 1117A having bullet-tip fingertip regions 1108a, 1110a on index finger region 1108 and on middle finger region 1110. Skirts 1108d, 1110d extend between the respective fingertip regions 1108a, 1110a and the associated remaining portions 1108c, 1110c. The entire glove 1117A may be smooth and non-textured.

Figure 23C:
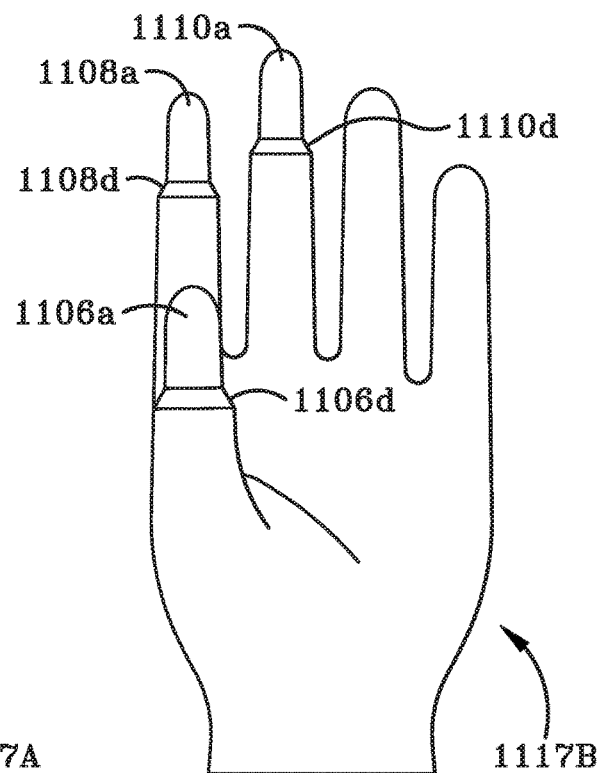
FIG. 23C is a front elevational view of a third example of the fourteenth embodiment where the glove is a hand-specific glove having a bullet-tip type fingertip region provided on the thumb region, index finger region, and middle finger region, and having a skirt between the bullet-tip and remaining portion thereof.

FIG. 23C shows glove 1117B having bullet-tip fingertip regions 1106a, 1108a, 1110a on thumb region 1106, index finger region 1108, and middle finger region 1110. Skirts 1106d, 1108d, 1110d extend between the respective fingertip regions 1106a, 1108a, 1110a and the associated remaining portions 1106c, 1108c, 1110c. The entire glove 1117B may be smooth and non-textured.

Figure 23D:
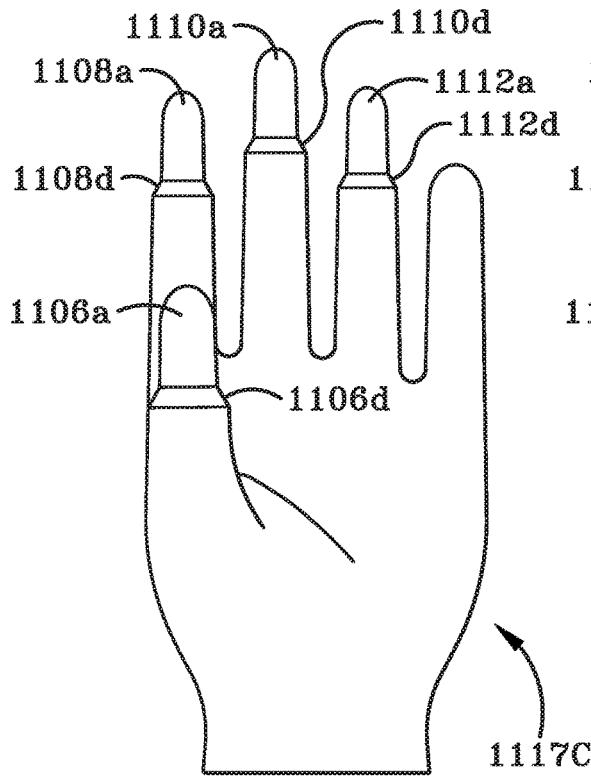
FIG. 23D is a front elevational view of a fourth example of the fourteenth embodiment where the glove is a hand-specific glove having a bullet-tip type fingertip region provided on the thumb region, index finger region, middle finger region, and ring finger region, and having a skirt between the bullet-tip and remaining portion thereof.

FIG. 23D shows glove 1117C having bullet-tip fingertip regions 1106a, 1108a, 1110a, 1112a. Skirts 1106d, 1108d, 1110d, 1112d extend between the respective fingertip regions 1106a, 1108a, 1110a, 1112a and the associated remaining portions 1106c, 1108c, 1110c, and 1112c. The entire glove 1117C may be smooth and non-textured. Although not illustrated herein, it will be understood that fingertip region 1114a of little finger region 1114 may be formed as a bullet-tip fingertip region 1114a instead of fingertip region 1112a being of a bullet-tip configuration. The entire glove 1117C may be smooth.

Figure 23E:
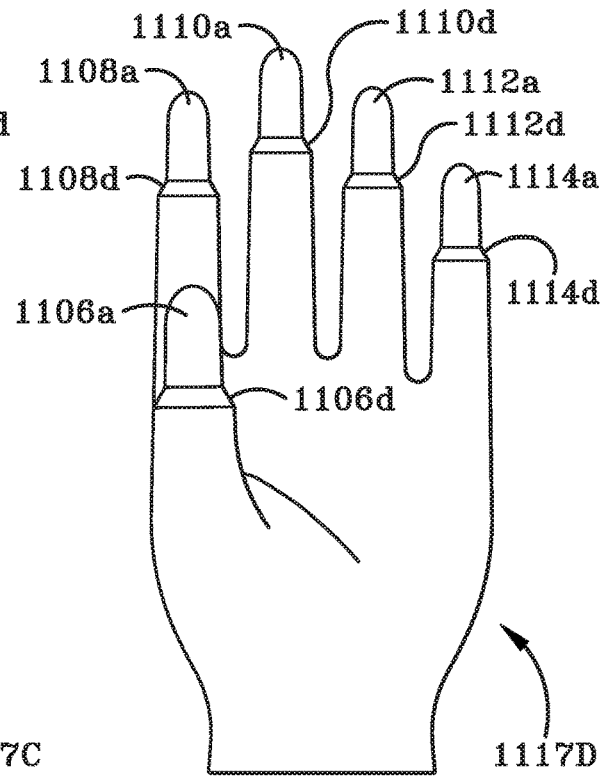
FIG. 23E is a front elevational view of a fifth example of the fourteenth embodiment where the glove is a hand-specific glove having a bullet-tip type fingertip region provided on all five of the thumb region, index finger region, middle finger region, ring finger region, and little finger region, and having a skirt between the bullet-tip and remaining portion thereof.

FIG. 23E shows glove 1117D having bullet-tip fingertip regions 1106a, 1108a, 1110a, 1112a, 1114a on all five of the thumb region 1106, index finger region 1108, middle finger region 1110, ring finger region 1112, and little finger region 1114. Skirts 1106d, 1108d, 1110d, 1112d, 1114d extend between the respective fingertip regions 1106a, 1108a, 1110a, 1112a, 1114a and the associated remaining portions 1106c, 1108c, 1110c, 1112c, 1114c. The entire glove 1117D may be smooth and non-textured.

FIGS. 23A to 23E show gloves 1117 where one or more of the fingertip regions are formed in a bullet-tip configuration and that bullet-tip is connected by a skirt to the remaining portion of that thumb region or finger region. One or more of the non-bullet-tip fingertip regions of gloves 1117 may be of a type that is of generally same circumference as the associated remaining portion of a particular thumb region or finger region. In other instances, one or more of the non-bullet-tip fingertip regions may be of a reduced circumference relative to the associated remaining portion of the respective thumb region or finger region.

It will further be understood that the smooth portion of the fingertip region(s) may be provided on only that part of the fingertip region of glove 1117 that would come into contact with objects if held in a gloved hand. In other examples, substantially the entire circumferential surface of the fingertip region may be smooth. So, for example, only the fingertip region 1108a may be smooth (non-textured) but the skirt 1108d may be textured. Skirt 1108d may be textured even if the remaining portion 1108 is smooth. In other instances, the bullet-tip fingertip region 1108a and the skirt 1108d, for example, may both be smooth while the remaining portion 1108c may be textured, or vice versa. The provision of texturing or non-texturing of various areas of the glove 1117 may be selected based on the end use of glove 1117 and any desired combination of smoothness or texturing with one or more textures may be employed in glove 1117. It will be understood that in other exemplary gloves in accordance with the present disclosure, the gloves 1117 may be substantially identical to the gloves shown in FIGS. 23A-23E except that the bullet-tip fingertip region(s) on glove 1117 may be textured while the rest of the glove may be smooth and vice versa.

In each finger region or thumb region of the gloves illustrated in FIGS. 23A-23E that has a fingertip region that is of a reduced or smaller circumference than the circumference of the associated remaining portion, the associated skirt acts as a step-down region.

Figure 24A:
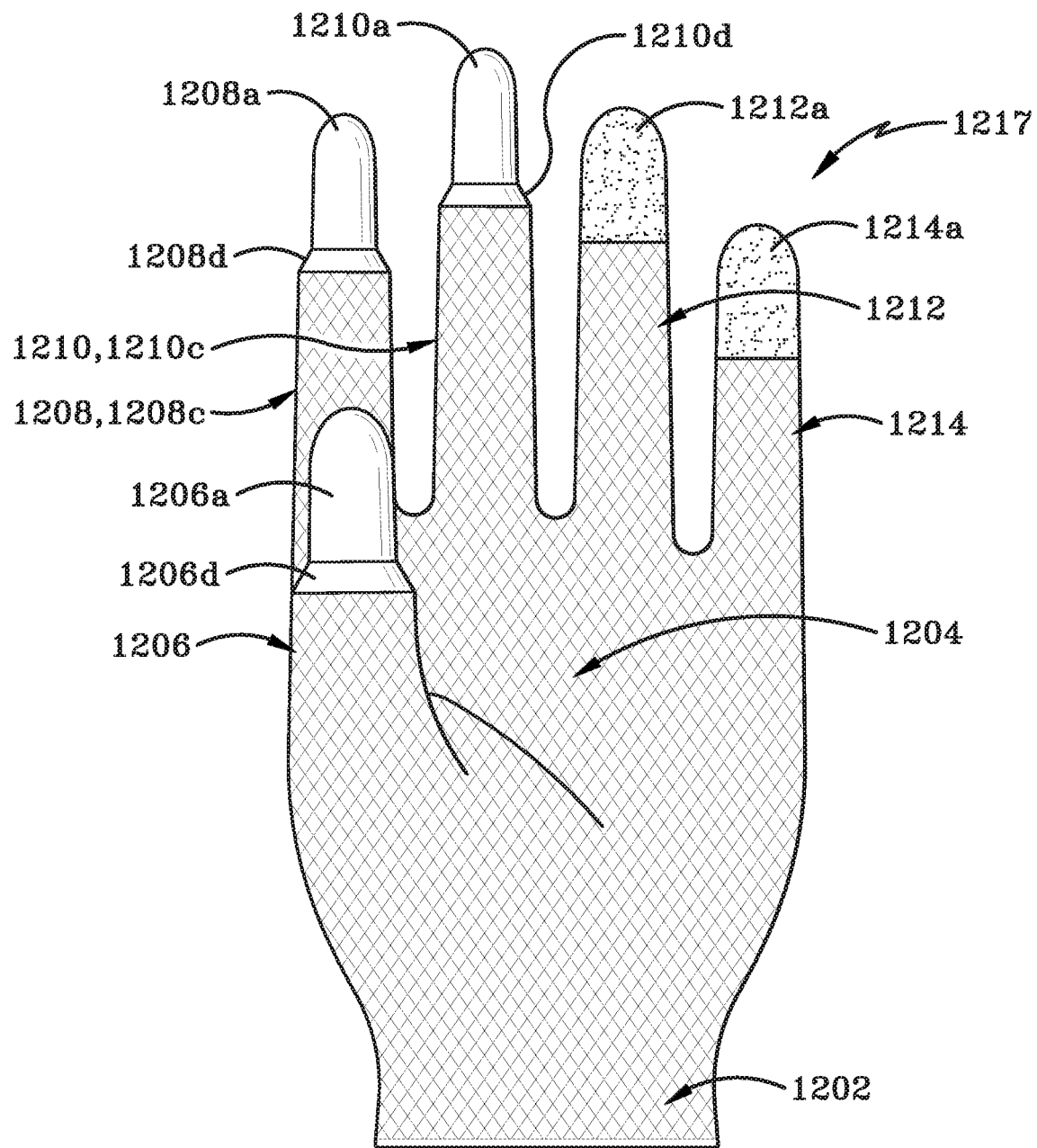
FIG. 24A is a front elevational view of a first example of a fifteenth embodiment where the glove is a hand-specific glove having a bullet-tip type fingertip region provided on the thumb region, index finger region, and middle finger region; a fingertip region of generally a same circumference as the associated remaining portion on the ring finger region and little finger region, and where the bullet-tip fingertip regions are smooth, the same circumference fingertip regions are provided with a first texture and the rest of the gloves is provided with a second texture.
Figure 24B:
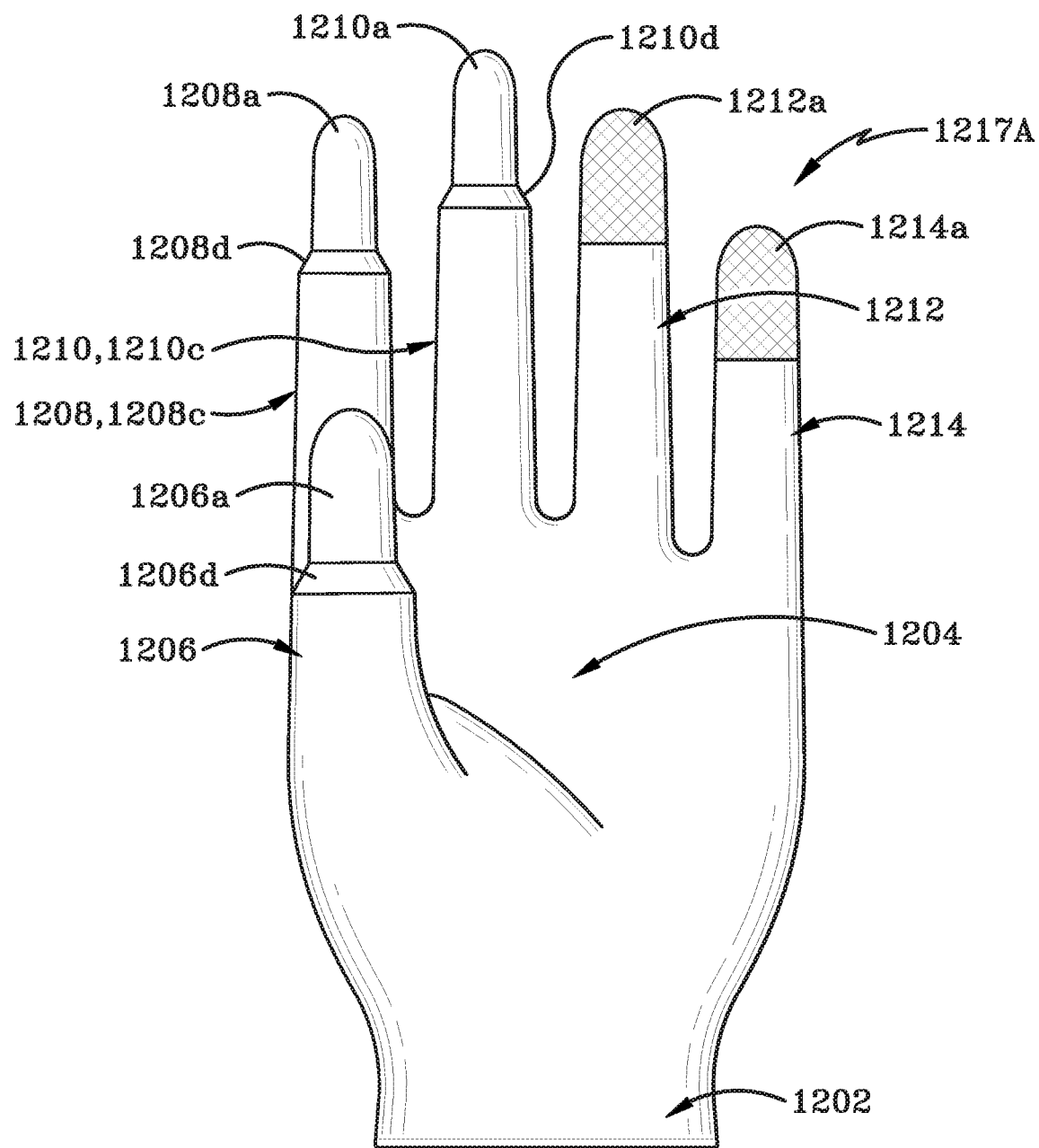
FIG. 24B is a front elevational view of a second example of the fifteenth embodiment where the glove is substantially identical to the glove shown in FIG. 24A except a first texture is provided on the same circumference fingertip regions and the rest of the glove is smooth.
Figure 24C:
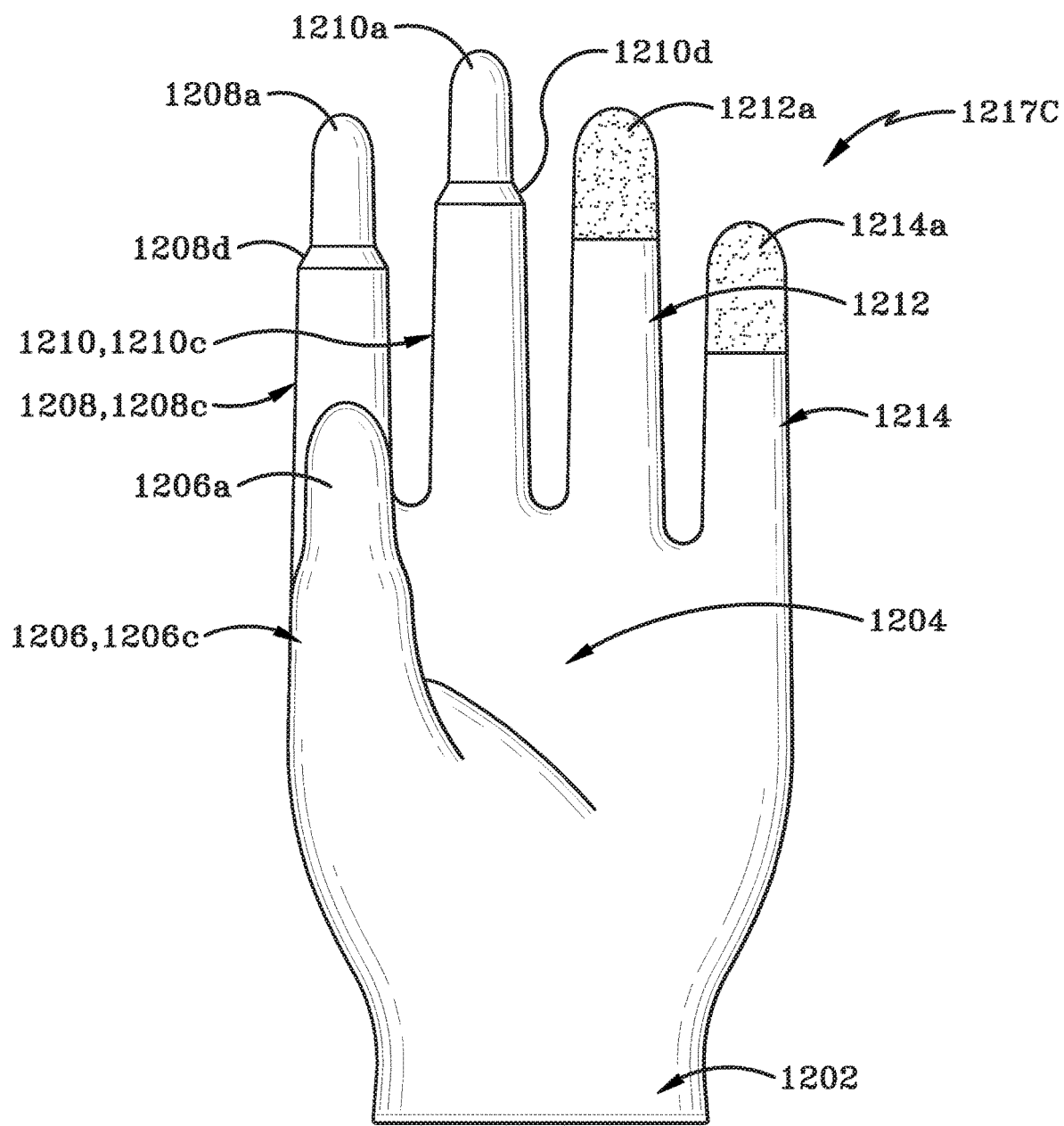
FIG. 24C is a front elevational view of a third example of the fifteenth embodiment where the glove is substantially identical to the glove shown in FIG. 24B except that the fingertip region of the thumb region is not a bullet-tip configuration but is instead of a smaller circumference than the associated remaining portion of the thumb region; and where a different texture is provided on the fingertip regions of the ring finger region and the little finger region.

FIGS. 24A to 24C show examples of a fifteenth embodiment of a glove in accordance with the present invention generally indicated as glove 1217. Glove 1217 may be substantially identical to any of the gloves illustrated in FIGS. 23A-23E except that instead of the entire glove being smooth or non-textured, different areas of the glove may be smooth or textured with a first texture or with a second texture. FIGS. 24A to 24C are provided as examples of different textured and non-textured areas on the glove.

FIG. 24A shows glove 1217 that is substantially identical in configuration to glove 1117B shown in FIG. 23C except that bullet-tip fingertip regions 1206a, 1208a, 1210a and their associated skirts 1206d, 1208d, 1210d are smooth (non-textured), fingertip regions 1212a, 1214a (which are of generally the same circumference as remaining portions 1212c, 1214c) are provided with a first texture. The rest of glove 1217 is provided with a second texture.

FIG. 24B shows another exemplary glove 1217A that is substantially identical to glove 1217 except that bullet-tip fingertip regions 1206a, 1208a, 1210a and the associated skirts 1206d, 1208d, 1210d are all smooth, fingertip regions 1212a, 1214a (which are of generally the same circumference as the associated remaining portions 1212c, 1214c) are provided with a first texture and the rest of the glove 1217A is smooth or non-textured.

FIG. 24C shows another exemplary glove 1217B that is substantially identical to glove 1217A shown in FIG. 24B except that the texture provided on fingertip regions 1212a, 1214a is a sand-type texture instead of a diamond texture. The rest of the glove is smooth or non-textured. The other big difference between glove 1217B and glove 1217A is that the fingertip region 1206a of thumb region 1206 is not a bullet-tip configuration but is instead of a smaller circumference than the associated remaining portion 1206c. Glove 1217B therefore includes one or more fingertip regions that are of the same general circumference as the associated remaining portion of that thumb region or finger region; one or more fingertip regions that are of a smaller circumference than the associated remaining portion of that thumb region or finger region; and one or more fingertip regions that are of a bullet-tip configuration with a skirt connecting the bullet-tip and the associated remaining portion of that thumb region or finger region. The number of location of the different fingertip configurations may be varied depending on the end use of glove 1217. Similarly the texturing or non-texturing of the various fingertip regions and the rest of the glove may be selected based on the end use of the glove 1217.

In each finger region or thumb region of the gloves illustrated in FIGS. 24A-24C that has a fingertip region that is of a reduced or smaller circumference than the circumference of the associated remaining portion, the associated skirt acts as a step-down region.

FIGS. 25A-25E show a sixteenth embodiment of a glove in accordance with the present disclosure, generally indicated at 1317. The gloves shown in FIGS. 25A-25E are substantially identical to the gloves shown in FIGS. 23A-25E except that the gloves in FIGS. 25A-25E are ambidextrous gloves instead of hand-specific gloves. Each of the gloves in FIGS. 25A-25E includes at least one bullet-tip configuration fingertip region. The texturing of the gloves 1317 in FIGS. 25A-25E is also different to the non-textured glove 1117 shown in FIGS. 23A-23E. Gloves 1317 are entirely textured while gloves 1117 are entirely smooth.

Figure 25A:
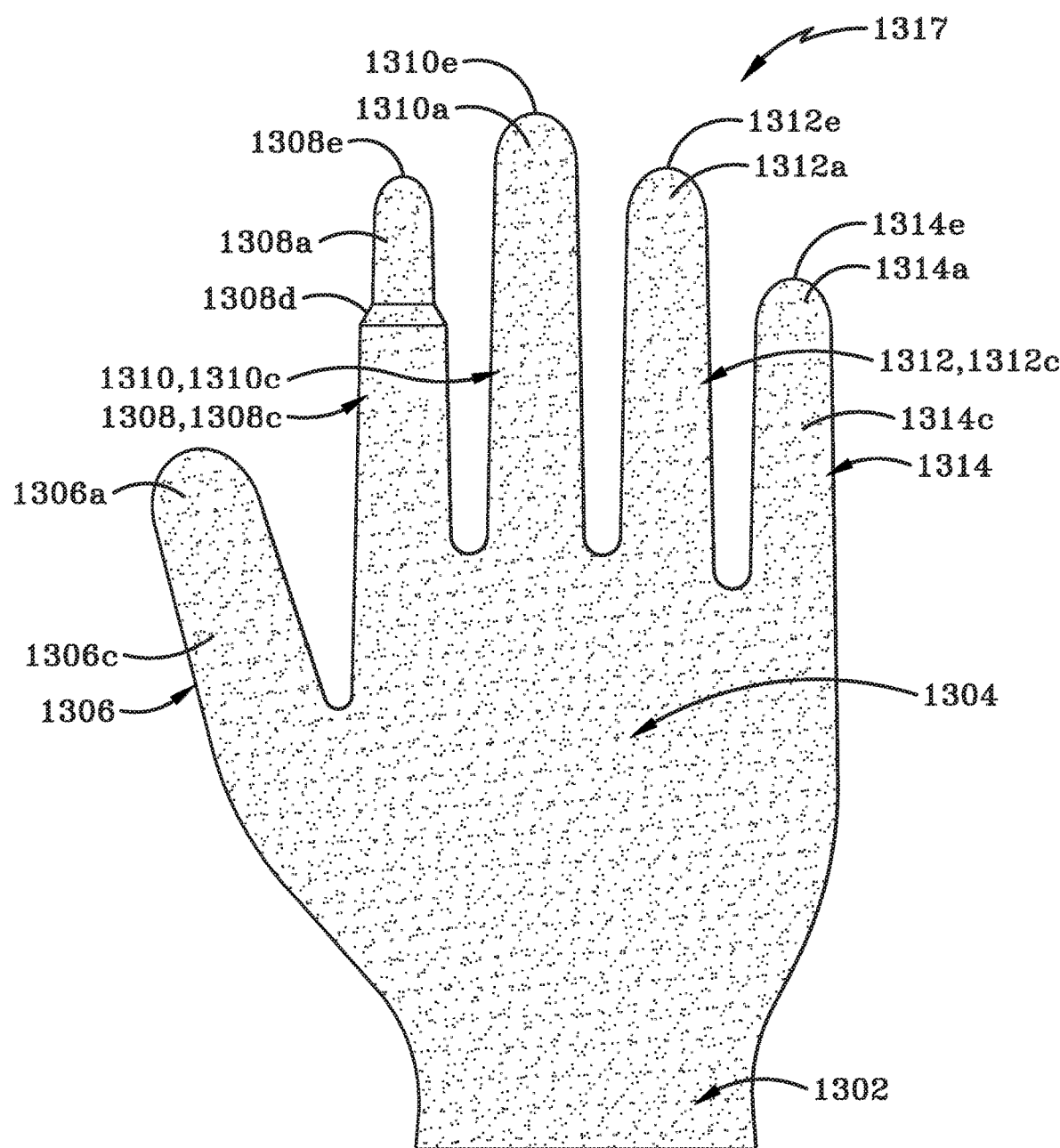
FIG. 25A is a front elevational view of a first example of a seventeenth embodiment of a glove in accordance with an aspect of the present disclosure, where the glove is an ambidextrous glove that has a bullet-tip type fingertip region provided on the index finger region; and showing a skirt extending between the fingertip region and a remaining portion of the index finger region; and where the entire glove is textured.

FIG. 25A shows glove 1317 having a bullet-tip fingertip region 1308a on index finger region 1308 and a skirt 1308d extending between fingertip region 1308a and remaining portion 1308c on index finger region 1308. Fingertip region 1306a, 1310a, 1312a, 1314 are of substantially a same circumference as the associated remaining portions 1306c, 1310a, 1312c, 1314c The entire glove 1317 is textured.

Figure 25B:
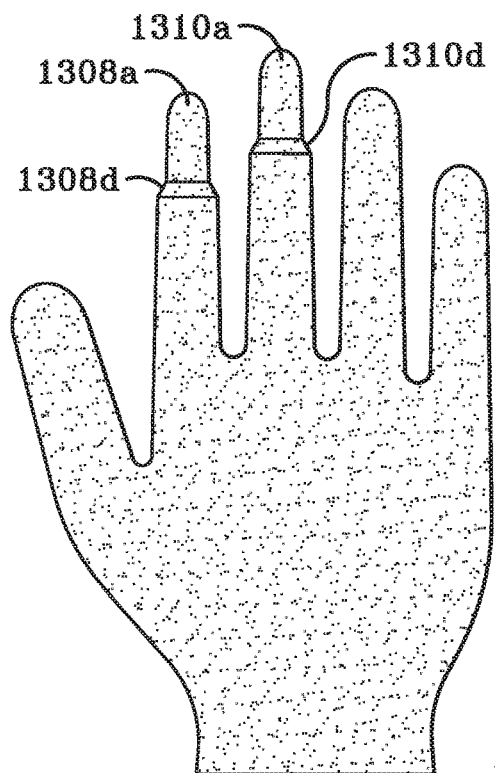
FIG. 25B is a front elevational view of a second example of the seventeenth embodiment where the glove is an ambidextrous glove having a bullet-tip type fingertip region provided on the index finger region and middle finger region, and having a skirt between the bullet-tip and remaining portion thereof, and where the entire glove is textured.

FIG. 25B shows glove 1317A having a bullet-tip fingertip region 1308a, 1310a on index finger region 1308 and on middle finger region 1310. Skirts 1306d, 1310d extend between fingertip regions 1308a, 1310a, and remaining portions 1308c, 1310c on index finger region 1308 and middle finger region 1310. Fingertip regions 1306a, 1312a, 1314a are of substantially a same circumference as remaining portions 1306c, 1312c, and 1314c. The entire glove 1317A may be textured.

Figure 25C:
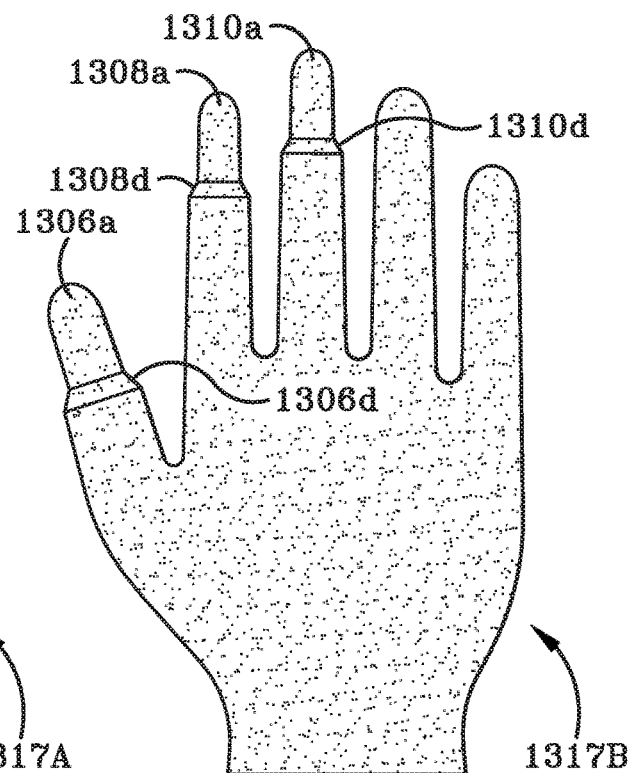
FIG. 25C is a front elevational view of a third example of the seventeenth embodiment where the glove is an ambidextrous glove having a bullet-tip type fingertip region provided on the thumb region, index finger region, and middle finger region, and having a skirt between the bullet-tip and remaining portion thereof, and where the entire glove is textured.

FIG. 25C shows glove 1317B having bullet-tip fingertip regions 1306a, 1308a, 1310a on thumb region 1306, index finger region 1308, and middle finger region 1310. Skirts 1306d, 1308d, 1310d extend between fingertip regions 1306a, 1308a, 1310a and remaining portions 1306, 1308c, 1310c on thumb region 1306, index finger region 1308 and middle finger region 1310. Fingertip regions 1312a, 1314a are of substantially a same circumference as remaining portions 1312c, 1314c. The entire glove 1317A may be textured.

Figure 25D:
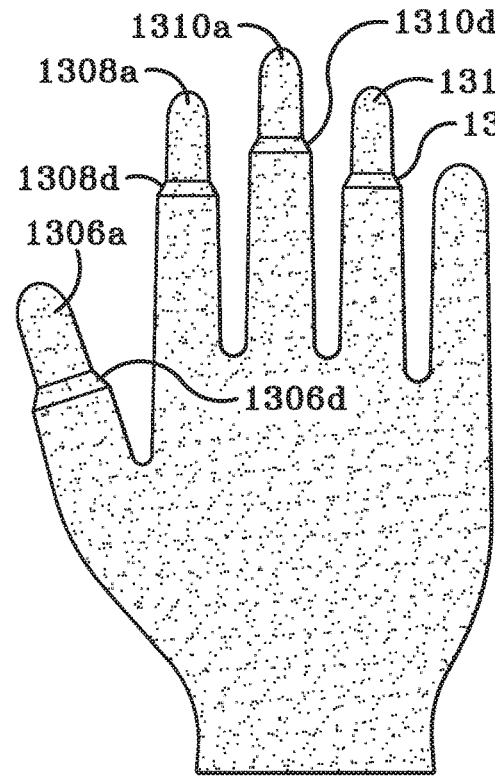
FIG. 25D is a front elevational view of a fourth example of the seventeenth embodiment where the glove is an ambidextrous glove having a bullet-tip type fingertip region provided on the thumb region, index finger region, middle finger region, and ring finger region, and having a skirt between the bullet-tip and remaining portion thereof, and where the entire glove is textured.

FIG. 25D shows glove 1317C having bullet-tip fingertip regions 1306a, 1308a, 1310a, 1312a. Skirts 1306d, 1308d, 1310d, 1312d extend between fingertip regions 1306a, 1308a, 1310a, 1312a and remaining portions 1306, 1308c, 1310c, 1312d on thumb region 1306, index finger region 1308, middle finger region 1310, and ring finger region 1312. Fingertip region 1314a may be of substantially a same circumference as remaining portion 1314c. The entire glove 1317A may be textured. It will be understood that in other examples, a bullet-tip fingertip region 1314a may be provided on little finger region 1314 instead of a bullet-tip fingertip region 1312a being provided on ring finger region 1312. In these instances a skirt 1314d will extend between fingertip region 1314a and remaining portion 1314c. The fingertip region 1312a in these exemplary gloves may be of generally a same circumference as the remaining portion 1312c of ring finger region 1312.

Figure 25E:
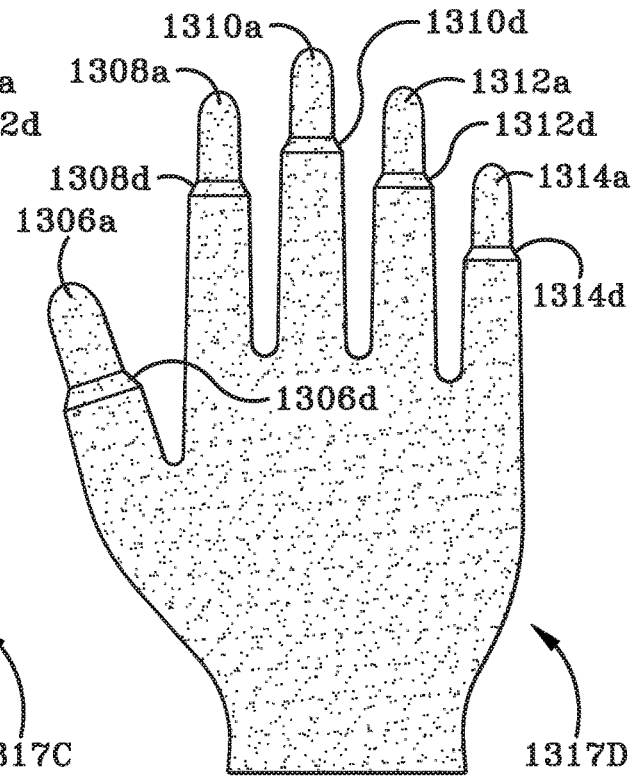
FIG. 25E is a front elevational view of a fifth example of the seventeenth embodiment where the glove is an ambidextrous glove having a bullet-tip type fingertip region provided on all five of the thumb region, index finger region, middle finger region, ring finger region, and little finger region, and having a skirt between the bullet-tip and remaining portion thereof, and where the entire glove is textured.

FIG. 25E shows glove 1317D having bullet-tip fingertip regions 1306a, 1308a, 1310a, 1312a, 1314a on all five of the thumb region 1306, index finger region 1308, middle finger region 1310, ring finger region 1312, and little finger region 1314. The entire glove 1317D may be textured.

It will be understood that one or more of the fingertip regions of any of thumb region 1306, index finger region 1308, middle finger region 1310, ring finger region 1312 or little finger region 1314 that is not formed as bullet-tip fingertip region may, instead, be formed as a fingertip region that is of a smaller circumference than the remaining portion thereof (in a similar fashion to fingertip region 708a of glove 717). Alternatively, one or more of the fingertip regions of any of thumb region 1306, index finger region 1308, middle finger region 1310, ring finger region 1312 or little finger region 1314 that are not formed as bullet-tip fingertip regions may, instead, be formed as a fingertip region that is of generally a same circumference as the associated remaining portion (such as fingertip region 712a of glove 717). A combination of all three different fingertip regions may be provided on a single glove and the placement of each of the three different fingertip types may be selected according to the end use of the glove.

It will further be understood that in any of the gloves disclosed in this document the non-texturing or texturing may be provided on that part of the glove's surface that would come into contact with an object if that object was held in a gloved hand. In other gloves in accordance with the present disclosure substantially the entire circumferential surface of the glove may be textured or non-textured. The entire glove may also be provided with a texture, with one or more textures, or be non-textured.

In each finger region or thumb region of the gloves illustrated in FIGS. 25A-25E that has a fingertip region that is of a reduced or smaller circumference than the circumference of the associated remaining portion, the associated skirt acts as a step-down region.

Figure 26:
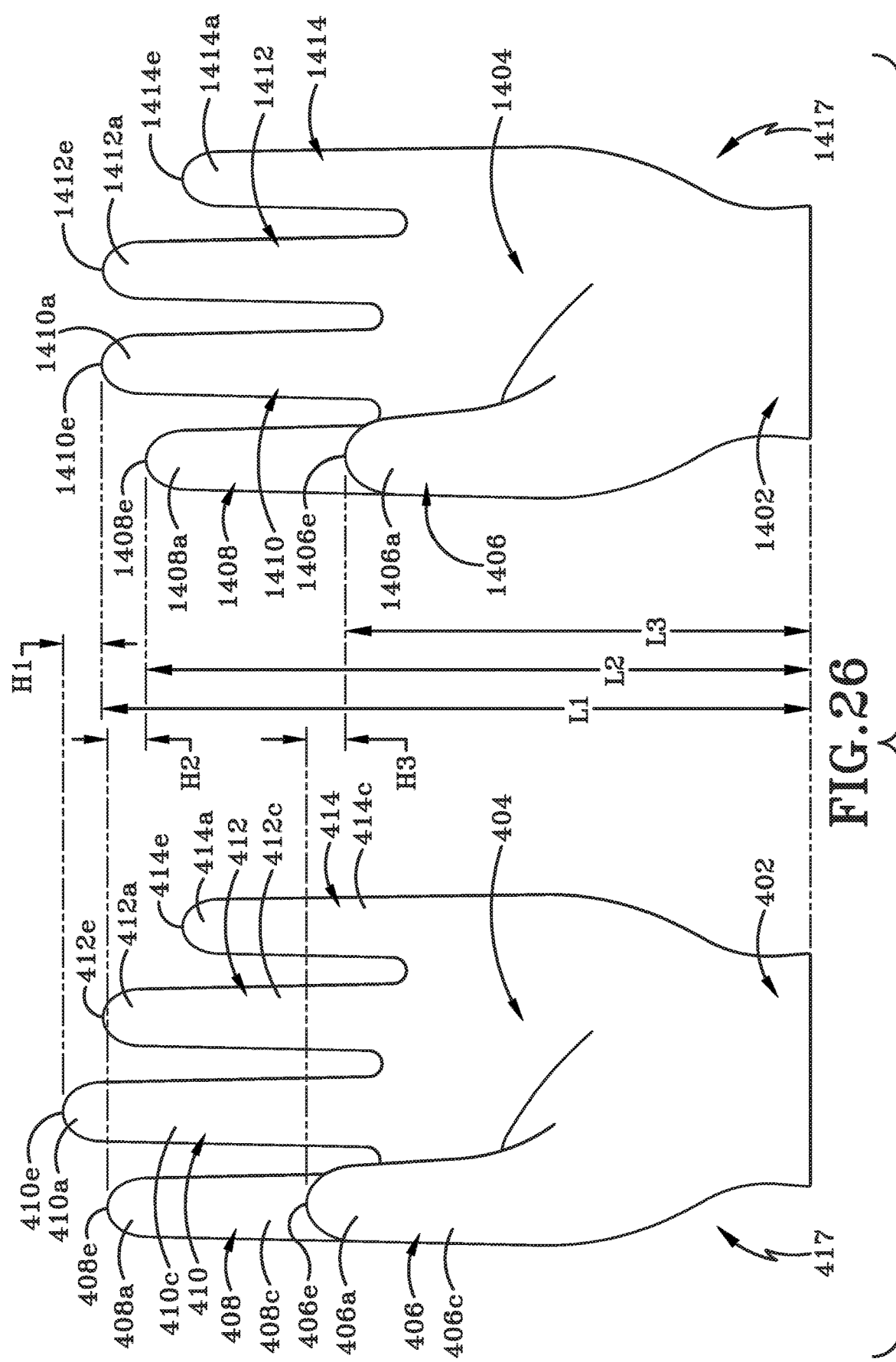
FIG. 26 is a front elevation view of two gloves placed side-by-side, where one of the gloves is the glove shown in FIG. 16A (without texturing) and the other glove is an eighteenth embodiment of a glove in accordance with the present disclosure, where both the index finger region and middle finger region have been reduced in length relative to the glove shown in FIG. 16A.

FIG. 26 shows two gloves placed side-by-side, where one of the gloves is an example of an eighteenth embodiment of a glove in accordance with the present disclosure.

FIG. 26 shows a first glove that is substantially identical to the glove 417 shown in FIG. 16B with the exception that no texturing is shown on the glove. Glove 417, as previously described herein, is a hand-specific glove that includes a wrist region 402, palm region 404, thumb region 406, index finger region 408, middle finger region 410, ring finger region 412, and little finger region 414. Glove 417 also has fingertip regions 406a, 408a, 410a, 412a, 414a that are generally of the same circumference as the remaining portions 406c, 408c, 410c, 412c, and 414c of the respective thumb region 406, index finger region 408, middle finger region 410, ring finger region 412, or little finger region 414. Each fingertip region includes an end 406e, 408e, 410e, 412e, or 414e that is located a distance remote from palm region 404. The overall length of each of the thumb region and the finger regions is measured from the respective end to the palm region.

FIG. 26 also shows a first example of the eighteenth embodiment of a glove in accordance with the present disclosure, generally indicated at 1417. Glove 1417 is a hand-specific glove that includes a wrist region 1402, palm region 1404, thumb region 1406, index finger region 1408, middle finger region 1410, ring finger region 1412, and little finger region 1414. Glove 1417 also has fingertip regions 1406a, 1408a, 1410a, 1412a, 1414a that are generally of the same circumference as the remaining portions 1406c, 1408c, 1410c, 1412c, and 1414a of the respective thumb region 1406, index finger region 1408, middle finger region 1410, ring finger region 1412, or little finger region 1414. Glove 1417 is also shown free of texture.

Middle finger region 1410 of glove 1417 has an end 1410e that is located a distance remote from palm region 1404. The length "L1" of middle finger region 1410 is approximately the same as the length "L1" of ring finger region 1412. The length "L1" is measured from the respective end 1410e, 1412e to a bottom 1402a of wrist region 1402. By contrast, the end 410e of middle finger region 410 of glove 417 that is positioned a distance "H1" outwardly beyond an end 412e of ring finger region 412. So the overall length of middle finger region 410 of glove 417 measured from end 410e to palm region 404 is the equivalent of "L1"+"H1". In other words, the overall length of middle finger region 410 on glove 417 is longer than the overall length of the middle finger region 1410 on glove 1417. It should also be noted that on glove 417, middle finger region 410 extends outwardly for a distance beyond the end 412e of ring finger region 412.

In glove 1417, on the other hand, middle finger region 1410 has effectively been reduced in overall length relative to middle finger region 410 of glove 417. In particular, middle finger region 1410 on glove 1417 is of approximately the same length as ring finger region 1412. In other words, end 1410e of middle finger region 1410 is generally aligned with an end 1412e of ring finger region 1412. The relative reduction in overall length of middle finger region 1410 helps to ensure that the glove material of middle finger region 1410 is thinned and pulled firmly and tightly around the fingertip of the user's middle finger.

A further comparison of glove 417 and glove 1417 shows that the overall length "L2" of index finger region 1408 on glove 1417 has also been reduced relative to the overall length of index finger region 408 of glove 417. Index finger region 408 extends outwardly beyond end 1408e of index finger region 1408 by a distance "H2". Thus the overall length of index finger region 408 from end 408e to palm region 404 is "L2"+"H2". (The index finger region 408 is longer than index finger region 1408 by the distance "H2") Again, the relative reduction in overall length of index finger region 1408 to "L2" causes the material of index finger region 1408 to be thinned and pulled firmly and tightly around the fingertip of the user's middle finger when the glove is worn.

A further comparison of glove 417 and glove 1417 shows that the overall length "L3" of thumb region 1406 is also reduced relative to the overall length of thumb region 406 of glove 417. Thumb region 406 extends outwardly beyond end 1408e of thumb region 1406 by a distance "H3". Thus the overall length of thumb region 408 from end 408e to palm region 404 is "L3"+"H3". (Thumb region 408 is longer than thumb region 1408 by the distance "H3".) Again, the relative reduction in overall length of thumb region 1406 causes the material of thumb region 1406 to be thinned and pulled tightly around the fingertip of the user's thumb. Thumb region 406 extends for a distance "H3" outwardly beyond an end 1406e of thumb region 1406.

The distances "H1" and "H2" and "H3" may be from about 2 mm up to about 5 mm.

It will be understood that the entire glove 1417 may be textured or non-textured. In other instances, one or more of the fingertip regions 1406a, 1408a, 1410a, 1412a, 1414a may be textured while the rest of glove 1417 is non-textured or vice version. In other examples, one or more of the fingertip regions 1406a, 1408a, 1410a, 1412a, 1414a may fabricated to be of a smaller circumference than a remaining portion 1406c, 1408c, 1410c, 1412c, or 1414c. In other examples, one or more of the fingertip regions 1406a, 1408a, 1410a, 1412a, 1414a may be fabricated as bullet-tip fingertip regions and may include associated skirts.

It will further be understood that while glove 1417 is illustrated as a hand-specific glove, glove 1417 may, instead be an ambidextrous glove. In this instance, all of the features of the ambidextrous glove are substantially identical to glove 1417 except that thumb region 1406 will be oriented in the same plane as the index finger region 1408, middle finger region 1410, ring finger region 1412 and little finger region 1414.

It will further be understood that instead of all of the thumb region 1406, index finger region 1408, and the middle finger region 1410 being reduced in overall length, a glove may be fabricated that has only a reduced length thumb region 1406, or a reduced length index finger region 1408, or a reduced length middle finger region 1410, while the rest of the glove is substantially identical to glove 417 (except for the texturing thereon). Alternatively, instead of only one of the thumb region 1406, index finger region 1408 and the middle finger region 1410 being reduced in overall length, a glove may be fabricated that has two out of the three of the thumb region 1406, index finger region 1408, or middle finger region 1410 reduced in length relative to glove 417. The other features of glove 1417 are substantially identical to glove 417 (except possibly for the presence of texturing thereon).

In some examples, there may be about a 4 mm reduction in the length of thumb region 1406, a 5 mm reduction in the length of index finger region 1408, and a 6 mm reduction in the length middle finger region. The transition or step-down between the circumference of the remaining portion and the associated reduced circumference diameter may be in the order of from about 35° up to about 65° relative to the circumference of the remaining portion, with from about 45° up to about 60° being a preferred angle of transition. The reduction in the diameter of the fingertip regions may be in the order of from about 1% up to about 15% smaller, with the preferred range being a diameter reduction in the order of from about 3% up to about 7%. The provision of the step-down or angled transition region is helpful when the user is performing tasks such as turning a wheel on an intra-venous bag or when grasping an object while wearing the glove. It should be noted that the above-mentioned measurements are relative to an industry standard glove.

Figure 27A:
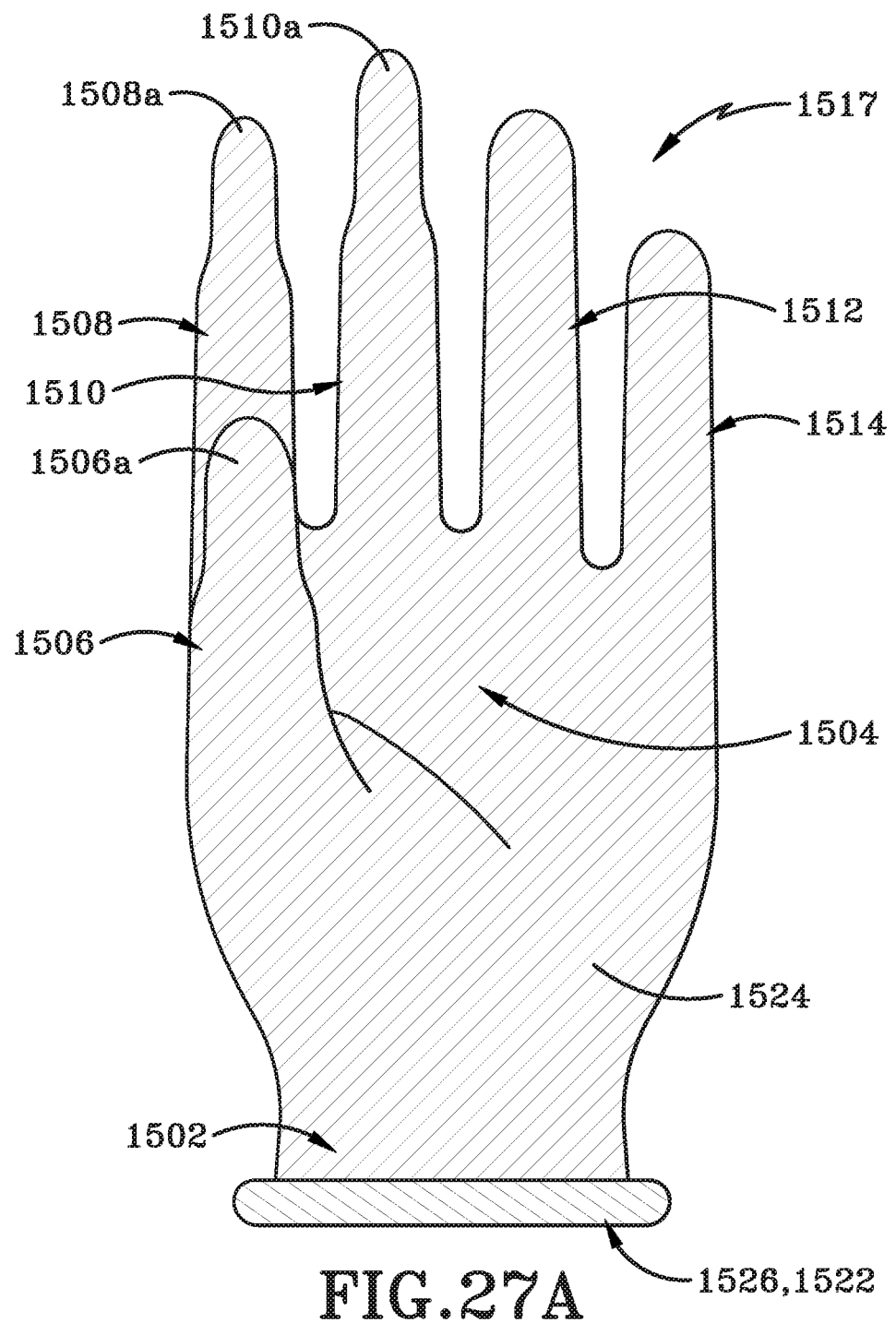
FIG. 27A is a front elevational view of a nineteenth embodiment of a glove in accordance with the present disclosure, where the glove is a hand-specific glove that includes a tear indicator in the form of a differently colored interior and exterior surface or layer; and wherein the presence of the tear indicator is visible to an observer in the form of a rolled cuff that is of a color that is different to a color of the rest of the glove.

FIG. 27A shows a nineteenth embodiment of a glove in accordance with the present disclosure, generally indicated at 1517. Glove 1517 is identical to the glove 617 shown in FIG. 18C in all features except for a few features that will be described hereafter. Glove 1517 includes a wrist region 1502, a palm region 1504, a thumb region 1506, an index finger region 1508, a middle finger region 1510, a ring finger region 1512, and a little finger region 1514. Glove 1517 includes reduced circumference fingertip regions 1506*a*, 1508*a*, and 1510*a* on the thumb region 1506, index finger region 1508, and middle finger region 1510. Glove 1517 is different from glove 617 in that it is fabricated from a material that may be comprised of a single layer that has an interior surface and an exterior surface or may be comprised of an interior layer 1522 and an exterior layer 1524 where the exterior surface or exterior layer 1524 may be of a first color and the interior surface or interior layer 1522 may be of a second color that contrasts with first color. Glove 1517 also includes a rolled cuff region 1526. Cuff region 1526 may be an extended length of wrist region 1502 that is rolled back upon itself to form the rolled cuff region 1526. The rolling of this extended length of the wrist region causes the color of the interior surface or interior layer 1522 to become visible. The exterior of the glove 1517 is of the first color and the rolled cuff 1526 forms a rim of the second color at the bottom end of the wrist region 1502. The contrast between the first and second colors tends to draw an observer's eye to the second color of the rolled cuff 1526. Furthermore, if the glove is cut, ripped, or torn, the second color of the interior surface or interior layer 1522 may become visible to the person wearing the glove or to other people who see the glove wearer's hands. The contrasting first and second colors therefore act as a cut indicator or tear indicator. The contrasting colored rolled cuff 1526 may be utilized to indicate to the wearer or others that the glove 1517 includes a tear indicator. It will be understood that the rolled cuff does not need to be the same color as the interior surface or interior layer of the glove but may be a completely different color therefrom and also may be a completely different color from the exterior surface or exterior layer (i.e., a third color).

Figure 27B:
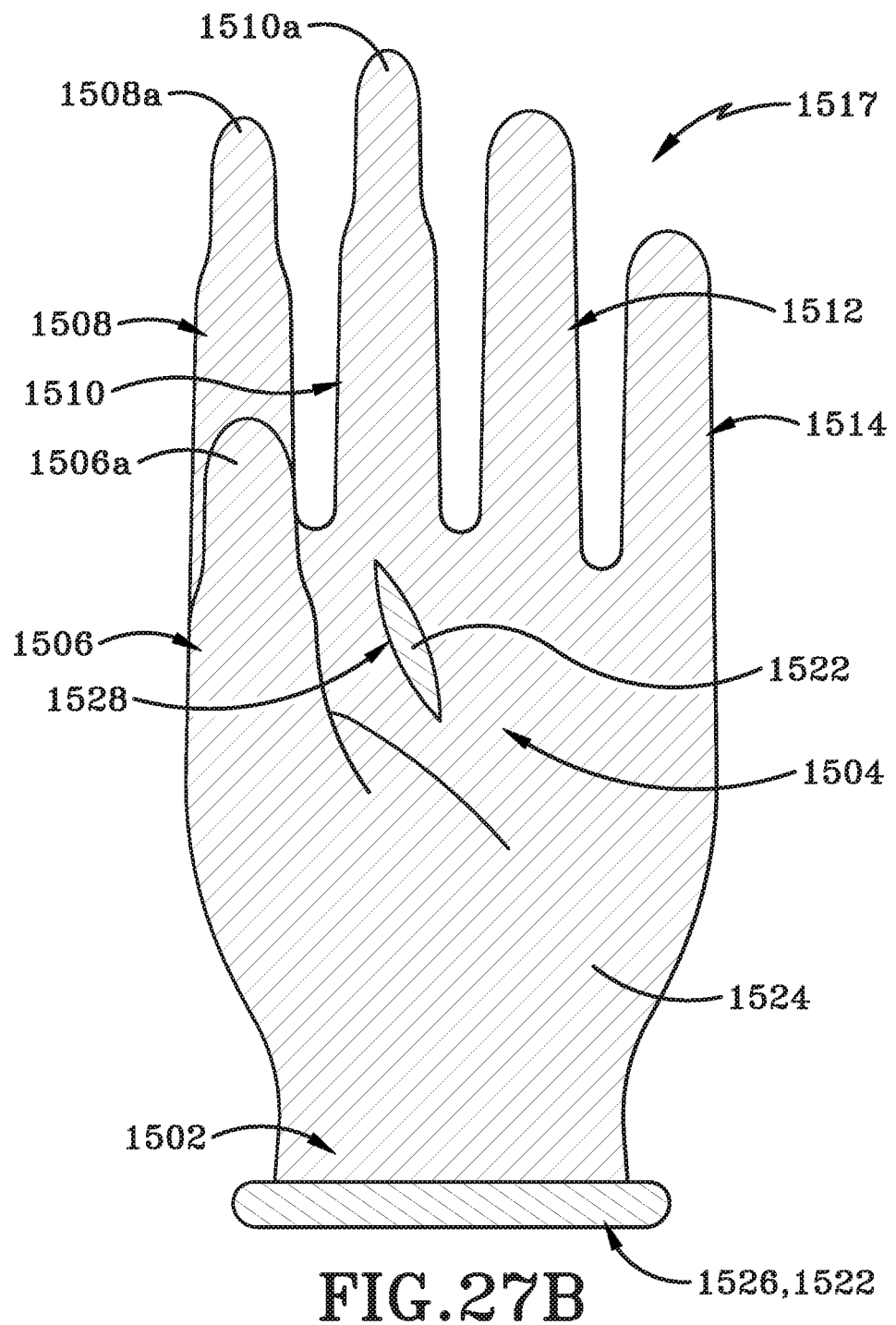
FIG. 27B is a front elevational view of the glove of FIG. 27A where the glove includes a cut and the differently colored interior surface or layer is visible through the cut.

FIG. 27B shows glove 1517 that is identical to the glove shown in FIG. 27A except that a portion of the glove has been torn or cut at 1528. As a consequence, the second color of the interior surface or interior layer 1522 is visible through cut 1528 and stands out relative to the first color of the exterior surface or exterior layer 1524. It is therefore very easy for a person wearing glove 1517 to see the cut 1528 and realize that the glove 1517 has been compromised and must be changed. It is also very easy for an observer to see the cut 1528 on the glove 1517 worn on another's hand because the second color of the interior surface or interior layer 1522 draws the observer's eye to the location of the cut 1528 on the first colored exterior surface 1524. The observer can then bring the cut 1528 to the glove wearer's attention.

It will be understood that this tear indicator (i.e., the presence of the two differently colored surface or layers) plus the rolled cuff 1526 can be utilized on any of the gloves disclosed herein.

It will further be understood that the tear indicator may also be useful if the glove material is simply wearing thin from use or is deteriorating. The differently colored interior surface or layer may progressively become visible through the thinning or deteriorating exterior surface or layer, thereby warning the user that the glove is nearing the end of its useful life.

Figure 28:
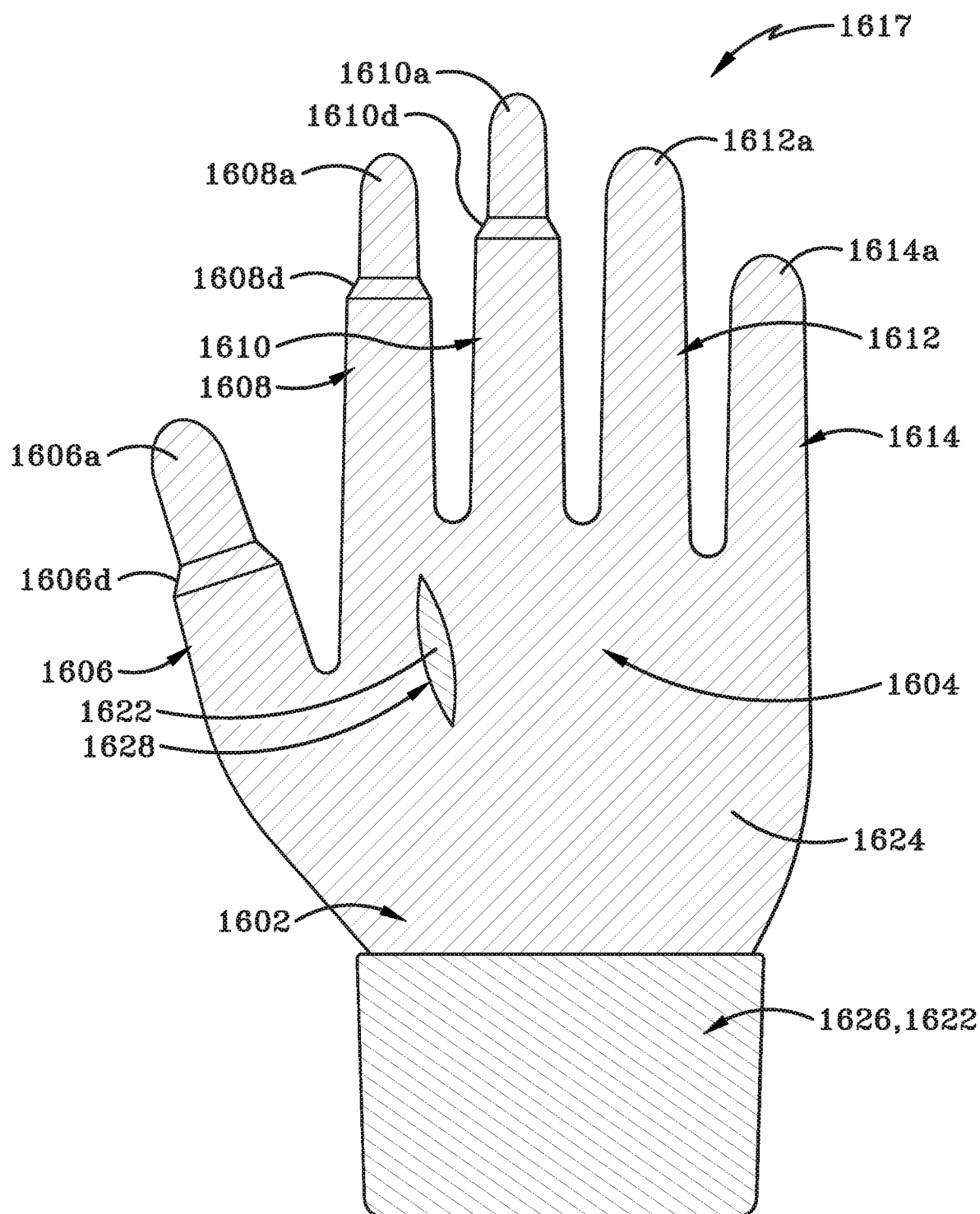
FIG. 28 is a front elevational view of a twentieth embodiment of a glove in accordance with the present disclosure, where the glove is an ambidextrous glove that incorporates the features of the tear indicator of FIGS. 27A, and 27B therein and which includes a folded cuff instead of a rolled cuff.

FIG. 28 is a twentieth embodiment of a glove in accordance with the present disclosure, generally indicated at 1617. Glove 1617 is an ambidextrous glove that incorporates the features of the tear indicator into the same. FIG. 28 shows glove 1617 that includes a wrist region 1602, a palm region 1604, thumb region 1606, index finger region 1608, middle finger region 1610, ring finger region 1612, and little finger region 1614. By way of a non-limiting example only, glove 1617 further includes one or more bullet-tip fingertip regions 1606*a*, 1608*a*, and 1610*a* with skirts 1606*d*, 1608*d*, 1610*d* on thumb region 1606, index finger region 1608, and middle finger region 1610. Glove 1617 also includes one or more fingertip regions 1612*a*, 1614*a* that are generally of the same circumference as the associated remaining portions 1612*c*, 1614*c*. Although not shown in FIG. 28, it will be understood that glove 1617 may, alternatively or additionally, include one or more fingertip regions that are of a smaller diameter than the associated remaining portion. It will be further understood that any one or more of these three different types of fingertip regions may be utilized in glove 1617. Glove 1617 may also include any desired combination of smooth areas or areas that are textured with a first texture or a second texture.

Glove 1617 may further include an additional feature that may also be included in any of the other gloves described herein, namely the provision of a rip, cut or tear-indicator 1620 that is substantially identical in nature and function to the tear indicator on glove 1417. In particular, any of the gloves in accordance with the present disclosure may be fabricated to include an exterior surface or exterior layer 1624 of a first color an interior surface or interior layer 1622 of a second color. The first color and second color are preferably sufficiently contrasting that if a rip, cut or tear 1628 forms in the exterior surface or exterior layer 1624, the second color of the interior surface or interior layer 1622 will become evident and visible to the wearer of glove 1617 or to others that observe the wearer's hand. When such a tear indicator 1628 becomes evident, the wearer will be made aware that glove 1617 has been compromised and will remove and discard at least the cut or torn glove 1617.

If the glove that includes the tear indicator is a hand-specific glove such as glove 1417, then both the left hand glove and right hand glove will likely have to be pulled off the user's hands and be thrown away. If the glove is an ambidextrous glove such as glove 1617, then only the damaged glove will likely have to be removed and thrown away.

A folded cuff 1626 may be provided as part of wrist region 1602 of glove 1617. The cuff comprises a length of wrist region 1602 that has been folded up to form the end of the glove 1617. The cuff 1626 is folded in such a way that second color of the interior surface or interior layer 1622 forms a stripe of second color around the circumference of the lower end of the wrist region 1602. The second color stripe is readily observed because the second color contrasts with the first color on the rest of wrist region 1602 and glove 1617. The folded cuff 1626 therefore indicates to a person that this particular glove includes a tear indicator.

In other instances, the contrasting color cuff 1626 (whether rolled, folded or otherwise formed) may further be utilized to identify to users the particular types of material from which the glove 1617 may be fabricated. For example, the interior surface or interior layer 1622 may be formed from a material that is free of or is essentially free of elements, components, or compounds that may cause hypersensitivity and/r allergic reaction in people who wear the glove 1617. A particular color may be utilized in either or both of the interior surface or interior layer 1622 and exterior surface or exterior layer 1624 to identify the particular properties or materials utilized in that layer or surface. In other instances, the interior surface or interior layer 1622 or exterior surface or exterior layer 1624 may be fabricated from a material that shields the user from exposure to certain dangerous substances. For example, the interior and exterior layers or surfaces 1622, 1624 may protect the wearer from being exposed to substances such as fentanyl. Again, a particular color provided in either of the interior surface or layer 1622 or exterior surface or layer 1624 of glove 1617 may be used to signify this property.

FIGS. 29A-29G disclose features of a twenty-first embodiment of a glove in accordance with the present disclosure, generally indicated at 1717. Glove 1717, as illustrated is a hand specific glove but it should be understood that similar features as will be described hereafter may be readily incorporated into an ambidextrous glove. Glove 1717 includes a wrist region 1702, a palm region 1704, a thumb region 1706, an index finger region 1708, a middle finger region 1710, a ring finger region 1712, and a little finger region 1714.

Glove 1717 is shown as including includes a fingertip region 1706a on the thumb region 1706 that is of a bullet-tip configuration where the bullet-tip type fingertip region 1706 is connected via a skirt 1706d to a remaining portion. The fingertip region 1708a of index finger region 1708 is not of a bullet-tip configuration but is of a reduced circumference compared to the remaining portion thereof. The fingertip region 1710a of middle finger region 1710 is, again of a bullet-tip configuration and is connected to a remaining portion of middle finger region 1710 by skirt 1710d.

In accordance with a feature of the present disclosure, a fluted region 1730 (FIGS. 29B and 29C) is provided on fingertip region 1708a. Fluted region 1730 may be particularly useful since the configuration narrows the fingertip region 1708a and therefore helps fingertip region 1708a to more effectively grip the user's fingertip that is received therein. Fluted region 1730 also breaks the suction between fingertip region 1708a and the user's fingertip while the glove 1717 is being donned (put on) or doffed (taken off). Fluted region 1730 may be oriented generally parallel to a longitudinal axis "Y" of index finger region 1708. Fluted region 1730 may be located entirely within fingertip region 1708a, or partially in fingertip region 1708a and partially in the remaining portion of index finger region 1708. The fluted region 1730 extends for a distance into the associated interior cavity 1708b (FIG. 29C). Fluted region 1730 may be formed anywhere on the circumference of fingertip region 1708a but one particularly suitable location is generally along a midline of a side surface of the fingertip region 1708a that is adjacent thumb region 1706. Fluted region 1730 effectively aids in reducing the circumference of fingertip region 1708a.

It should be noted that fingertip region 1708a may be narrowed front surface to back surface only and not around substantially the entire circumference of fingertip region 1708a.

Figure 29A:
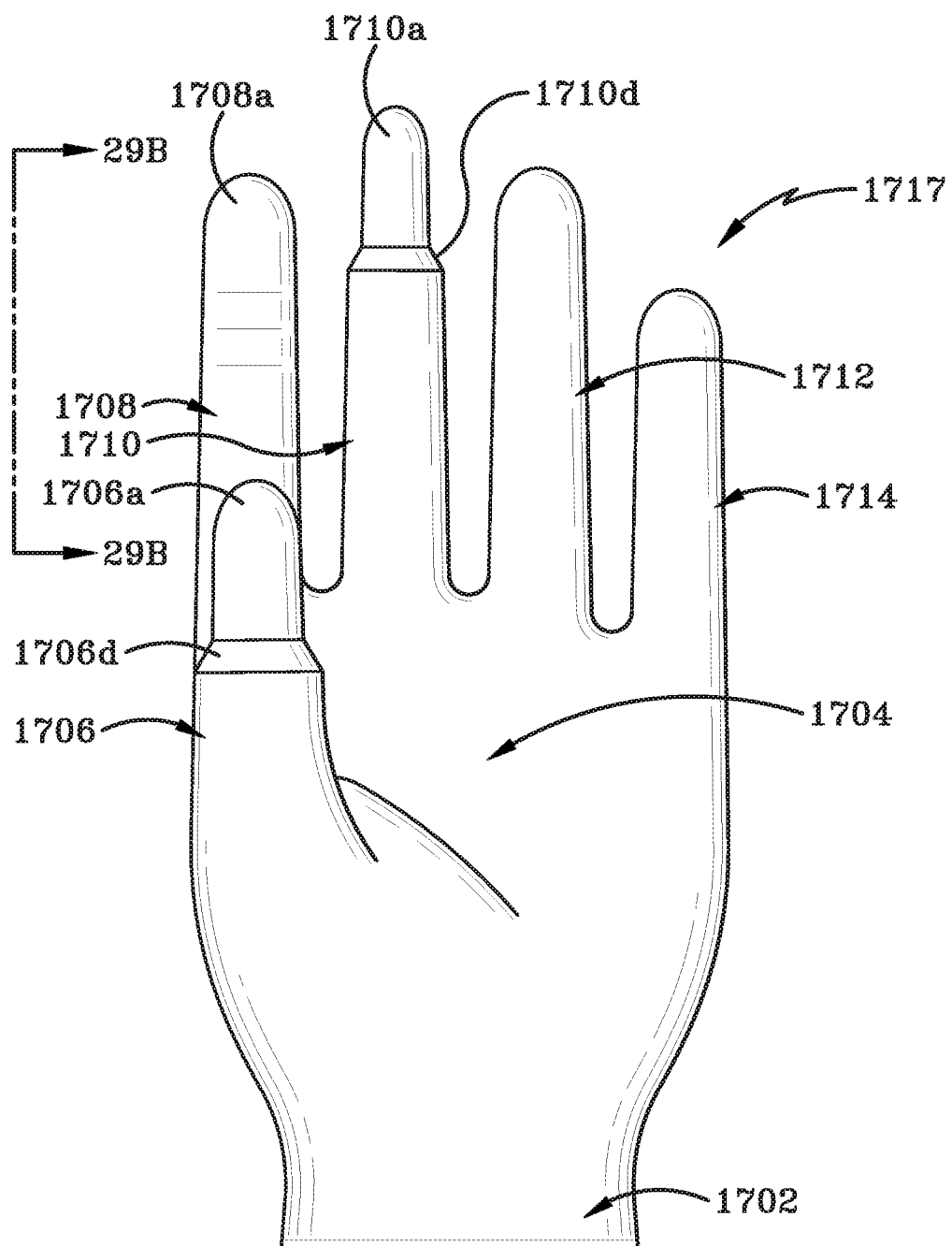
FIG. 29A is a front elevational view of a twenty-first embodiment of a glove in accordance with the present disclosure, where the glove is a hand-specific glove having at least one fingertip region that includes a fluted region therein.
Figure 29D:
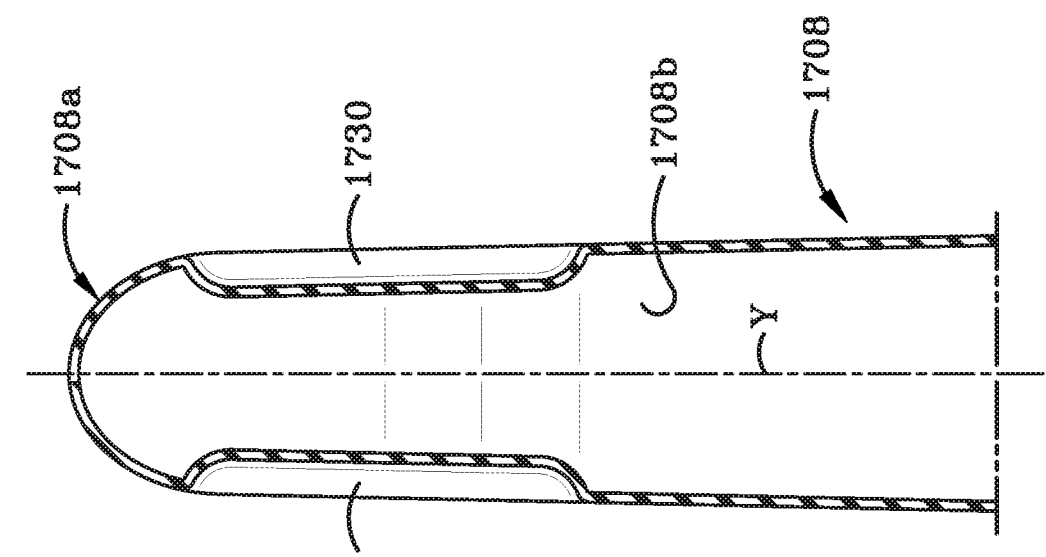
FIG. 29D is a longitudinal cross-section of an alternative version of the fingertip region that includes two opposed fluted regions.
Figure 29C:
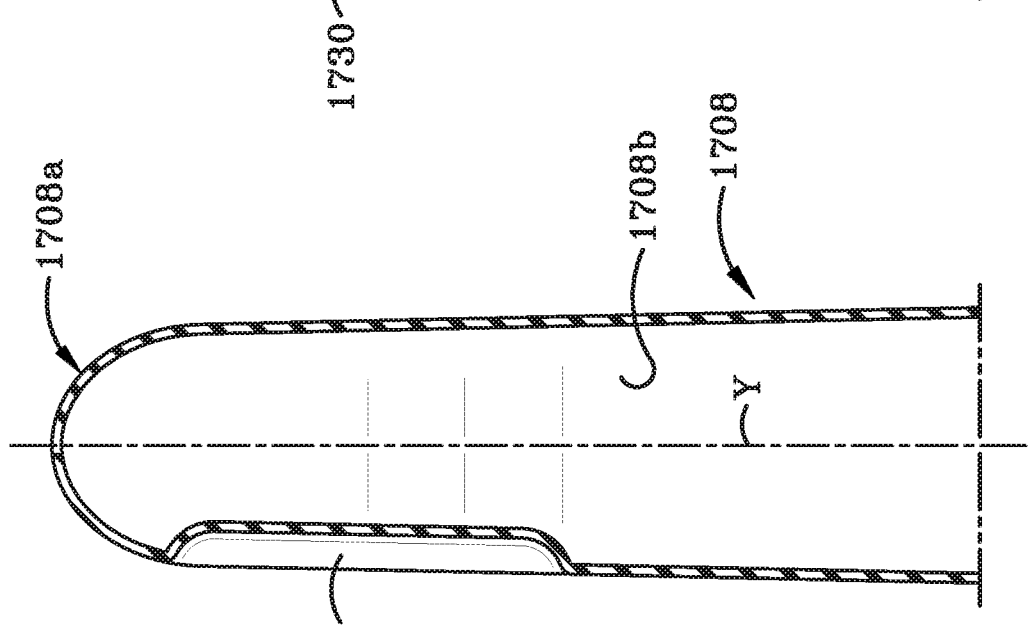
FIG. 29C is a longitudinal cross-section of the fingertip region having the fluted region taken along line 29C-20C of FIG. 29B.
Figure 29B:
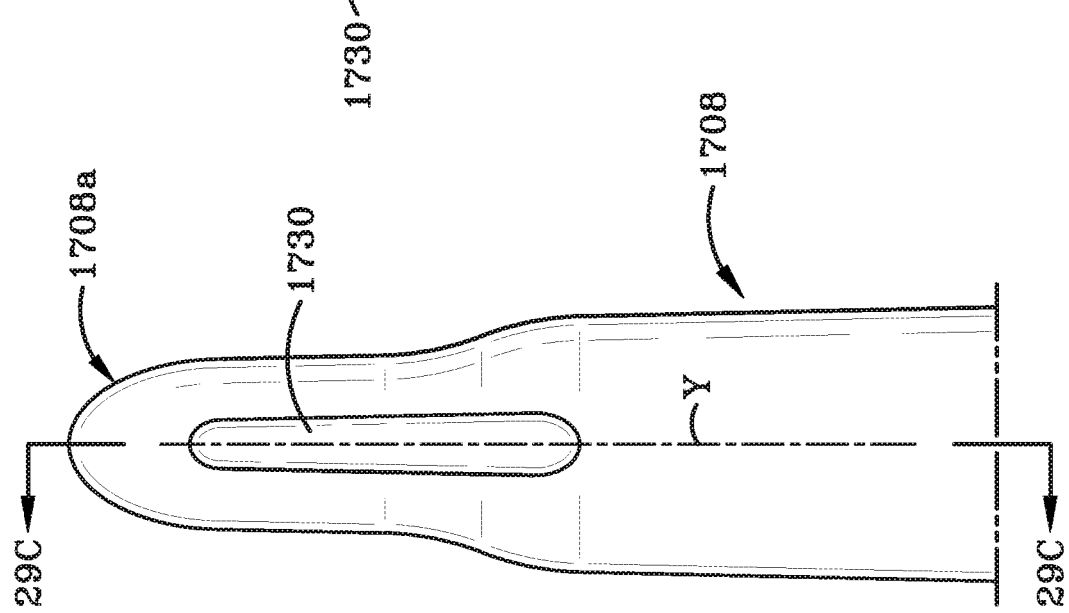
FIG. 29B is a side elevational view of the fingertip region that includes the fluted region taken along line 29B-29B of FIG. 29A.

FIG. 29D shows an alternative embodiment in which a second fluted region 1730 is defined in fingertip region 1708a. The second fluted region 1730 is oriented substantially parallel to longitudinal axis "Y". The two fingertip regions 1730 may be opposed to each other. Furthermore, the two fingertip regions may be formed in the opposed side surfaces of fingertip region 1708a, particularly being aligned generally along the midline of the side surfaces.

FIG. 29E shows yet another embodiment in which a second fluted region 1730 is defined in fingertip region 1730. In this instance, however, the second fluted region is located adjacent the first fluted region 1730. The two fluted regions may be located on the side surface of the index finger region 1708 that is adjacent the thumb region. The two fluted regions 1730 may be disposed on either side of the midline of the side surface of fingertip region 1708a. It will be understood that a second pair of fluted regions may be provided on the opposed side surface of the fingertip region 1708a. Fluted regions 1730 as shown in FIG. 29E extend for a distance into the cavity of index finger region 1708 in a similar manner to what is illustrated in FIG. 29C or FIG. 29D.

FIGS. 29F and 29G show yet another embodiment of a fingertip region that includes one or more fluted regions 1730. In this instance, however, the one or more fluted regions are oriented substantially at right angles to longitudinal axis "Y". Adjacent fluted regions may be spaced a short distance apart from each other and may extend into cavity 1708b. While five fluted regions are illustrated in FIGS. 29F and 29G, it will be understood that only a single fluted region may be provided on fingertip region 1708a or two or more, including more than five fluted regions may be provided. Fluted regions 1730 may be provided on a side surface of the fingertip region 1730, particularly on the side surface adjacent thumb region 1706. A second group of one or more fluted regions 1730 may be provided in fingertip region 1708a in a location opposed to the one or more fluted regions illustrated in FIGS. 29F and 29G. In other words, both groups of one or more fluted regions 1730 may be provided in side surfaces of fingertip region 1708a. The groups of fluted regions 1730 may each be oriented generally along a midline of the associated side surface of the fingertip region 1708.

It will be understood that any of the fluted regions illustrated herein may be provided at any location on the circumference of the fingertip region 1708a. Furthermore, one or more fluted regions may be provided on any or all of the fingertip regions on glove 1717. While the fluted regions 1730 have been illustrated as being provided on a fingertip region of reduced diameter, such fluted regions 1730 may be provided on a bullet-tip configured fingertip region or on a fingertip region that is not specifically reduced in circumference. Furthermore, additional fluted regions of any illustrated configuration may be provided at one or more locations around the circumference of the fingertip region.

In each finger region or thumb region of the gloves illustrated in FIGS. 27A-29G that has a fingertip region that is of a reduced or smaller circumference than the circumference of the associated remaining portion, the associated skirt acts as a step-down region.

As is evident from the description above and what follows hereafter, a glove in accordance with the present disclosure may be fabricated to include one or more of a plurality of different features.

The first feature is whether the glove is made to be a hand-specific or an ambidextrous glove. It should be understood that any of the gloves described herein may be fabricated as either a hand-specific glove or as an ambidextrous glove.

Another feature that may be incorporated into any of the gloves described herein relates to the fingertip regions provided on one or more of the thumb region, index finger region, middle finger region, ring finger region, or little finger region of the glove. In some examples of the glove, the fingertip region of one or more of the thumb region or finger regions may be of generally a same circumference as a remaining portion of the associated thumb region or finger region. In other examples, the fingertip region of one or more of the thumb and finger regions may be fabricated to be of a smaller circumference than the remaining portion of the associated thumb region or finger region; i.e., the fingertip region may be substantially narrower than the remaining portion of the associated thumb region or finger region. In yet other examples, the fingertip region of one or more of the thumb and finger regions may be fabricated with tip that that will be described later herein as a "bullet-tip region". This bullet-tip region is fabricated to have a smaller circumference than a remaining portion of the associated thumb region or finger region and a tapering conical region extends between the bullet fingertip region and the remaining portion of the associated thumb region or finger region. In some examples, only one fingertip region on the glove will be fabricated to be of a smaller circumference and the other fingertip regions will be of generally the same circumference as the associated remaining portion of the thumb region or finger regions. In other examples only one fingertip region on the glove may be fabricated as a bullet fingertip region and the other fingertip regions will not be bullet fingertip regions. In yet other examples two fingertip regions will be fabricated to be of a smaller circumference or as a bullet fingertip region and the other three fingertip regions will not be fabricated in this manner. In other examples, three fingertip regions will be fabricated to be of a smaller circumference or as a bullet fingertip region and the other two fingertip regions will not be fabricated in this manner. In other examples, four fingertip regions will be fabricated to be of a smaller circumference or as a bullet fingertip region and the other one fingertip region will not be fabricated in this manner. In other examples, all five fingertip regions will be fabricated to be of a smaller circumference or as a bullet fingertip region.

Still further, gloves may be fabricated to include a combination of one or more smaller circumference fingertip regions and/or one or more bullet fingertip regions and/or one or more fingertip regions that are neither smaller circumference nor bullet fingertip regions. The specific placement and combinations of the various types of fingertip regions may be utilized on a glove depending on the desired end-purpose and functionality of the glove.

Yet another feature that may be varied on the gloves in accordance with the present invention is whether one or more areas on the glove is textured or is free of texture (aka smooth). The pattern and placement of textured regions may utilize any one of a variety of different texture patterns including but not limited to a sand pattern, a diamond pattern, a herringbone pattern, a fan pattern, a fish-scale pattern, a wave pattern, a rib pattern etc. Gloves in accordance with this disclosure may have some areas that are left smooth or un-textured and other regions that are textured. In other examples, some areas of the glove may be smooth or un-textured, other regions may be provided with a first texture and yet other regions may be provided with a second texture or even a third texture thereon. In some examples, the fingertip regions of one or more of the thumb and finger regions may be left smooth while in other examples the fingertip regions of one or more of the thumb and finger regions may be provided with a first texture. In other examples, some of the fingertip regions may be left smooth while other fingertip regions are provided with a first texture and yet other fingertip regions are provided with a second texture. All of the fingertip regions may be smooth and the rest of the glove may be textured with one or more textures. (The rest of the glove may include a front surface and a back surface. The front surface may be one or more surfaces that are adjacent the user's palm or the front surfaces of the user's fingers and is able to contact objects when held in the user's hand. The back surface may be one or more of the surfaces opposite the front surface and which will be located adjacent a back of the user's hand or fingers.) All of the fingertip regions may be textured while the rest of the glove is left smooth. In other examples, one or more entire thumb region or finger region may be left smooth and un-textured while the rest of the glove may be textured, or vice versa. In other instances the fingertip region and the remaining portion of the same thumb region or finger region may differ from each other and/or from the rest of the glove. The fingertip region may be smooth and the remaining portion of the same thumb region or finger region may be textured or vice versa.

It is further to be understood that specific patterning of areas of the glove (i.e., smooth, not smooth, differently textured etc.) may be selected in accordance with the intended use of the glove. For example, one, two, three, four, or five smooth fingertip regions may be provided if tactile sensitivity in an activity is required. The tactile sensitivity can also be enhanced by providing smaller circumference fingertip regions or bullet fingertip regions on some or all of the thumb and finger regions. Texturing may be provided on one, two, three, four, or five fingertip regions if gripping ability is important in an activity. Utilizing smaller circumference fingertip regions or bullet fingertip regions may also enhance gripping ability. Any combination of texturing on any specific one or more of the thumb region and finger regions can be utilized to provide enhanced utility of a glove in accordance with this disclosure.

Another feature which is understood to be able to be incorporated into any glove in accordance with the present disclosure is the type of material used to fabricate the glove. Regardless of which particular glove is illustrated or described, it should be understood that the materials for fabrication can be selected from any of those described herein. The particular material will simply be selected to suit the end environment in which the particular glove will be utilized. The various described materials can therefore be utilized if the glove is hand-specific or ambidextrous, has same circumference fingertip regions or smaller circumference fingertip regions or bullet fingertip regions; and regardless of whether areas of the glove are to be made smooth or textured or multi-textured or a combination of these.

A further feature which may be utilized in any of the gloves described or illustrated herein is the production of finger regions or a thumb region that is relatively shorter than would typically be the case. For example, hands are typically shaped so that the middle finger is longer than the index and ring fingers and the little finger is shorter than all other fingers. Typically, the index and ring fingers are of approximately the same length. In some examples of gloves in accordance with the present disclosure, the length of the index finger region may be reduced or smaller so that the length thereof is shorter than the length of the ring finger region. In other examples, the length of the middle finger region may be reduced or smaller so that the length of the middle finger region more closely approximates the length of the index and ring finger regions. The length of the thumb region may also be reduced or smaller. The reduced or smaller length thumb region and finger region causes the material of those regions of the glove to be pulled tighter around the tip of the thumb or finger than would be the case if the thumb region or finger region was of a length more typically to the way people's hands are shaped. The tighter material increases tactile sensitivity because the material becomes stretched thin over the users thumb region or finger region. In other words, the thickness of the material between the interior and exterior surfaces of the glove is effectively reduced or smaller and therefore a person may more readily sense things through their thumb and fingers when they contact or hold something.

Yet a further feature that may be incorporated into any of the gloves illustrated or described herein is that of a rip, cut or tear-indicator. In particular, any of the gloves in accordance with the present invention may be fabricated to include an exterior surface or exterior layer of a first color and an interior surface or interior layer of a second color. The first color and second color are preferably sufficiently contrasting that if a rip, cut or tear forms in the glove, the color of the interior surface or layer will become immediately evident and visible to the wearer of the glove or to others that observe exterior surface of the glove on the wearer's hand.

The cuff or wrist region of the glove may also be folded or rolled back upon itself in such a fashion that the second color will form a rim or border at the base of the wrist region and contrast with the first color on the rest of the glove. The visible second color cuff or wrist region relative to the first colored rest of the glove may serve as evidence to persons selecting the glove that this particular glove includes a tear-indicator. The different color cuff or wrist region may further be utilized to symbolize the types of material from which the interior and exterior layers or surfaces are fabricated. For example, the interior layer or interior surface may be formed from a material that is free of or is essentially free of elements, components, or compounds that cause hypersensitivity or allergic reaction in people who wear the glove. A particular color may be provided in the interior layer or interior surface to indicate this property in the glove. In other instances, the interior surface or interior layer or exterior surface or exterior layer may be fabricated from a material that shields the user from exposure to certain dangerous substances. For example, the interior or exterior layer or surface may protect the wearer from being exposed to substances such as fentanyl. Again, a color provided in either of the interior surface or layer or exterior surface of layer of the glove may be used to signify this property.

It should further be understood that the different configurations regarding materials, length, fingertip regions, texturing, lack of texturing etc. described herein may be provided on a hand-specific glove or on an ambidextrous glove. It should be further understood that the various descriptions and figures provided herein are provided as examples of the types of feature combinations that may be utilized in a glove in accordance with this disclosure. The figures and description should therefore not be construed to limit the permutations and combinations in which the various features described herein may be provided on a glove in accordance with this disclosure.

The provision of smooth/differently textured fingertip regions has been described and illustrated herein in conjunction with hand-specific gloves and ambidextrous gloves. In the latter, the entire circumference of the index finger region, the middle finger region, and the thumb region may be provided with an un-textured surface or with a texture that differs from a rest of the glove or even from the other of fingertip regions of the index finger region, middle finger region and thumb region. Thus, the smooth/textured or differently textured "front surface" may be provided on each of the surfaces of the fingertip region that may selectively be positioned adjacent a front surface of the thumb, index finger or middle finger depending on whether the glove is worn on a left hand or a right hand.

It will be understood by those of ordinary skill in the art that providing smooth (i.e., un-textured) surfaces on the fingertip regions of the index finger region, middle finger region and or thumb region is helpful in many medically-related settings. For example, smooth fingertip regions on the index finger region and/or middle finger region may be helpful when checking a pulse, starting an IV, feeling for vein for IV—visual helps to start but must feel it before breaking the skin. Having a smooth fingertip region on the thumb region of the glove is also useful when starting an IV or when connecting an IV tube to a catheter as these have to be twisted and locked together. Having a smooth thumb also helps with a regulator on IV tubing as the medical professional has to "roll it" to clasp the tube and adjust the flow rate; and the thumb does the "rolling". Having a smooth fingertip region on the thumb region is also helpful with moving medicine thru an IV line as the thumb is used on a plunger to pump medicine thru the IV. Additionally, smooth fingertip regions on the thumb region and index and middle finger regions may be also helpful when prepping a needle sheath.

A thinner glove is good for procedures performed inside an ambulance for a better feel on the user's hand; like working on a patient as compared to outside the ambulance where actions can include more to do with moving the patient. In these instances a thicker glove may be helpful.

It will be understood that while the gloves disclosed herein have been discussed as being useful in the medical field, other fields of endeavor may benefit from utilizing gloves that embody the principles applied herein. For example, gloves used by people who shoot guns may be beneficial as they provide an enhanced or at least relatively unimpeded sense of touch along with an improved grip on a trigger.

In some instances, a glove in accordance with the present disclosure may have three fingertip regions (thumb region, index finger region and middle finger region) that are smooth and a sand texture on the ring finger region and little finger region and the rest of the glove, particularly or only the palm region, may be smooth (i.e., free of texture). Such a glove would be particularly useful in a hospital environment. In an EMS (emergency management services) environment a glove having three fingertip regions (thumb region, index finger region and middle finger region) that are smooth, with a diamond patterned texture or other texture or no texture on the palm region would be particularly helpful. The fingertip regions on the thumb region, index finger region, and middle finger region would also be helpful in both of these environments.

It will further be understood that the concepts disclosed herein may be utilized in gloves that may be manufactured from one of a medium acrylic nitrile (i.e., about 24% solids), high acrylic nitrile (i.e., about 45% solids), neoprene, natural rubber, and a polymer suitable for surgical gloves. Furthermore, the gloves may be manufactured from materials that are free of or essentially free of zinc, sulfur, fluoride, or cross-links. Still further, the glove material may be selected to be resistant to chemicals, particularly drugs. For example, the glove material may be resistant to opioids such as fentanyl and heroin. The glove material may be about 5 mm in thickness which enables the material in the fingertip regions to be pulled sufficient thin enough, when the glove is donned, for a user to be able to detect a patient's pulse therethrough. The gloves incorporating the features disclosed herein may be ambidextrous gloves, hand specific gloves, examination gloves or disposable gloves.

Gloves with smooth (i.e., untextured) fingertip regions on the thumb region, index region and middle finger regions make it easier for medical personnel to check a pulse, start an intra-venous (IV) drip, prepping a needle sheath, connecting an IV tube to a catheter, helping to twist and lock these components together. A smooth fingertip region on thumb region may help moving medication through an IV line as the thumb is used on a plunger to pump medication through the IV line. Smooth fingertip regions on two finger regions help to feel for a vein for an IV insertion. Thinner fingertip regions are helpful when inside an ambulance because tactile sensitivity is maintained.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration set out herein are an example and the disclosure is not limited to the exact details shown or described.

The invention claimed is:

1. A glove comprising:
a wrist region;
a palm region extending outwardly from the wrist region;
a thumb region, an index finger region, a middle finger region, a ring finger region and a little finger region all extending outwardly from the palm region;
wherein the glove is fabricated with an exterior surface thereof being of a first color and an interior surface thereof being of a second color, where the first color contrasts with the second color; and wherein the first color and the second color are a tear indicator when the glove is one of cut, ripped and torn; and
a cuff provided at an end of the wrist region; wherein the cuff comprises a portion of the wrist region that is one of rolled and folded back upon itself; wherein the cuff is of the second color and a rest of the wrist region is of the first color.

2. The glove as defined in claim 1, wherein the second color is visible on the exterior surface of the glove when the glove is one of cut, ripped and torn.

3. The glove as defined in claim 1, further comprising:
a fingertip region and a remaining portion provided on each of the thumb region, index finger region, middle finger region, ring finger region, and little finger region, wherein the fingertip region extends from proximate a tip to proximate where a first knuckle of one of a user's thumb and respective finger will be located when the glove is worn; and wherein the remaining portion extends from a lower end of the fingertip region to the palm region; and
wherein at least one of the fingertip regions of the thumb region, the index finger region, the middle finger region, the ring finger region, and the little finger region is of a reduced circumference relative to a circumference of the associated remaining portion.

4. The glove as defined in claim 3, wherein the at least one of the fingertip regions is smooth and free of texture.

5. The glove as defined in claim 4, wherein the glove is fabricated from one of a medium acrylic nitrile, a high acrylic nitrile, neoprene, and natural rubber.

6. The glove as defined in claim 3, wherein the at least one of the fingertip regions is provided with a texture.

7. The glove as defined in claim 1, wherein the wrist region, palm region, thumb region, index finger region, middle finger region, ring finger region and the little finger region include a material that is free of or is essentially free of elements, components and compounds that cause hypersensitivity and allergic reaction in people who wear the glove.

8. The glove as defined in claim 7, wherein the material is nitrile rubber.

9. The glove as defined in claim 8, wherein the nitrile rubber is free of or essentially free of zinc and/or sulfur and/or accelerators.

10. The glove as defined in claim 9, wherein the wrist region, the palm region, the thumb region, the index finger region, the middle finger region, the ring finger region and the little finger region further include an elastomeric polymer.

11. The glove as defined in claim 3, wherein the at least one of the fingertip regions is of a reduced circumference relative to the associated remaining portion.

12. The glove as defined in claim 11, wherein the at least one of the fingertip regions comprises only a first fingertip region selected from the fingertip regions of the thumb region, the index finger region, the middle finger region, the ring finger region and the little finger region.

13. The glove as defined in claim 11, wherein the at least one of the fingertip regions comprises a first fingertip region and a second fingertip region selected from the fingertip regions of the thumb region, the index finger region, the middle finger region, the ring finger region and the little finger region.

14. The glove as defined in claim 11, wherein the at least one of the fingertip regions comprises a first fingertip region, a second fingertip region, and a third fingertip region selected from the fingertip regions of the thumb region, the index finger region, the middle finger region, the ring finger region and the little finger region.

15. The glove as defined in claim 12, wherein the first fingertip region is the fingertip region of the index finger region.

16. The glove as defined in claim 13, wherein the first fingertip region is the fingertip region of the index finger region, and the second fingertip region is the fingertip region of the middle finger region.

17. The glove as defined in claim 14, wherein the first fingertip region is the fingertip region of the index finger region, the second fingertip region is the fingertip region of the middle finger region, and the third fingertip region is the fingertip region of the thumb region.

18. The glove as defined in claim 3, wherein the at least one of the fingertip regions has a bullet-tip configuration.

19. The glove as defined in claim 18, further comprising a tapered skirt that extends between the fingertip region having the bullet-tip configuration and the associated remaining portion.

20. The glove as defined in claim 18, wherein the fingertip region having the bullet-tip configuration is the fingertip region of the index finger region.

21. The glove as defined in claim 19, wherein the fingertip region having the bullet-tip configuration is of a substantially constant circumference from the skirt to the tip of the associated thumb region, index finger region, middle finger region, ring finger region and little finger region.

* * * * *